United States Patent [19]
Ryals et al.

[11] Patent Number: 6,091,004
[45] Date of Patent: Jul. 18, 2000

[54] GENE ENCODING A PROTEIN INVOLVED IN THE SIGNAL TRANSDUCTION CASCADE LEADING TO SYSTEMIC ACQUIRED RESISTANCE IN PLANTS

[75] Inventors: John Andrew Ryals, Cary, N.C.; Terrence Patrick Delaney, Ithaca, N.Y.; Leslie Bethards Friedrich, Apex, N.C.; Kristianna Baldwin Weymann, Portland, Oreg.; Kay Ann Lawton, Raleigh, N.C.; Daniel Murray Ellis, Cary, N.C.; Scott Joseph Uknes, Apex, N.C.; Taco Peter Jesse, Johan Fabriciuskade; Pieter Vos, Renswoude, both of Netherlands

[73] Assignee: Novartis Finance Corporation, New York, N.Y.

[21] Appl. No.: 08/880,179

[22] Filed: Jun. 20, 1997

Related U.S. Application Data

[60] Provisional application No. 60/020,272, Jun. 21, 1996, provisional application No. 60/024,883, Aug. 30, 1996, provisional application No. 60/033,177, Dec. 13, 1996, provisional application No. 60/034,379, Dec. 27, 1996, provisional application No. 60/034,730, Jan. 10, 1997, and provisional application No. 60/035,022, Jan. 10, 1997.

[51] Int. Cl.$^7$ .............................. A01H 5/00; C12N 5/14; C12N 15/29; C12N 15/82
[52] U.S. Cl. ................. 800/301; 435/320.1; 435/419; 435/468; 536/23.6; 800/279; 800/305; 800/306; 800/307; 800/309; 800/310; 800/312; 800/313; 800/315; 800/317; 800/317.2; 800/317.3; 800/317.4; 800/318; 800/320; 800/320.2; 800/320.3
[58] Field of Search ...................... 536/23.6; 435/172.3, 435/320.1, 419; 800/205, DIG. 57, DIG. 58, DIG. 55, DIG. 56, DIG. 42, DIG. 46, DIG. 40, DIG. 9, DIG. 25, DIG. 23, DIG. 13, DIG. 16, DIG. 15, DIG. 60, DIG. 21, DIG. 8, DIG. 31, DIG. 35, DIG. 19, DIG. 32, DIG. 34, DIG. 33, DIG. 65, DIG. 37, DIG. 64, DIG. 54, DIG. 26, DIG. 43, DIG. 44

[56] References Cited

U.S. PATENT DOCUMENTS 5,614,395  3/1997  Ryals et al. ..................... 435/172.3

FOREIGN PATENT DOCUMENTS

| 0 534 858 | 3/1993 | European Pat. Off. . |
| WO 94/16077 | 7/1994 | WIPO . |
| WO 95/19443 | 7/1995 | WIPO . |

OTHER PUBLICATIONS

Stam M, et al. "The silence of genes in transgenic plants." Ann. Bot. 79: 3–12, 1997.

Koziel MG, et al. "Optimizing expression of transgenes with an emphasis on post–transcriptional events." Plant Mol. Biol. 32: 393–405, 1996.

Smith CJS, et al. "Antisense RNA inhibition of polygalacturonase gene expression in transgenic tomatoes." Nature 334: 724–726, Aug. 25, 1988.

Newman T, et al. "Genes galore: A summary of methods for accessing results from large–scale partial sequencing of anonymous Arabidopsis cDNA clones." Plant Physiol. 106: 1241–1255, 1994.

Rothstein SJ, et al. "Promoter cassettes, antibiotic–resistance genes, and vectors for plant transformation." Gene 53: 153–161, 1987.

Genback Accession No. T22612, Cao et al., Cell 88(1): 57–63 (1997).

Genback Accession No. U76707, Newman et al., Plant Physiol., 106: 1241–1255 (1994).

Hunt et al., Recent advances in systemic acquired resistance research—a review, Gene, 179: 89–95 (1996).

Alexander et al., "Increased tolerance to two oomycete pathogens in transgenic tobacco expressing pathogenesis–related protein 1a", *Proc. Natl. acad. Sci.* 90: 7327–7331 (1993).

Bell et al., "Assignment of 30 Microsatellite Loci to the Linkage Map of Arabidopsis", *Genomics* 19, 137–144 (1994).

Bhat, K.S., "Generation of a plasmid vector for deletion cloning by rapid multiple site–directed mutagenesis", *Gene* 134: 83–87 (1993).

Bi et al., "Hydrogen peroxide does not function downstream of salicylic acid in the induction of PR protein expression", *The Plant Journal*, 8(2): 235–245 (1995).

Bouchez et al., "A new YAC library for genome mapping in Arabidopsis", Abstract, 6$^{th}$ International Conference on Arabidopsis Research (1995).

Bowling et al., "A Mutation in Arabidopsis That Leads to Constitutive Expression of Systemic Acquired Resistance", *The Plant Cell*, 6: 1845–1857 (1994).

Büschges et al., "The Barley Mlo Gene: A Novel Control Element of Plant Pathogen Resistance", *Cell*, 88: 695–704 (1997).

Cameron et al., "Biologically induced systemic acquired resistance in *Arabidopsis thaliana*", *The Plant Journal* 5(5): 715–725 (1994).

Cao et al., "Characterization of an Arabidopsis Mutant That Is Nonresponsive to Inducers of Systemic Acquired Resistance", *The Plant Cell*, 6: 1583–1592 (1994).

Cao et al., "The Arabidopsis NPR1 Gene that Controls Systemic Acquired Resistance Encodes a Novel Protein Containing Ankyrin Repeats", *Cell*, 88: 57–63 (1997).

(List continued on next page.)

*Primary Examiner*—Amy J. Nelson
*Attorney, Agent, or Firm*—J. Timothy Meigs

[57] ABSTRACT

The invention concerns the location and characterization of a gene (designated NIM1) that is a key component of the SAR pathway and that in connection with chemical and biological inducers enables induction of SAR gene expression and broad spectrum disease resistance in plants. The invention further concerns transformation vectors and processes for overexpressing the NIM1 gene in plants. The transgenic plants thus created have broad spectrum disease resistance.

25 Claims, 17 Drawing Sheets

OTHER PUBLICATIONS

Century et al., "NDR1, a locus of *Arabidopsis thaliana* that is required for disease resistance to both a bacterial and a fungal protein", *Proc. Natl. Acad. Sci.,* 92: 6597–6601 (1995).

Creusot et al., "The CIC library: a large insert YAC library for genome mapping in *Arabidopsis thaliana*", *The Plant Journal,* 8(5): 763–770 (1995).

Delaney et al., "A Central Role of Salicylic Acid in Plant Disease Resistance", *Science,* 266: 1247–1250 (1994).

Delaney et al., "Arabidopsis signal transduction mutants defective in chemically and biologically induced disease resistance", Abstract, 6$^{th}$ International Meeting on Arabidopsis Research, (1995).

Delaney et al., "Arabidopisis signal transduction mutant defective in chemically and biologically induced disease resistance", *Proc. Natl. Acad. Sci.,* 92: 6602–6606 (1995).

Delaney, T.P., "Genetic Dissection of Acquired Resistance to Disease", *Plant Physiol.* 113: 1–12 (1997).

Dietrich et al., "Arabidopsis Mutants Simulating Disease Resistance Response", *Cell* 77: 565–577 (1994).

Elledge et al., "λYES: Amultifunctional cDNA expression vector for the isolation of genes by complementation of yeast and *Escherichia coli* mutations", *Proc. Natl. Acad. Sci., USA* 88:1731–1735 (1991).

Friedrich et al., "A benzothiadiazole derivative induces systemic acquired resistance in tobacco", *The Plant Journal,* 10: 61–70 (1996).

Gaffney et al., "Requirement of Salicylic Acid for the Induction of Systemic Acquired Resistance", *Science* 261: 754–756 (1993).

Gatz C., "Chemical Control of Gene Expression", *Ann. Rev. Plant Physiol. Plant Mol. Biol.* 48: 89–108 (1997).

Glazebrook et al., "Isolation of Arabidopsis Mutants With Enhanced Disease Susceptibility by Direct Screening", *Genetics* 143: 973–982 (1996).

Görlach et al., "Benzothiadiazole, a Novel Class of Inducers of Systemic Acquired Resistance, Activates Gene Expression and Disease Resistance in Wheat", *The Plant Cell* 8: 629–643 (1996).

Greenberg et al., "Programmed Cell Death in Plants: A Pathogen–Triggered Response Activated Coordinately with Multiple Defense Functions", *Cell* 77: 551–563 (1994).

Hebsgaard et al., "Splice site prediction in *Arabidopsis thaliana* pre–mRNA by combining local and global sequence information", *Nucleic Acids Research* 24: 3439–3452 (1996).

Hunt et al., "Systemic Acquired Resistance Signal Transduction", *Critical Reviews in Plant Sciences* 15: 583–606 (1996).

Kessmann et al., "Induction of Systemic Acquired Disease Resistance in Plants by Chemicals", *Annu. Rev. Phytopathol.* 32: 439–459 (1994).

Lawton et al., "The Molecular Biology of Systemic Acquired Resistance", *Mechanisms of Plant Defense Responses,* B. Fritig and M. Legrand (eds.) Kluwer Academic Publishers (Netherlands) 422–432 (1993).

Lawton et al., "Systemic Acquired Resistance in Arabidopsis Requires Salicylic Acid but Not Ethylene", *Molecular Plant–Microbe Interactions* 8: 863–870 (1995).

Lawton et al., "Benzothiadiazole induces disease resistance in Arabidopsis by activation of the systemic acquired resistance signal transduction pathway" *The Plant Journal* 10: 71–82 (1996).

Lister et al., "Recombinant inbred lines for mapping RFLP and phenotypic markers in *Arabidopsis thaliana*" *The Plant Journal* 4: 745–750 (1993).

Liu et al., "Generation of a high–quality P1 library of Arabidopsis suitable for chromosome walking", *The Plant Journal* 7: 351–358 (1995).

Maher et al., "Increased disease susceptibility of transgenic tobacco plants with suppressed levels of preformed phenylpropanoid products", *Proc. Natl. Acad. Sci., USA,* 91: 7802–7806 (1994).

Mauch–Mani et al., "Systemic Acquired Resistance in *Arabidopsis thaliana* Induced by a Predisposing Infection with a Pathogenic Isolate of *Fusarium oxysporum*", *Molecular Plant–Microbe Interactions* 7: 378–383 (1994).

Mauch–Mani et al., "Production of Salicylic Acid Precursors Is a Major Function of Phenylalanine Ammonia–Lyase in the Resistance of Arabidopsis to *Peronospora parasitica*", *The Plant Cell* 8: 203–212 (1996).

Métraux et al., "Increase in Salicylic Acid at the Onset of Systemic Acquired Resistance in Cucumber", *Science* 250: 1004–1006 (1990).

Mindrinos et al., "The *A. thaliana* Disease Resistance Gene RPS2 Encodes a Protein Containing a Nucleotide–Binding Site and Leucine–Rich Repeats", *Cell* 78: 1089–1099 (1994).

Pallas et al., "Tobacco plants epigenetically suppressed in phenylalanine ammonia–lyase expression do not develop systemic acquired resistance in response to infection by tobacco mosaic virus", *The Plant Journal* 10: 281–293 (1996).

Parker et al., "Characterization of eds1, a Mutation in Arabidopsis Suppressing Resistance to *Peronospora parasitica* Specified by Several Different RPP Genes", *The Plant Cell* 8: 2033–2046 (1996).

Payne et al., "Isolation of the genomic clone for pathogenesis–related protein 1a from *Nicotiana tabacum* cv. Xanthi–nc", *Plant Molecular Biology* 11: 89–94 (1988).

Ryals et al., "Signal transduction in systemic acquired resistance", *Proc. Natl. Acad. Sci. USA* 92: 4202–4205 (1995).

Ryals et al., "Systemic Acquired Resistance", *The Plant Cell* 8: 1809–1819 (1996).

Ryals et al., "The Arabidopsis NIM1 Protein Shows Homology to the Mammalian Transcription Factor Inhibitor IkB", *The Plant Cell* 9: 425–439 (1997).

Shulaev, et al., "Is Salicylic Acid a Translocated Signal of Systemic Acquired Resistance in Tobacco?", *The Plant Cell* 7: 1691–1701 (1995).

Simoens et al., "Isolation of genes expressed in specific tissues of *Arabidopsis thaliana* by differential screening of a genomic library", *Gene* 67: 1–11 (1988).

Uknes et al., "Acquired Resistance in Arabidopsis", *The Plant Cell* 4: 645–656 (1992).

Uknes et al., "Regulation of Pathogenesis–Related Protein–1a Gene Expression in Tobacco", *The Plant Cell* 5: 159–169 (1993).

Uknes et al., "Biological Induction of Systemic Acquired Resistance in Arabidopsis", *Molecular Plant–Microbe Interactions* 6: 692–698 (1993).

Uknes et al., "Reduction of risk for growers: methods for the development of disease–resistant crops", *New Phytol.* 133: 3–10 (1996).

Vernooij et al., "Salicylic Acid Is Not the Translocated Signal Responsible for Inducing Systemic Acquired Resistance but Is Required in Signal Transduction", *The Plant Cell* 6: 959–965 (1994).

Vernooij et al., "2,6–Dichloroisonicotinic Acid–Induced Resistance to Pathogens Without the Accumulation of Salicylic Acid", *Molecular Plant–Microbe Interactions* 8: 228–234 (1995).

Verwoerd et al., "A small–scale procedure for the rapid isolation of plant RNAs", *Nucleic Acids Research* 17: 2362 (1989).

Vos et al., "AFLP: a new technique for DNA fingerprinting", *Nucleic Acids Research* 23: 4407–4414 (1995).

Ward et al., "Coordinate Gene Activity in Response to Agents That Induce Systemic Acquired Resistance", *The Plant Cell* 3: 1085–1094 (1991).

Weymann et al., "Suppression and Restoration of Lesion Formation in Arabidopsis Isd Mutants", *The Plant Cell* 7: 2013–2022 (1995).-

```
tgtgatgcaagtcatgggatattgctttgtgttaagtatacaaaaccatcacgtggatac    60
atagtcttcaaaccaaccactaaacagtatcaggtcataccaaagccagaagtgaagggt   120
tgggatatgtcattgggtttagcggtaatcggattgaacccttccggtataaaatacaa   180
aggctttcgcagtctcggcgtatgtgtatgtctcggggtatctaccatttgaatcacaga   240
acttttatgtgcgaagttttcgattctgattcgtttacctggaagagattagaaaatttg   300
cgtctaccaaaaacagacagattaattttttccaacccgatacaagtttcggggttcttg   360
cattggatatcacggaacaacaatgtgatccggttttgtctcaaaaccgaaacttggtcc   420
ttcttccatactccgaactctgatgttttctcaggattagtcagatacgaagggaagcta   480
ggtgctattcgtcagtggacaaacaaagatcaagaagatgttcacgagttatgggtttta   540
aagagcagttttgaaaagtcgtgggttaaagtgaaagatattaaaagcattggagtagat   600
ttgattacgtggactccaagcaacgacgttgtattgtttcgtagtagtgatcgtggttgc   660
ctctacaacataaacgcagagaagttgaatttagtttatgcaaaaaagagggatctgat   720
tgttctttcgtttgttttccgttttgttctgattacgagagggttgatctgaacggaaga   780
agcaacgggccgacactttaaaaaaaaaataaaaaaaatgggccgacaaatgcaaacgta   840
gttgacaaggatctcaagtctcaagtctcaattggctcgctcattgtggggcataaatat   900
atctagtgatgtttaattgttttttataaggtaaaaaggaatattgaattttgtttctta   960
ggtttatgtaataataccaaacattgtttatgaatatttaatctgattttttggctagt  1020
tattttattatatcaagggttcctgtttatagttgaaaacagttactgtatagaaaatag  1080
tgtcccaatttctctcttaaataatatattagttaataaaagatattttaatatattag  1140
```

FIGURE 6A

| Sequence | Position |
|---|---|
| atatacataatatctaaagcaacacatatttagacacaacacgtaatatcttactattgt | 1200 |
| ttacatatatttatagcttaccaatataacccgtatctatgttttataagcttttataca | 1260 |
| atatatgtacggtatgctgtccacgtatatatattctccaaaaaaaacgcatggtacaca | 1320 |
| aaatttattaaatatttggcaattgggtgtttatctaaagtttatcacaatatttatcaa | 1380 |
| ctataatagatggtagaagataaaaaaattatatcagattgattcaattaaattttataa | 1440 |
| tatatcattttaaaaaattaattaaaagaaaactatttcataaaattgttcaaaagataa | 1500 |
| ttagtaaaattaattaaatatgtgatgctattgagttatagagagttattgtaaatttac | 1560 |
| ttaaaatcatacaaatcttatcctaatttaacttatcatttaagaaatacaaaagtaaaa | 1620 |
| aacgcggaaagcaataatttatttaccttattataactcctatataaagtactctgttta | 1680 |
| ttcaacataatcttacgttgttgtattcataggcatctttaacctatcttttcattttct | 1740 |
| gatctcgatcgttttcgatccaacaaaatgagtctaccggtgaggaaccaagaggtgatt | 1800 |
| atgcagattccttcttcttctcagtttccagcaacatcgagtccggaaaacaccaatcaa | 1860 |
| gtgaaggatgagccaaatttgtttagacgtgttatgaatttgcttttacgtcgtagttat | 1920 |
| tgaaaaagctgatttatcgcatgattcagaacgagaagttgaaggcaaataactaaagaa | 1980 |
| gtcttttatatgtatacaataattgtttttaaatcaaatcctaattaaaaaaatatattc | 2040 |
| attatgactttcatgtttttaatgtaatttattcctatatctataatgattttgttgtga | 2100 |
| agagcgttttcatttgctatagaacaaggagaatagttccaggaaatattcgacttgatt | 2160 |
| taattatagtgtaaacatgctgaacactgaaaattacttttcaataaacgaaaatata | 2220 |
| atatacattacaaaacttatgtgaataaagcatgaaacttaatatacgttccctttatca | 2280 |

FIGURE 6B

```
ttttacttcaaagaaaataaacagaaatgtaactttcacatgtaaatctaattcttaaat    2340 ttaaaaaataatatttatatatttatatgaaaataacgaaccggatgaaaaataaatttt    2400 atatatttatatcatctccaaatctagtttggttcaggggcttaccgaaccggattgaac    2460 ttctcatatacaaaaattagcaacacaaaatgtctccggtataaatactaacatttataa    2520 cccgaaccggtttagcttcctgttatatcttttaaaaaagatctctgacaaagattcct    2580 ttcctggAAATTTACCGGTTTTGGTGAAATGTAAACCGTGGACGAGGATGCTTCTTCAT    2640

ATCTCACCACCACTCTCGTTGACTTGACTTGGCTCTGCTCGTCAATGGTTATCTTCGATC    2700

TTTAACCAAATCCAGTTGATAAGGTCTCTTCGTTGATTAGCAGAGATCTCTTTAATTTGT    2760

GAATTTCAATTCATCGGAACCTGTTG ATG GAC ACC ACC ATT GAT GGA TTC GCC    2813
                           Met Asp Thr Thr Ile Asp Gly Phe Ala

GAT TCT TAT GAA ATC AGC AGC ACT AGT TTC GTC GCT ACC GAT AAC ACC    2861
Asp Ser Tyr Glu Ile Ser Ser Thr Ser Phe Val Ala Thr Asp Asn Thr

GAC TCC TCT ATT GTT TAT CTG GCC GCC GAA CAA GTA CTC ACC GGA CCT    2909
Asp Ser Ser Ile Val Tyr Leu Ala Ala Glu Gln Val Leu Thr Gly Pro

GAT GTA TCT GCT CTG CAA TTG CTC TCC AAC AGC TTC GAA TCC GTC TTT    2957
Asp Val Ser Ala Leu Gln Leu Leu Ser Asn Ser Phe Glu Ser Val Phe

GAC TCG CCG GAT GAT TTC TAC AGC GAC GCT AAG CTT GTT CTC TCC GAC    3005
Asp Ser Pro Asp Asp Phe Tyr Ser Asp Ala Lys Leu Val Leu Ser Asp

GGC CGG GAA GTT TCT TTC CAC CGG TGC GTT TTG TCA GCG AGA AGC TCT    3053
Gly Arg Glu Val Ser Phe His Arg Cys Val Leu Ser Ala Arg Ser Ser

TTC TTC AAG AGC GCT TTA GCC GCC GCT AAG AAG GAG AAA GAC TCC AAC    3101
Phe Phe Lys Ser Ala Leu Ala Ala Ala Lys Lys Glu Lys Asp Ser Asn
```

FIGURE 6C

```
AAC ACC GCC GCC GTG AAG CTC GAG CTT AAG GAG ATT GCC AAG GAT TAC   3149
Asn Thr Ala Ala Val Lys Leu Glu Leu Lys Glu Ile Ala Lys Asp Tyr

GAA GTC GGT TTC GAT TCG GTT GTG ACT GTT TTG GCT TAT GTT TAC AGC   3197
Glu Val Gly Phe Asp Ser Val Val Thr Val Leu Ala Tyr Val Tyr Ser

AGC AGA GTG AGA CCG CCG CCT AAA GGA GTT TCT GAA TGC GCA GAC GAG   3245
Ser Arg Val Arg Pro Pro Pro Lys Gly Val Ser Glu Cys Ala Asp Glu

AAT TGC TGC CAC GTG GCT TGC CGG CCG GCG GTG GAT TTC ATG TTG GAG   3293
Asn Cys Cys His Val Ala Cys Arg Pro Ala Val Asp Phe Met Leu Glu
        - deleted in nim1-3
GTT CTC TAT TTG GCT TTC ATC TTC AAG ATC CCT GAA TTA ATT ACT CTC   3341
Val Leu Tyr Leu Ala Phe Ile Phe Lys Ile Pro Glu Leu Ile Thr Leu TAT CAG gtaaaacaccatctgcattaagctatggttacacattcatgaatatgttc        3397
Tyr Gln ttacttgagtacttgtatttgtatttcag AGG CAC TTA TTG GAC GTT GTA GAC    3450
                              Arg His Leu Leu Asp Val Val Asp AAA GTT GTT ATA GAG GAC ACA TTG GTT ATA CTC AAG CTT GCT AAT ATA   3498
Lys Val Val Ile Glu Asp Thr Leu Val Ile Leu Lys Leu Ala Asn Ile TGT GGT AAA GCT TGT ATG AAG CTA TTG GAT AGA TGT AAA GAG ATT ATT   3546
Cys Gly Lys Ala Cys Met Lys Leu Leu Asp Arg Cys Lys Glu Ile Ile
                                                A inserted in nim1-1
GTC AAG TCT AAT GTA GAT ATG GTT AGT CTT GAA AAG TCA TTG CCG GAA   3594
Val Lys Ser Asn Val Asp Met Val Ser Leu Glu Lys Ser Leu Pro Glu GAG CTT GTT AAA GAG ATA ATT GAT AGA CGT AAA GAG CTT GGT TTG GAG   3642
Glu Leu Val Lys Glu Ile Ile Asp Arg Arg Lys Glu Leu Gly Leu Glu GTA CCT AAA GTA AAG AAA CAT GTC TCG AAT GTA CAT AAG GCA CTT GAC   3690
Val Pro Lys Val Lys Lys His Val Ser Asn Val His Lys Ala Leu Asp
```

FIGURE 6D

```
TCG GAT GAT ATT GAG TTA GTC AAG TTG CTT TTG AAA GAG GAT CAC ACC   3738
Ser Asp Asp Ile Glu Leu Val Lys Leu Leu Leu Lys Glu Asp His Thr
                            T in niml-2
AAT CTA GAT GAT GCG TGT GCT CTT CAT TTC GCT GTT GCA TAT TGC AAT   3786
Asn Leu Asp Asp Ala Cys Ala Leu His Phe Ala Val Ala Tyr Cys Asn GTG AAG ACC GCA ACA GAT CTT TTA AAA CTT GAT CTT GCC GAT GTC AAC   3834
Val Lys Thr Ala Thr Asp Leu Leu Lys Leu Asp Leu Ala Asp Val Asn CAT AGG AAT CCG AGG GGA TAT ACG GTG CTT CAT GTT GCT GCG ATG CGG   3882
His Arg Asn Pro Arg Gly Tyr Thr Val Leu His Val Ala Ala Met Arg
            T in niml-6
AAG GAG CCA CAA TTG ATA CTA TCT CTA TTG GAA AAA GGT GCA AGT GCA   3930
Lys Glu Pro Gln Leu Ile Leu Ser Leu Leu Glu Lys Gly Ala Ser Ala TCA GAA GCA ACT TTG GAA GGT AGA ACC GCA CTC ATG ATC GCA AAA CAA   3978
Ser Glu Ala Thr Leu Glu Gly Arg Thr Ala Leu Met Ile Ala Lys Gln GCC ACT ATG GCG GTT GAA TGT AAT AAT ATC CCG GAG CAA TGC AAG CAT   4026
Ala Thr Met Ala Val Glu Cys Asn Asn Ile Pro Glu Gln Cys Lys His TCT CTC AAA GGC CGA CTA TGT GTA GAA ATA CTA GAG CAA GAA GAC AAA   4074
Ser Leu Lys Gly Arg Leu Cys Val Glu Ile Leu Glu Gln Glu Asp Lys CGA GAA CAA ATT CCT AGA GAT GTT CCT CCC TCT TTT GCA GTG GCG GCC   4122
Arg Glu Gln Ile Pro Arg Asp Val Pro Pro Ser Phe Ala Val Ala Ala
                                             A in niml-4, niml-5
GAT GAA TTG AAG ATG ACG CTG CTC GAT CTT GAA AAT AGA G              4162
Asp Glu Leu Lys Met Thr Leu Leu Asp Leu Glu Asn Arg gtatctatcaagtcttatttcttatatgtttgaattaaatttatgtcctctctattagga     4222 aactgagtgaactaatgataactattctttgtgtcgtccactgttta gTT GCA CTT      4278
                                                Val Ala Leu
```

FIGURE 6E

```
GCT CAA CGT CTT TTT CCA ACG GAA GCA CAA GCT GCA ATG GAG ATC GCC    4326
Ala Gln Arg Leu Phe Pro Thr Glu Ala Gln Ala Ala Met Glu Ile Ala

GAA ATG AAG GGA ACA TGT GAG TTC ATA GTG ACT AGC CTC GAG CCT GAC    4374
Glu Met Lys Gly Thr Cys Glu Phe Ile Val Thr Ser Leu Glu Pro Asp

CGT CTC ACT GGT ACG AAG AGA ACA TCA CCG GGT GTA AAG ATA GCA CCT    4422
Arg Leu Thr Gly Thr Lys Arg Thr Ser Pro Gly Val Lys Ile Ala Pro

TTC AGA ATC CTA GAA GAG CAT CAA AGT AGA CTA AAA GCG CTT TCT AAA    4470
Phe Arg Ile Leu Glu Glu His Gln Ser Arg Leu Lys Ala Leu Ser Lys

ACC Ggtatggattctcacccacttcatcggactccttatcacaaaaaacaaaac             4524
Thr taaatgatctttaaacatggttttgttacttgctgtctgaccttgttttttttatcatca      4584 gTG GAA CTC GGG AAA CGA TTC TTC CCG CGC TGT TCG GCA GTG CTC        4629
Val Glu Leu Gly Lys Arg Phe Phe Pro Arg Cys Ser Ala Val Leu

GAC CAG ATT ATG AAC TGT GAG GAC TTG ACT CAA CTG GCT TGC GGA GAA    4677
Asp Gln Ile Met Asn Cys Glu Asp Leu Thr Gln Leu Ala Cys Gly Glu

GAC GAC ACT GCT GAG AAA CGA CTA CAA AAG AAG CAA AGG TAC ATG GAA    4725
Asp Asp Thr Ala Glu Lys Arg Leu Gln Lys Lys Gln Arg Tyr Met Glu

ATA CAA GAG ACA CTA AAG AAG GCC TTT AGT GAG GAC AAT TTG GAA TTA    4773
Ile Gln Glu Thr Leu Lys Lys Ala Phe Ser Glu Asp Asn Leu Glu Leu

GGA AAT TCG TCC CTG ACA GAT TCG ACT TCT TCC ACA TCG AAA TCA ACC    4821
Gly Asn Ser Ser Leu Thr Asp Ser Thr Ser Ser Thr Ser Lys Ser Thr

GGT GGA AAG AGG TCT AAC CGT AAA CTC TCT CAT CGT CGT CGG TGA        4866
Gly Gly Lys Arg Ser Asn Arg Lys Leu Ser His Arg Arg Arg  *

GACTCTTGCCTCTTAGTGTAATTTTTGCTGTACCATATAATTCTGTTTTCATGATGACTG       4926

TAACTGTTTATGTCTATCGTTGGCGTCATATAGTTTCGCTCTTCGTTTTGCATCCTGTGT       4986
```

FIGURE 6F

```
ATTATTGCTGCAGGTGTGCTTCAAACAAATGTTGTAACAATTTGAACCAATGGTATACAG    5046

ATTTGTAatatatatttatgtacatcaacaataacccatgatggtgttacagagttgcta    5106 gaatcaaagtgtgaaataatgtcaaattgttcatctgttggatattttccaccaagaacc    5166 aaaagaatattcaagttccctgaacttctggcaacattcatgttatatgtatcttcctaa    5226 ttcttcctttaaccttttgtaactcgaattacacagcaagttagtttcaggtctagagat    5286 aagagaacactgagtgggcgtgtaaggtgcattctcctagtcagctccattgcatccaac    5346 atttgtgaatgacacaagttaacaatcctttgccacatttctgggtgcatacatggaaac    5406 ttcttcgattgaaacttcccacatgtgcaggtgcgttcgctgtcactgatagaccaagag    5466 actgaaagctttcacaaattgccctcaaatcttctgtttctatcgtcatgactccatatc    5526 tccgaccactggtcatgagccagagcccactgattttgagggaattgggctaaccatttc    5586 cgagcttctgagtccttcttttgatgtcctttatgtaggaatcaaattcttccttctga    5646 cttgtggat    5655
```

FIGURE 6G

```
NIM1    :  267 VSNVHKALDSDDIELVKLLLKEDHINLDDACALHFAVAYCN 307
                +   +  +ALD+ DIELVKL++   +   +LDDA A+H+AV +CN
Rice-1  :   33 IRRMRRALDAADIELVKLMVMGEGLDLDDALAVHYAVQHCN 155

NIM1    :  327 PRGYTVLHVAAMRKEPQLILSLLEKGASASEATLEGRT 364
                P G T LH+AA       P ++  LL+  A  +  T +G T
Rice-1  :  215 PTGKTALHLAAEMVSPDMVSVLLDHHADXNFRTXDGVT 328

NIM1    :  267 VSNVHKALDSDDIELVKLLLKEDHINLDDACALHFAVAYCN 307
                +   +  +ALD+ DIELVKL++   +   +LDDA A+H+AV +CN
Rice-2  :   33 IRRMRRALDAADIELVKLMVMGEGLDLDDALAVHYAVQHCN 155

NIM1    :  325 RNPRGYTVLHVAAMRKEPQLILSLLEK 351
                R P    T LH+AA       P ++  LL++
Rice-2  :  208 RRPDSKTALHLAAEMVSPDMVSVLLDQ 288

NIM1    :  267 VSNVHKALDSDDIELVKLLLKEDHINLDDACALHFAVAYCN 307
                +   +  +ALD+ DIELVKL++   +   +LDDA A+H+AV +CN
Rice-3  :   33 IRRMRRALDAADIELVKLMVMGEGLDLDDALAVHYAVQHCN 155

NIM1    :  325 RNPRGYTVLHVAAMRKEPQLILSLLEK 351
                R P    T LH+AA       P ++  LL++
Rice-3  :  208 RRPDSKTALHLAAEMVSPDMVSVLLDQ 288

NIM1    :  267 VSNVHKALDSDDIELVKLLLKEDHINLDDACALHFAVAYCN 307
                +   +  +ALD+ DIELVKL++   +   +LDDA A+H+AV +CN
Rice-4  :   33 IRRMRRALDAADIELVKLMVMGEGLDLDDALAVHYAVQHCN 155

NIM1    :  327 PRGYTVLHVAAMRKEPQLI 345
                P G T LH+AA       P ++
Rice-4  :  215 PTGKTALHLAAEMVSPDMV 271
```

FIGURE 8

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
       (A) LENGTH: 9919 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
TGATCATGAA TTGCGTGTAG GGTTGTGTTT TAAAGATAGG GATGAGCTGA AGAAGGCGGT      60
GGACTGGTGT TCCATTAGAG GGCAGCAAAA GTGTGTAGTA CAAGAGATTG AGAAGGACGA     120
GTATACGTTT AAATGCATCA GATGGAAATG CAATTGGTCG CGTCGGGCAG ATTGAATAGA     180
AGAACATGGA CTTGTTAAGA TAACTAAGTG TAGTTGGTCC ACATACTTGT TGTTCTATTA     240
AGCCGGAAAA CTTCAACTTG TAATTTGCAG CAGAAGAGAT TGAGTGTCTG ATCAGGGTAC     300
AACCCACTCT AACAGCAGAG TTGAAAAGTT TGGTGACATG CTTAAAACTT CAAAGCTGCG     360
GGCAGCAGAA CAGGAAGTAA TCAAAGATCA GAGTTTCAGA GTATTGCCTA AACTAATTGG     420
CTGCATTTCA CTCATCTAAT GGGCTACTTG TGGACTGCAA TATGAGCTTT TCCCTAATCC     480
TGAATTTGCA TCCTTCGGTG GCGCGTTTTG GGCGTTTCCA CAGTCCATTG AAGGGTTTCA     540
ACACTGTAGA CCTCTGATCA TAGTGGATTC AAAAGACTTG AACGGCAAGT ACCCTATGAA     600
ATTGATGATT TCCTCAGGAC TCGACGCTGA TGATTGCTTT TTCCCGCTTG CCTTTCCGCT     660
TACCAAAGAA GTGTCCACTG ATAGTTGGCG TTGGTTTCTC ACTAATATCA GAGAGAAGGT     720
AACACAAAGG AAAGACGTTT GCCTCGTCTC CAGTCCTCAC CCGGACATAG TTGCTGTTAT     780
TAACGAACCC GGATCACTGT GGCAAGAACC TTGGGTCTAT CACAGGTTCT GTCTGGATTG     840
TTTTTGCTTA CAATTCCATG ATATTTTTGG AGACTACAAC CTGGTGAGCC TTGTGAAGCA     900
GGCTGGATCC ACAAGTCAGA AGGAAGAATT TGATTCCTAC ATAAAGGACA TCAAAAAGAA     960
GGACTCAGAA GCTCGGAAAT GGTTAGCCCA ATTCCCTCAA AATCAGTGGG CTCTGGCTCA    1020
TGACCAGTGG TCGGAGATAT GGAGTCATGA CGATAGAAAC AGAAGATTTG AGGGCAATTT    1080
GTGAAAGCTT TCAGTCTCTT GGTCTATCAG TGACAGCGAA CGCACCTGCA CATGTGGGAA    1140
GTTTCAATCG AAGAAGTTTC CATGTATGCA CCCAGAAATG GTGCAAAGGA TTGTTAACTT    1200
GTGTCATTCA CAAATGTTGG ATGCAATGGA GCTGACTAGG AGAATGCACC TTACACGCCC    1260
ACTCAGTGTT CTCTTATCTC TAGACCTGAA ACTAACTTGC TGTGTAATTC GAGTTACAAA    1320
AGGTTAAAGG AAGAATTAGG AAGATACATA TAACATGAAT GTTGCCAGAA GTTCAGGGAA    1380
CTTGAATATT CTTTTGGTTC TTGGTGGAAA ATATCCAACA GATGAACAAT TTGACATTAT    1440
TTCACACTTT GATTCTAGCA ACTCTGTAAC ACCATCATGG GTTATTGTTG ATGTACATAA    1500
ATATATATTA CAAATCTGTA TACCATTGGT TCAAATTGTT ACAACATTTG TTTGAAGCAC    1560
ACCTGCAGCA ATAATACACA GGATGCAAAA CGAAGAGCGA AACTATATGA CGCCAACGAT    1620
AGACATAAAC AGTTACAGTC ATCATGAAAA CAGAATTATA TGGTACAGCA AAAATTACAC    1680
```

-continued

```
TAAGAGGCAA GAGTCTCACC GACGACGATG AGAGAGTTTA CGGTTAGACC TCTTTCCACC   1740

GGTTGATTTC GATGTGGAAG AAGTCGAATC TGTCAGGGAC GAATTCCTA ATTCCAAATT    1800

GTCCTCACTA AAGGCCTTCT TTAGTGTCTC TTGTATTTCC ATGTACCTTT GCTTCTTTTG   1860

TAGTCGTTTC TCAGCAGTGT CGTCTTCTCC GCAAGCCAGT TGAGTCAAGT CCTCACAGTT   1920

CATAATCTGG TCGAGCACTG CCGAACAGCG CGGGAAGAAT CGTTTCCCGA GTTCCACTGA   1980

TGATAAAAAA AACAAGGTCA GACAGCAAGT AACAAAACCA TGTTTAAAGA TCATTTAGTT   2040

TTGTTTTTTG TGATAAGGAG TCCGATGAAG TGGGTGAGAA TCCATACCGG TTTTAGAAAG   2100

CGCTTTTAGT CTACTTTGAT GCTCTTCTAG GATTCTGAAA GGTGCTATCT TTACACCCGG   2160

TGATGTTCTC TTCGTACCAG TGAGACGGTC AGGCTCGAGG CTAGTCACTA TGAACTCACA   2220

TGTTCCCTTC ATTTCGGCGA TCTCCATTGC AGCTTGTGCT TCCGTTGGAA AAAGACGTTG   2280

AGCAAGTGCA ACTAAACAGT GGACGACACA AAGAATAGTT ATCATTAGTT CACTCAGTTT   2340

CCTAATAGAG AGGACATAAA TTTAATTCAA ACATATAAGA AATAAGACTT GATAGATACC   2400

TCTATTTTCA AGATCGAGCA GCGTCATCTT CAATTCATCG GCCGCCACTG CAAAAGAGGG   2460

AGGAACATCT CTAGGAATTT GTTCTCGTTT GTCTTCTTGC TCTAGTATTT CTACACATAG   2520

TCGGCCTTTG AGAGAATGCT TGCATTGCTC CGGGATATTA TTACATTCAA CCGCCATAGT   2580

GGCTTGTTTT GCGATCATGA GTGCGGTTCT ACCTTCCAAA GTTGCTTCTG ATGCACTTGC   2640

ACCTTTTTCC AATAGAGATA GTATCAATTG TGGCTCCTTC CGCATCGCAG CAACATGAAG   2700

CACCGTATAT CCCCTCGGAT TCCTATGGTT GACATCGGCA AGATCAAGTT TTAAAAGATC   2760

TGTTGCGGTC TTCACATTGC AATATGCAAC AGCGAAATGA AGAGCACACG CATCATCTAG   2820

ATTGGTGTGA TCCTCTTTCA AAAGCAACTT GACTAACTCA ATATCATCCG AGTCAAGTGC   2880

CTTATGTACA TTCGAGACAT GTTTCTTTAC TTTAGGTACC TCCAAACCAA GCTCTTTACG   2940

TCTATCAATT ATCTCTTTAA CAAGCTCTTC CGGCAATGAC TTTTCAAGAC TAACCATATC   3000

TACATTAGAC TTGACAATAA TCTCTTTACA TCTATCCAAT AGCTTCATAC AAGCTTTACC   3060

ACATATATTA GCAAGCTTGA GTATAACCAA TGTGTCCTCT ATAACAACTT TGTCTACAAC   3120

GTCCAATAAG TGCCTCTGAA ATACAAATAC AAGTACTCAA GTAAGAACAT ATTCATGAAT   3180

GTGTAACCAT AGCTTAATGC AGATGGTGTT TTACCTGATA GAGAGTAATT AATTCAGGGA   3240

TCTTGAAGAT GAAAGCCAAA TAGAGAACCT CCAACATGAA ATCCACCGCC GGCCGGCAAG   3300

CCACGTGGCA GCAATTCTCG TCTGCGCATT CAGAAACTCC TTTAGGCGGC GGTCTCACTC   3360

TGCTGCTGTA AACATAAGCC AAAACAGTCA CAACCGAATC GAAACCGACT TCGTAATCCT   3420

TGGCAATCTC CTTAAGCTCG AGCTTCACGG CGGCGGTGTT GTTGGAGTCT TTCTCCTTCT   3480

TAGCGGCGGC TAAAGCGCTC TTGAAGAAAG AGCTTCTCGC TGACAAAACG CACCGGTGGA   3540

AAGAAACTTC CCGGCCGTCG GAGAGAACAA GCTTAGCGTC GCTGTAGAAA TCATCCGGCG   3600

AGTCAAAGAC GGATTCGAAG CTGTTGGAGA GCAATTGCAG AGCAGATACA TCAGGTCCGG   3660

TGAGTACTTG TTCGGCGGCC AGATAAACAA TAGAGGAGTC GGTGTTATCG GTAGCGACGA   3720

AACTAGTGCT GCTGATTTCA TAAGAATCGG CGAATCCATC AATGGTGGTG TCCATCAACA   3780

GGTTCCGATG AATTGAAATT CACAAATTAA AGAGATCTCT GCTAATCAAC GAAGAGACCT   3840

TATCAACTGG ATTTGGTTAA AGATCGAAGA TAACCATTGA CGAGCAGAGC CAAGTCAAGT   3900

CAACGAGAGT GGTGGTGAGA TATGAAGAAG CATCCTCGTC CCACGGTTTA CATTTCACCA   3960

AAACCGGTAA ATTTCCAGGA AAGGAATCTT TGTCAGAGAT CTTTTTTAAA AAGATATAAC   4020
```

-continued

```
AGGAAGCTAA ACCGGTTCGG GTTATAAATG TTAGTATTTA TACCGGAGAC ATTTTGTGTT      4080

GCTAATTTTT GTATATGAGA AGTTCAATCC GGTTCGGTAA GCCCCTGAAC CAAACTAGAT      4140

TTGGAGATGA TATAAATATA TAAAATTTAT TTTTCATCCG GTTCGTTATT TTCATATAAA      4200

TATATAAATA TTATTTTTTA AATTTAAGAA TTAGATTTAC ATGTGAAAGT TACATTTCTG      4260

TTTATTTTCT TTGAAGTAAA ATGATAAAGG GAACGTATAT TAAGTTTCAT GCTTTATTCA      4320

CATAAGTTTT GTAATGTATA TTATATTTTT CGTTTATTGA AAAAGTAATT TTCAGTGTTC      4380

AGCATGTTTA CACTATAATT AAATCAAGTC GAATATTTCC TGGAACTATT CTCCTTGTTC      4440

TATAGCAAAT GAAAACGCTC TTCACAACAA AATCATTATA GATATAGGAA TAAATTACAT      4500

TAAAAACATG AAAGTCATAA TGAATATATT TTTTTAATTA GGATTTGATT TAAAAACAAT      4560

TATTGTATAC ATATAAAAGA CTTCTTTAGT TATTTGCCTT CAACTTCTCG TTCTGAATCA      4620

TGCGATAAAT CAGCTTTTTC AATAACTACG ACGTAAAAGC AAATTCATAA CACGTCTAAA      4680

CAAATTTGGC TCATCCTTCA CTTGATTGGT GTTTTCCGGA CTCGATGTTG CTGGAAACTG      4740

AGAAGAAGAA GGAATCTGCA TAATCACCTC TTGGTTCCTC ACCGGTAGAC TCATTTTGTT      4800

GGATCGAAAA CGATCGAGAT CAGAAAATGA AAAGATAGGT TAAAGATGCC TATGAATACA      4860

ACAACGTAAG ATTATGTTGA ATAAACAGAG TACTTTATAT AGGAGTTATA ATAAGGTAAA      4920

TAAATTATTG CTTTCCGCGT TTTTTACTTT TGTATTTCTT AAATGATAAG TTAAATTAGG      4980

ATAAGATTTG TATGATTTTA AGTAAATTTA CAATAACTCT CTATAACTCA ATAGCATCAC      5040

ATATTTAATT AATTTTACTA ATTATCTTTT GAACAATTTT ATGAAATAGT TTTCTTTTAA      5100

TTAATTTTTT AAAATGATAT ATTATAAAAT TTAATTGAAT CAATCTGATA TAATTTTTTT      5160

ATCTTCTACC ATCTATTATA GTTGATAAAT ATTGTGATAA ACTTTAGATA AACACCCAAT      5220

TGCCAAATAT TTAATAAATT TTGTGTACCA TGCGTTTTTT TTGGAGAATA TATATACGTG      5280

GACAGCATAC CGTACATATA TTGTATAAAA GCTTATAAAA CATAGATACG GGTTATATTG      5340

GTAAGCTATA AATATATGTA AACAATAGTA AGATATTACG TGTTGTGTCT AAATATGTGT      5400

TGCTTTAGAT ATTATGTATA TCTAATATAT TAAAATATCT TTTATTAACT AATATATTAT      5460

TTAAGAGAGA AAATTGGGAC ACTATTTTCT ATACAGTAAC TGTTTTCAAC TATAAACAGG      5520

AACCCTTGAT ATAATAAAAT AACTAGCCAA AAAATCAGAT TAAATATTCA TAAAACAATG      5580

TTTGGTATTA TTACATAAAC CTAAGAAACA AAATTCAATA TTCCTTTTTA CCTTATAAAA      5640

AACAATTAAA CATCACTAGA TATATTTATG CCCCACAATG AGCGAGCCAA TTGAGACTTG      5700

AGACTTGAGA TCCTTGTCAA CTACGTTTGC ATTTGTCGGC CCATTTTTTT TATTTTTTTT      5760

TTAAAGTGTC GGCCCGTTGC TTCTTCCGTT CAGATCAACC CTCTCGTAAT CAGAACAAAA      5820

CGGAAAACAA ACGAAAGAAC AATCAGATCC CTCTTTTTTT GCATAAACTA AATTCAACTT      5880

CTCTGCGTTT ATGTTGTAGA GGCAACCACG ATCACTACTA CGAAACAATA CAACGTCGTT      5940

GCTTGGAGTC CACGTAATCA AATCTACTCC AATGCTTTTA ATATCTTTCA CTTTAACCCA      6000

CGACTTTTCA AAACTGCTCT TTAAAACCCA TAACTCGTGA ACATCTTCTT GATCTTTGTT      6060

TGTCCACTGA CGAATAGCAC CTAGCTTCCC TTCGTATCTG ACTAATCCTG AGAAAACATC      6120

AGAGTTCGGA GTATGGAAGA AGGACCAAGT TTCGGTTTTG AGACAAAACC GGATCACATT      6180

GTTGTTCCGT GATATCCAAT GCAAGAACCC CGAAACTTGT ATCGGGTTGG AAAAAATTAA      6240

TCTGTCTGTT TTTGGTAGAC GCAAATTTTC TAATCTCTTC CAGGTAAACG AATCAGAATC      6300

GAAAACTTCG CACATAAAAG TTCTGTGATT CAAATGGTAG ATACCCCGAG ACATACACAT      6360

ACGCCGAGAC TGCGAAAGCC TTTGTATTTT ATACCGGAAA GGGTTCAATC CGATTACCGC      6420
```

-continued

```
TAAACCCAAT GACATATCCC AACCCTTCAC TTCTGGCTTT GGTATGACCT GATACTGTTT    6480

AGTGGTTGGT TTGAAGACTA TGTATCCACG TGATGGTTTT GTATACTTAA CACAAAGCAA    6540

TATCCCATGA CTTGCATCAC AAGCTTCGAT CTTTATCATT CCGGGTGGCA GAAAGTCGAT    6600

GGAGACTCCA TTGTTTTGTA AATCACTCCT CTCATGGACA AAACTGGTTC GAAGTTCGTG    6660

TCCTTTTACT ATGTAGTGTT GTATGAAGTA TCCCGAAATA CGATTGGTTC TAAGGAGATT    6720

AAGATTGACA AACCATGACT CGTAGCTTCT CTTGTTGCAC TCTTTATTCA GGAGCCTGAA    6780

TTTTCCGATT TTTGACGCCG GAAGATAAGA AAGAAATTCT TGGATCATGT CTTGATTTAT    6840

CACCGGAGAA CTCATGATCC TGTCGGGAAT AAAGAGATGA GCACGATCAC TGAATGAGAA    6900

ATGAAAAAAT CAGGATCGGT AGAGAACAAC TTATGATGAA TAAAGTGTTT ATATATCCTT    6960

TCTTTGTTTA AGGAAAGTAT CAAAATTTGC CTTTTTCTTC GCTAGTCCTA AAACAAACAA    7020

ATTAACCAAA AGATAAAATC TTTCATGATT AATGTTACTT GTGATACCTT AAGCCAAAAC    7080

TTTATCTTTA GACTTTTAAC CAAATCTACA GTAATTTAAT TGCTAGACTT AGGAAACAAC    7140

TTTTTTTTTT ACCCAACAAT CTTTGGATTT TAATTGTTTT TTTTTCTACT AATAGATTAA    7200

CAACTCATTA TATAATAATG TTTCTATCAT AATTGACAAT TCTTTCTTTT TAATAAACAT    7260

CCAGCTTGTA TAATAATCCA CAAGTCAATT TCACCATTTT GGCCAATTTA TTTTCTTATA    7320

AAAATTAGCA CAAAAAGAT TATCATTGTT TAGCAGATTT AATTTCTAAT TAACTTACGT    7380

AATTTCCATT TTCCATAGAT TTATCTTTCT TTTTATTTCC TTAGTTATCT TAGTACTTTC    7440

TTAGTTTCCT TAGTAATTTT AAATTTTAAG ATAATATATT GAAATTAAAA GAAGAAAAA    7500

AACTCTAGTT ATACTTTTGT TAAATGTTTC ATCACACTAA CTAATAATTT TTTTTAGTTA    7560

AATTACAATA TATAAACACT GAAGAAAGTT TTTGGCCCAC ACTTTTTTGG GATCAATTAG    7620

TACTATAGTT AGGGGAAGAT TCTGATTTAA AGGATACCAA AAATGACTAG TTAGGACATG    7680

AATGAAAACT TATAATCTCA ATAACATACA TACGTGTTAC TGAACAATAG TAACATCTTA    7740

CGTGTTTTGT CCATATATTT GTTGCTTATA AATATATTCA TATAACAATG TTTGCATTAA    7800

GCTTTTAAGA AGCACAAAAC CATATAACAA AATTAAATAT TCCTATCCCT ACCAAAAAAA    7860

AAAATTAAAT ATTCCTACAG CCTTGTTGAT TATTTTATGC CCTACGTTGA GCCTTGTTGA    7920

CTAGTTTGCA TTTGTCGGTC CATTTCTTCT TCCGTCCAGA TCAACCCTCT CGTAATCAGA    7980

ACAAAAGGGG AAACAAACGT AAGAGGCAAA ATCCTTGTTT GTATGAACTA AGTTTAACTT    8040

CTCTGTGTTT AAGTTGTAGA GGCAAACATG ATCCCAACTA GAAAGCATTA CGACGTCGTT    8100

GCTTGGTATC CACGTAATAT GCTCTACTCC AATGCTTTCA ATATCTTTCA CTTTTTCCCA    8160

CGACTTTTCA AAACTGCTCT TTAAAACCCA TAATCTGTGA ACATCTTCTT GATTGTTGTT    8220

TATCCAGTGA CGAATAACAC CTAGCTTCCC TTCGTAGCTG ACTAACTCTG GAATAAACC    8280

AACGTTTGGA GTATGTAAGA AAGACCAAGT TTCGGTTTTG GACATAACC GGATCACATT    8340

GTGGTTCCAT GATCTCCAAT GCAAGAACCC TGAAGCTTGT ACCGGGTTTG AAAGAATTAG    8400

ACCGTCTGTT CTCGGTAGAC GCAAATTTTT TAATCTCTTC CACATAAACG AATCGGAATC    8460

AAAAACTTCG CACGCAAAAG TTCTGAGATT CCGAGTCATA CCAGGCGATT TCGAAAGCCT    8520

AAATATTTTA TACCGGAAAG GCTGCAATCC GGTTACCGTT AGACCTAATG ACTTATCACA    8580

ACTCCTCACT TTTGGGTTTG GTATGATCTG ATACTGTTTT GTTGTTGGTT TGCAGACTAT    8640

GTATTCCGGT ATTGGTCTTG TATCATTATA ACAAAGCAAT ATCCCATGAC GTGCATCACA    8700

AGCTTTGATC TTTACCTCTC CTTGTGGCAG AAAATCGATG GAGACTCCTT TGTTATCCAA    8760
```

```
ATCTCTCCTC TCATGGAAAA AACTGGTATC AAGTTTGTAT CCTCTTTCGT AGCGTTCTAG      8820

GAAGTATCCA GAGATATTGT TGGTTCGATG GAGATTTAGG TTGACAAACC AAGACTCGTA      8880

GCTTCTCTTG TTGCACTCTT TATTGATGAG CCTCAATTTT CCGATTTCGG ACCCCCGAAG      8940

ATAAGAAAGA ACCTCTTGGA TCGTGTCCTG ATTTATCACC GGAGAACTCA TGATCTTATT      9000

GGAAAAAAGA AAGAAAGAGA TGAGCACGAT CAGTGAATGA GATATATAGA AATCAGGATT      9060

GGTAGAGAAC CGACGATGAT GAATATACAA GTGTTTATAA GTATCACAAA TTGCCTTTTT      9120

CTTCGCTAGT CCCAAAACAA GCAAATTAAC CAAAGATAAA ATCTTCATTA ATGTTTTCCT      9180

TTTTCTTCGC CAGTCCCAGA TAAAAATATA TATAAAATAT TTCATTAGGT TACTTGTAGT      9240

ACCTTGAGCC CAAAGTTTCT CTTTTGACTT TTAACCAAAT TAACAGTAAT TTAATAGCTA      9300

GACTTAGAAA ACAACATTTT GTATATATAT TCTTTGACAT CAAAATTCAA CAATCTTTGG      9360

GTTTCTATAG TGTTTTTTTT CTTATTCTAA TAGATTACCA CTCATTATAT CATATACAAA      9420

GTGTTTCCTT TTCAATCAAC ATCCATTTTC TTTAAAAATT AGCAAGTTTG TTCTTATATC      9480

ATCATTCAGC AGATTTCTTA ATTAAACTTA GTGATTTCCA TTTTGCACCT ATATGTTTCT      9540

CTTTCTTAGT TTAGTACTTT AAATTTTCAT ATATATAATT TATTAAAATT AAAAGTAAAA      9600

ACTCCAGTTT AACTTATGTT AAATGTTTCA TCACACTAAA AGAGCATTAA GTAATAAATA      9660

TTTTAGCTTT ATGAAAAAAA ATATCAAATC ACTGAAGACA TTTGTTGGCC TATACTCTAT      9720

TTTTTATTTG GCCAATTAGT AATAGACTAA TAGTAACTCA TATGATATCT CTCTAATTCT      9780

GGCGAAACGA ATATTCTGAT TCTAAAGATA GTAAAAATGA ATTTTGATGA AGGGAATACT      9840

ATTTCACACA CCTAGAAAGA GTAAGGTAGA AACCTTTTTT TTTTTGGTCA GATTCTTGTA      9900

TCAAGAAGTT CTCATCGAT                                                  9919

(2) INFORMATION FOR SEQ ID NO:2:

(i) SEQUENCE CHARACTERISTICS:
        (A) LENGTH: 5655 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: exon
        (B) LOCATION: 2787..3347
        (D) OTHER INFORMATION: /product= "1st exon of NIM1"

(ix) FEATURE:
        (A) NAME/KEY: exon
        (B) LOCATION: 3427..4162
        (D) OTHER INFORMATION: /product= "2nd exon of NIM1"

(ix) FEATURE:
        (A) NAME/KEY: exon
        (B) LOCATION: 4271..4474
        (D) OTHER INFORMATION: /product= "3rd exon of NIM1"

(ix) FEATURE:
        (A) NAME/KEY: exon
        (B) LOCATION: 4586..4866
        (D) OTHER INFORMATION: /product= "4th exon of NIM1"

(ix) FEATURE:
        (A) NAME/KEY: CDS
        (B) LOCATION: join(2787..3347, 3427..4162, 4271..4474,
            4586..4866)
```

(xi) SEQUENCE DESCRIPTION: SEQ ID NO:2:

```
TGTGATGCAA GTCATGGGAT ATTGCTTTGT GTTAAGTATA CAAAACCATC ACGTGGATAC      60

ATAGTCTTCA AACCAACCAC TAAACAGTAT CAGGTCATAC CAAAGCCAGA AGTGAAGGGT     120

TGGGATATGT CATTGGGTTT AGCGGTAATC GGATTGAACC CTTTCCGGTA TAAAATACAA     180

AGGCTTTCGC AGTCTCGGCG TATGTGTATG TCTCGGGGTA TCTACCATTT GAATCACAGA     240

ACTTTTATGT GCGAAGTTTT CGATTCTGAT TCGTTTACCT GGAAGAGATT AGAAAATTTG     300

CGTCTACCAA AAACAGACAG ATTAATTTTT TCCAACCCGA TACAAGTTTC GGGGTTCTTG     360

CATTGGATAT CACGGAACAA CAATGTGATC CGGTTTTGTC TCAAAACCGA ACTTGGTCC      420

TTCTTCCATA CTCCGAACTC TGATGTTTTC TCAGGATTAG TCAGATACGA AGGGAAGCTA     480

GGTGCTATTC GTCAGTGGAC AAACAAAGAT CAAGAAGATG TTCACGAGTT ATGGGTTTTA     540

AAGAGCAGTT TTGAAAAGTC GTGGGTTAAA GTGAAAGATA TTAAAAGCAT GGAGTAGAT      600

TTGATTACGT GGACTCCAAG CAACGACGTT GTATTGTTTC GTAGTAGTGA TCGTGGTTGC     660

CTCTACAACA TAAACGCAGA GAAGTTGAAT TTAGTTTATG CAAAAAAGA GGGATCTGAT      720

TGTTCTTTCG TTTGTTTTCC GTTTTGTTCT GATTACGAGA GGGTTGATCT GAACGGAAGA     780

AGCAACGGGC CGACACTTTA AAAAAAAAAT AAAAAAAATG GGCCGACAAA TGCAAACGTA     840

GTTGACAAGG ATCTCAAGTC TCAAGTCTCA ATTGGCTCGC TCATTGTGGG GCATAAATAT     900

ATCTAGTGAT GTTAATTGT TTTTTATAAG GTAAAAGGA ATATTGAATT TTGTTTCTTA      960

GGTTTATGTA ATAATACCAA ACATTGTTTT ATGAATATTT AATCTGATTT TTTGGCTAGT    1020

TATTTTATTA TATCAAGGGT TCCTGTTTAT AGTTGAAAAC AGTTACTGTA TAGAAAATAG    1080

TGTCCCAATT TTCTCTCTTA AATAATATAT TAGTTAATAA AAGATATTTT AATATATTAG    1140

ATATACATAA TATCTAAAGC AACACATATT TAGCACACAAC ACGTAATATC TTACTATTGT   1200

TTACATATAT TTATAGCTTA CCAATATAAC CCGTATCTAT GTTTTATAAG CTTTTATACA    1260

ATATATGTAC GGTATGCTGT CCACGTATAT ATATTCTCCA AAAAAAACGC ATGGTACACA    1320

AAATTTATTA AATATTTGGC AATTGGGTGT TTATCTAAAG TTTATCACAA TATTTATCAA    1380

CTATAATAGA TGGTAGAAGA TAAAAAAATT ATATCGATT GATTCAATTA AATTTTATAA     1440

TATATCATTT TAAAAAATTA ATTAAAAGAA AACTATTTCA TAAAATTGTT CAAAAGATAA    1500

TTAGTAAAAT TAATTAAATA TGTGATGCTA TTGAGTTATA GAGAGTTATT GTAAATTTAC    1560

TTAAAATCAT ACAAATCTTA TCCTAATTTA ACTTATCATT TAAGAAATAC AAAAGTAAAA    1620

AACGCGGAAA GCAATAATTT ATTTACCTTA TTATAACTCC TATATAAAGT ACTCTGTTTA    1680

TTCAACATAA TCTTACGTTG TTGTATTCAT AGGCATCTTT AACCTATCTT TTCATTTTCT    1740

GATCTCGATC GTTTTCGATC CAACAAAATG AGTCTACCGG TGAGGAACCA AGAGGTGATT    1800

ATGCAGATTC CTTCTTCTTC TCAGTTTCCA GCAACATCGA GTCCGAAAAA CACCAATCAA    1860

GTGAAGGATG AGCCAAATTT GTTTAGACGT GTTATGAATT TGCTTTTACG TCGTAGTTAT    1920

TGAAAAAGCT GATTTATCGC ATGATTCAGA ACGAGAAGTT GAAGGCAAAT AACTAAAGAA    1980

GTCTTTTATA TGTATACAAT AATTGTTTTT AAATCAAATC CTAATTAAAA AAATATATTC    2040

ATTATGACTT TCATGTTTTT AATGTAATTT ATTCCTATAT CTATAATGAT TTTGTTGTGA    2100

AGAGCGTTTT CATTTGCTAT AGAACAAGGA GAATAGTTCC AGGAAATATT CGACTTGATT    2160

TAATTATAGT GTAAACATGC TGAACACTGA AAATTACTTT TTCAATAAAC GAAAAATATA    2220

ATATACATTA CAAAACTTAT GTGAATAAAG CATGAAACTT AATATACGTT CCCTTTATCA    2280
```

```
                                                                    -continued

TTTTACTTCA AAGAAAATAA ACAGAAATGT AACTTTCACA TGTAAATCTA ATTCTTAAAT     2340

TTAAAAAATA ATATTTATAT ATTTATATGA AAATAACGAA CCGGATGAAA AATAAATTTT     2400

ATATATTTAT ATCATCTCCA AATCTAGTTT GGTTCAGGGG CTTACCGAAC CGGATTGAAC     2460

TTCTCATATA CAAAAATTAG CAACACAAAA TGTCTCCGGT ATAAATACTA ACATTTATAA     2520

CCCGAACCGG TTTAGCTTCC TGTTATATCT TTTTAAAAAA GATCTCTGAC AAAGATTCCT     2580

TTCCTGGAAA TTTACCGGTT TTGGTGAAAT GTAAACCGTG GGACGAGGAT GCTTCTTCAT     2640

ATCTCACCAC CACTCTCGTT GACTTGACTT GGCTCTGCTC GTCAATGGTT ATCTTCGATC     2700

TTTAACCAAA TCCAGTTGAT AAGGTCTCTT CGTTGATTAG CAGAGATCTC TTTAATTTGT     2760

GAATTTCAAT TCATCGGAAC CTGTTG ATG GAC ACC ACC ATT GAT GGA TTC GCC     2813
                                Met Asp Thr Thr Ile Asp Gly Phe Ala
                                 1               5

GAT TCT TAT GAA ATC AGC AGC ACT AGT TTC GTC GCT ACC GAT AAC ACC     2861
Asp Ser Tyr Glu Ile Ser Ser Thr Ser Phe Val Ala Thr Asp Asn Thr
 10              15                  20                  25

GAC TCC TCT ATT GTT TAT CTG GCC GCC GAA CAA GTA CTC ACC GGA CCT     2909
Asp Ser Ser Ile Val Tyr Leu Ala Ala Glu Gln Val Leu Thr Gly Pro
                 30                  35                  40

GAT GTA TCT GCT CTG CAA TTG CTC TCC AAC AGC TTC GAA TCC GTC TTT     2957
Asp Val Ser Ala Leu Gln Leu Leu Ser Asn Ser Phe Glu Ser Val Phe
             45                  50                  55

GAC TCG CCG GAT GAT TTC TAC AGC GAC GCT AAG CTT GTT CTC TCC GAC     3005
Asp Ser Pro Asp Asp Phe Tyr Ser Asp Ala Lys Leu Val Leu Ser Asp
         60                  65                  70

GGC CGG GAA GTT TCT TTC CAC CGG TGC GTT TTG TCA GCG AGA AGC TCT     3053
Gly Arg Glu Val Ser Phe His Arg Cys Val Leu Ser Ala Arg Ser Ser
     75                  80                  85

TTC TTC AAG AGC GCT TTA GCC GCC GCT AAG AAG GAG AAA GAC TCC AAC     3101
Phe Phe Lys Ser Ala Leu Ala Ala Ala Lys Lys Glu Lys Asp Ser Asn
 90                  95                 100                 105

AAC ACC GCC GCC GTG AAG CTC GAG CTT AAG GAG ATT GCC AAG GAT TAC     3149
Asn Thr Ala Ala Val Lys Leu Glu Leu Lys Glu Ile Ala Lys Asp Tyr
                110                 115                 120

GAA GTC GGT TTC GAT TCG GTT GTG ACT GTT TTG GCT TAT GTT TAC AGC     3197
Glu Val Gly Phe Asp Ser Val Val Thr Val Leu Ala Tyr Val Tyr Ser
            125                 130                 135

AGC AGA GTG AGA CCG CCG CCT AAA GGA GTT TCT GAA TGC GCA GAC GAG     3245
Ser Arg Val Arg Pro Pro Pro Lys Gly Val Ser Glu Cys Ala Asp Glu
        140                 145                 150

AAT TGC TGC CAC GTG GCT TGC CGG CCG GCG GTG GAT TTC ATG TTG GAG     3293
Asn Cys Cys His Val Ala Cys Arg Pro Ala Val Asp Phe Met Leu Glu
    155                 160                 165

GTT CTC TAT TTG GCT TTC ATC TTC AAG ATC CCT GAA TTA ATT ACT CTC     3341
Val Leu Tyr Leu Ala Phe Ile Phe Lys Ile Pro Glu Leu Ile Thr Leu
170                 175                 180                 185

TAT CAG GTAAAACACC ATCTGCATTA AGCTATGGTT ACACATTCAT GAATATGTTC     3397
Tyr Gln

TTACTTGAGT ACTTGTATTT GTATTTCAG AGG CAC TTA TTG GAC GTT GTA GAC     3450
                               Arg His Leu Leu Asp Val Val Asp
                                           190                 195

AAA GTT GTT ATA GAG GAC ACA TTG GTT ATA CTC AAG CTT GCT AAT ATA     3498
Lys Val Val Ile Glu Asp Thr Leu Val Ile Leu Lys Leu Ala Asn Ile
                200                 205                 210

TGT GGT AAA GCT TGT ATG AAG CTA TTG GAT AGA TGT AAA GAG ATT ATT     3546
Cys Gly Lys Ala Cys Met Lys Leu Leu Asp Arg Cys Lys Glu Ile Ile
            215                 220                 225
```

-continued

```
GTC AAG TCT AAT GTA GAT ATG GTT AGT CTT GAA AAG TCA TTG CCG GAA      3594
Val Lys Ser Asn Val Asp Met Val Ser Leu Glu Lys Ser Leu Pro Glu
            230                 235                 240

GAG CTT GTT AAA GAG ATA ATT GAT AGA CGT AAA GAG CTT GGT TTG GAG      3642
Glu Leu Val Lys Glu Ile Ile Asp Arg Arg Lys Glu Leu Gly Leu Glu
        245                 250                 255

GTA CCT AAA GTA AAG AAA CAT GTC TCG AAT GTA CAT AAG GCA CTT GAC      3690
Val Pro Lys Val Lys Lys His Val Ser Asn Val His Lys Ala Leu Asp
260                 265                 270                 275

TCG GAT GAT ATT GAG TTA GTC AAG TTG CTT TTG AAA GAG GAT CAC ACC      3738
Ser Asp Asp Ile Glu Leu Val Lys Leu Leu Leu Lys Glu Asp His Thr
                280                 285                 290

AAT CTA GAT GAT GCG TGT GCT CTT CAT TTC GCT GTT GCA TAT TGC AAT      3786
Asn Leu Asp Asp Ala Cys Ala Leu His Phe Ala Val Ala Tyr Cys Asn
            295                 300                 305

GTG AAG ACC GCA ACA GAT CTT TTA AAA CTT GAT CTT GCC GAT GTC AAC      3834
Val Lys Thr Ala Thr Asp Leu Leu Lys Leu Asp Leu Ala Asp Val Asn
        310                 315                 320

CAT AGG AAT CCG AGG GGA TAT ACG GTG CTT CAT GTT GCT GCG ATG CGG      3882
His Arg Asn Pro Arg Gly Tyr Thr Val Leu His Val Ala Ala Met Arg
325                 330                 335

AAG GAG CCA CAA TTG ATA CTA TCT CTA TTG GAA AAA GGT GCA AGT GCA      3930
Lys Glu Pro Gln Leu Ile Leu Ser Leu Leu Glu Lys Gly Ala Ser Ala
340                 345                 350                 355

TCA GAA GCA ACT TTG GAA GGT AGA ACC GCA CTC ATG ATC GCA AAA CAA      3978
Ser Glu Ala Thr Leu Glu Gly Arg Thr Ala Leu Met Ile Ala Lys Gln
                360                 365                 370

GCC ACT ATG GCG GTT GAA TGT AAT AAT ATC CCG GAG CAA TGC AAG CAT      4026
Ala Thr Met Ala Val Glu Cys Asn Asn Ile Pro Glu Gln Cys Lys His
            375                 380                 385

TCT CTC AAA GGC CGA CTA TGT GTA GAA ATA CTA GAG CAA GAA GAC AAA      4074
Ser Leu Lys Gly Arg Leu Cys Val Glu Ile Leu Glu Gln Glu Asp Lys
        390                 395                 400

CGA GAA CAA ATT CCT AGA GAT GTT CCT CCC TCT TTT GCA GTG GCG GCC      4122
Arg Glu Gln Ile Pro Arg Asp Val Pro Pro Ser Phe Ala Val Ala Ala
405                 410                 415

GAT GAA TTG AAG ATG ACG CTG CTC GAT CTT GAA AAT AGA G                4162
Asp Glu Leu Lys Met Thr Leu Leu Asp Leu Glu Asn Arg
420                 425                 430

GTATCTATCA AGTCTTATTT CTTATATGTT TGAATTAAAT TTATGTCCTC TCTATTAGGA   4222

AACTGAGTGA ACTAATGATA ACTATTCTTT GTGTCGTCCA CTGTTTAG  TT GCA CTT    4278
                                                        Val Ala Leu
                                                                435

GCT CAA CGT CTT TTT CCA ACG GAA GCA CAA GCT GCA ATG GAG ATC GCC      4326
Ala Gln Arg Leu Phe Pro Thr Glu Ala Gln Ala Ala Met Glu Ile Ala
            440                 445                 450

GAA ATG AAG GGA ACA TGT GAG TTC ATA GTG ACT AGC CTC GAG CCT GAC      4374
Glu Met Lys Gly Thr Cys Glu Phe Ile Val Thr Ser Leu Glu Pro Asp
        455                 460                 465

CGT CTC ACT GGT ACG AAG AGA ACA TCA CCG GGT GTA AAG ATA GCA CCT      4422
Arg Leu Thr Gly Thr Lys Arg Thr Ser Pro Gly Val Lys Ile Ala Pro
                470                 475                 480

TTC AGA ATC CTA GAA GAG CAT CAA AGT AGA CTA AAA GCG CTT TCT AAA      4470
Phe Arg Ile Leu Glu Glu His Gln Ser Arg Leu Lys Ala Leu Ser Lys
            485                 490                 495

ACC G GTATGGATTC TCACCCACTT CATCGGACTC CTTATCACAA AAAACAAAAC         4524
Thr
500

TAAATGATCT TTAAACATGG TTTTGTTACT TGCTGTCTGA CCTTGTTTTT TTTATCATCA   4584
```

```
G  TG GAA CTC GGG AAA CGA TTC TTC CCG CGC TGT TCG GCA GTG CTC      4629
   Val Glu Leu Gly Lys Arg Phe Phe Pro Arg Cys Ser Ala Val Leu
                505                 510                 515

GAC CAG ATT ATG AAC TGT GAG GAC TTG ACT CAA CTG GCT TGC GGA GAA    4677
Asp Gln Ile Met Asn Cys Glu Asp Leu Thr Gln Leu Ala Cys Gly Glu
                520                 525                 530

GAC GAC ACT GCT GAG AAA CGA CTA CAA AAG AAG CAA AGG TAC ATG GAA    4725
Asp Asp Thr Ala Glu Lys Arg Leu Gln Lys Lys Gln Arg Tyr Met Glu
                535                 540                 545

ATA CAA GAG ACA CTA AAG AAG GCC TTT AGT GAG GAC AAT TTG GAA TTA    4773
Ile Gln Glu Thr Leu Lys Lys Ala Phe Ser Glu Asp Asn Leu Glu Leu
                550                 555                 560

GGA AAT TCG TCC CTG ACA GAT TCG ACT TCT TCC ACA TCG AAA TCA ACC    4821
Gly Asn Ser Ser Leu Thr Asp Ser Thr Ser Ser Thr Ser Lys Ser Thr
                565                 570                 575

GGT GGA AAG AGG TCT AAC CGT AAA CTC TCT CAT CGT CGT CGG TGA        4866
Gly Gly Lys Arg Ser Asn Arg Lys Leu Ser His Arg Arg Arg  *
580                 585                 590

GACTCTTGCC TCTTAGTGTA ATTTTTGCTG TACCATATAA TTCTGTTTTC ATGATGACTG   4926

TAACTGTTTA TGTCTATCGT TGGCGTCATA TAGTTTCGCT CTTCGTTTTG CATCCTGTGT   4986

ATTATTGCTG CAGGTGTGCT TCAAACAAAT GTTGTAACAA TTTGAACCAA TGGTATACAG   5046

ATTTGTAATA TATATTTATG TACATCAACA ATAACCCATG ATGGTGTTAC AGAGTTGCTA   5106

GAATCAAAGT GTGAAATAAT GTCAAATTGT TCATCTGTTG GATATTTTCC ACCAAGAACC   5166

AAAAGAATAT TCAAGTTCCC TGAACTTCTG GCAACATTCA TGTTATATGT ATCTTCCTAA   5226

TTCTTCCTTT AACCTTTTGT AACTCGAATT ACACAGCAAG TTAGTTTCAG GTCTAGAGAT   5286

AAGAGAACAC TGAGTGGGCG TGTAAGGTGC ATTCTCCTAG TCAGCTCCAT TGCATCCAAC   5346

ATTTGTGAAT GACACAAGTT AACAATCCTT TGCACCATTT CTGGGTGCAT ACATGGAAAC   5406

TTCTTCGATT GAAACTTCCC ACATGTGCAG GTGCGTTCGC TGTCACTGAT AGACCAAGAG   5466

ACTGAAAGCT TTCACAAATT GCCCTCAAAT CTTCTGTTTC TATCGTCATG ACTCCATATC   5526

TCCGACCACT GGTCATGAGC CAGAGCCCAC TGATTTTGAG GGAATTGGGC TAACCATTTC   5586

CGAGCTTCTG AGTCCTTCTT TTTGATGTCC TTTATGTAGG AATCAAATTC TTCCTTCTGA   5646

CTTGTGGAT                                                          5655

(2) INFORMATION FOR SEQ ID NO:3:

(i) SEQUENCE CHARACTERISTICS:
        (A) LENGTH:  593 amino acids
        (B) TYPE: amino acid
        (D) TOPOLOGY: linear (ii) MOLECULE TYPE: protein (xi) SEQUENCE DESCRIPTION: SEQ ID NO:3:

Met Asp Thr Thr Ile Asp Gly Phe Ala Asp Ser Tyr Glu Ile Ser Ser
     1               5                  10                  15

Thr Ser Phe Val Ala Thr Asp Asn Thr Asp Ser Ser Ile Val Tyr Leu
                    20                  25                  30

Ala Ala Glu Gln Val Leu Thr Gly Pro Asp Val Ser Ala Leu Gln Leu
                35                  40                  45

Leu Ser Asn Ser Phe Glu Ser Val Phe Asp Ser Pro Asp Asp Phe Tyr
            50                  55                  60

Ser Asp Ala Lys Leu Val Leu Ser Asp Gly Arg Glu Val Ser Phe His
     65                 70                  75                  80
```

```
Arg Cys Val Leu Ser Ala Arg Ser Ser Phe Lys Ser Ala Leu Ala
                85                  90                  95

Ala Ala Lys Lys Glu Lys Asp Ser Asn Asn Thr Ala Ala Val Lys Leu
            100                 105                 110

Glu Leu Lys Glu Ile Ala Lys Asp Tyr Glu Val Gly Phe Asp Ser Val
            115                 120                 125

Val Thr Val Leu Ala Tyr Val Tyr Ser Ser Arg Val Arg Pro Pro Pro
    130                 135                 140

Lys Gly Val Ser Glu Cys Ala Asp Glu Asn Cys Cys His Val Ala Cys
145                 150                 155                 160

Arg Pro Ala Val Asp Phe Met Leu Glu Val Leu Tyr Leu Ala Phe Ile
                165                 170                 175

Phe Lys Ile Pro Glu Leu Ile Thr Leu Tyr Gln Arg His Leu Leu Asp
                180                 185                 190

Val Val Asp Lys Val Val Ile Glu Asp Thr Leu Val Ile Leu Lys Leu
                195                 200                 205

Ala Asn Ile Cys Gly Lys Ala Cys Met Lys Leu Leu Asp Arg Cys Lys
                210                 215                 220

Glu Ile Ile Val Lys Ser Asn Val Asp Met Val Ser Leu Glu Lys Ser
225                 230                 235                 240

Leu Pro Glu Glu Leu Val Lys Glu Ile Ile Asp Arg Arg Lys Glu Leu
                245                 250                 255

Gly Leu Glu Val Pro Lys Val Lys Lys His Val Ser Asn Val His Lys
                260                 265                 270

Ala Leu Asp Ser Asp Asp Ile Glu Leu Val Lys Leu Leu Leu Lys Glu
                275                 280                 285

Asp His Thr Asn Leu Asp Asp Ala Cys Ala Leu His Phe Ala Val Ala
                290                 295                 300

Tyr Cys Asn Val Lys Thr Ala Thr Asp Leu Leu Lys Leu Asp Leu Ala
305                 310                 315                 320

Asp Val Asn His Arg Asn Pro Arg Gly Tyr Thr Val Leu His Val Ala
                325                 330                 335

Ala Met Arg Lys Glu Pro Gln Leu Ile Leu Ser Leu Leu Glu Lys Gly
                340                 345                 350

Ala Ser Ala Ser Glu Ala Thr Leu Glu Gly Arg Thr Ala Leu Met Ile
                355                 360                 365

Ala Lys Gln Ala Thr Met Ala Val Glu Cys Asn Asn Ile Pro Glu Gln
                370                 375                 380

Cys Lys His Ser Leu Lys Gly Arg Leu Cys Val Glu Ile Leu Glu Gln
385                 390                 395                 400

Glu Asp Lys Arg Glu Gln Ile Pro Arg Asp Val Pro Pro Ser Phe Ala
                405                 410                 415

Val Ala Ala Asp Glu Leu Lys Met Thr Leu Leu Asp Leu Glu Asn Arg
                420                 425                 430

Val Ala Leu Ala Gln Arg Leu Phe Pro Thr Glu Ala Gln Ala Ala Met
                435                 440                 445

Glu Ile Ala Glu Met Lys Gly Thr Cys Glu Phe Ile Val Thr Ser Leu
450                 455                 460

Glu Pro Asp Arg Leu Thr Gly Thr Lys Arg Thr Ser Pro Gly Val Lys
465                 470                 475                 480

Ile Ala Pro Phe Arg Ile Leu Glu Glu His Gln Ser Arg Leu Lys Ala
                485                 490                 495
```

-continued

```
Leu Ser Lys Thr Val Glu Leu Gly Lys Arg Phe Phe Pro Arg Cys Ser
            500                 505                 510

Ala Val Leu Asp Gln Ile Met Asn Cys Glu Asp Leu Thr Gln Leu Ala
            515                 520                 525

Cys Gly Glu Asp Asp Thr Ala Glu Lys Arg Leu Gln Lys Lys Gln Arg
            530                 535                 540

Tyr Met Glu Ile Gln Glu Thr Leu Lys Lys Ala Phe Ser Glu Asp Asn
545                 550                 555                 560

Leu Glu Leu Gly Asn Ser Ser Leu Thr Asp Ser Thr Ser Ser Thr Ser
                    565                 570                 575

Lys Ser Thr Gly Gly Lys Arg Ser Asn Arg Lys Leu Ser His Arg Arg
            580                 585                 590

Arg
```

(2) INFORMATION FOR SEQ ID NO:4:

(i) SEQUENCE CHARACTERISTICS:
        (A) LENGTH: 41 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:4:

```
Ile Arg Arg Met Arg Arg Ala Leu Asp Ala Ala Asp Ile Glu Leu Val
1               5                   10                  15

Lys Leu Met Val Met Gly Glu Gly Leu Asp Leu Asp Ala Leu Ala
                20                  25                  30

Val His Tyr Ala Val Gln His Cys Asn
            35                  40
```

(2) INFORMATION FOR SEQ ID NO:5:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:5:

```
Pro Thr Gly Lys Thr Ala Leu His Leu Ala Ala Glu Met Val Ser Pro
1               5                   10                  15

Asp Met Val Ser Val Leu Leu Asp His His Ala Asp Xaa Asn Phe Arg
                20                  25                  30

Thr Xaa Asp Gly Val Thr
            35
```

(2) INFORMATION FOR SEQ ID NO:6:

(i) SEQUENCE CHARACTERISTICS:
        (A) LENGTH: 41 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:6:

```
Ile Arg Arg Met Arg Arg Ala Leu Asp Ala Ala Asp Ile Glu Leu Val
1               5                   10                  15
```

-continued

```
    Lys Leu Met Val Met Gly Glu Gly Leu Asp Leu Asp Asp Ala Leu Ala
                 20                  25                  30

Val His Tyr Ala Val Gln His Cys Asn
                 35                  40
```

(2) INFORMATION FOR SEQ ID NO:7:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:7:

```
    Arg Arg Pro Asp Ser Lys Thr Ala Leu His Leu Ala Ala Glu Met Val
    1               5                  10                  15

Ser Pro Asp Met Val Ser Val Leu Leu Asp Gln
                 20                  25
```

(2) INFORMATION FOR SEQ ID NO:8:

(i) SEQUENCE CHARACTERISTICS:
        (A) LENGTH: 41 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:8:

```
    Ile Arg Arg Met Arg Arg Ala Leu Asp Ala Ala Asp Ile Glu Leu Val
    1               5                  10                  15

Lys Leu Met Val Met Gly Glu Gly Leu Asp Leu Asp Asp Ala Leu Ala
                 20                  25                  30

Val His Tyr Ala Val Gln His Cys Asn
                 35                  40
```

(2) INFORMATION FOR SEQ ID NO:9:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:9:

```
    Arg Arg Pro Asp Ser Lys Thr Ala Leu His Leu Ala Ala Glu Met Val
    1               5                  10                  15

Ser Pro Asp Met Val Ser Val Leu Leu Asp Gln
                 20                  25
```

(2) INFORMATION FOR SEQ ID NO:10:

(i) SEQUENCE CHARACTERISTICS:
        (A) LENGTH: 41 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:10:

```
    Ile Arg Arg Met Arg Arg Ala Leu Asp Ala Ala Asp Ile Glu Leu Val
    1               5                   10                  15

Lys Leu Met Val Met Gly Glu Gly Leu Asp Leu Asp Asp Ala Leu Ala
                    20                  25                  30

Val His Tyr Ala Val Gln His Cys Asn
                    35                  40
```

(2) INFORMATION FOR SEQ ID NO:11:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:11:

```
    Pro Thr Gly Lys Thr Ala Leu His Leu Ala Ala Glu Met Val Ser Pro
    1               5                   10                  15

Asp Met Val
```

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:12:

AATTCTAAAG CATGCCGATC GG                                          22

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:13:

AATTCCGATC GGCATGCTTT A                                           21

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:14:

AATTCTAAAC CATGGCGATC GG                                          22

(2) INFORMATION FOR SEQ ID NO:15:

-continued

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:15:

AATTCCGATC GCCATGGTTT A                                              21

(2) INFORMATION FOR SEQ ID NO:16:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:16:

CCAGCTGGAA TTCCG                                                     15

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:17:

CGGAATTCCA GCTGGCATG                                                 19
```

GENE ENCODING A PROTEIN INVOLVED IN THE SIGNAL TRANSDUCTION CASCADE LEADING TO SYSTEMIC ACQUIRED RESISTANCE IN PLANTS

This application claims the benefit of U.S. Provisional Application No. 60/020,272, filed Jun. 21, 1996; U.S. Provisional Application No. 60/024,883, filed Aug. 30, 1996; U.S. Provisional Application No. 60/033,177, filed Dec. 13, 1996; U.S. Provisional Application No. 60/034,379, filed Dec. 27, 1996; U.S. Provisional Application No. 60/034,730, filed Jan. 10, 1997; and U.S. Provisional Application No. 60/035,022, filed Jan. 10, 1997. The disclosures of each of these U.S. Provisional Applications are hereby expressly incorporated by reference in their entireties into the instant disclosure.

FIELD OF THE INVENTION

The present invention relates to broad-spectrum disease resistance in plants, including the phenomenon of systemic acquired resistance (SAR). More particularly, the present invention relates to the identification, isolation and characterization of a gene involved in the signal transduction cascade leading to systemic acquired resistance.

BACKGROUND OF THE INVENTION

Plants are constantly challenged by a wide variety of pathogenic organisms including viruses, bacteria, fungi, and nematodes. Crop plants are particularly vulnerable because they are usually grown as genetically-uniform monocultures; when disease strikes, losses can be severe. However, most plants have their own innate mechanisms of defense against pathogenic organisms. Natural variation for resistance to plant pathogens has been identified by plant breeders and pathologists and bred into many crop plants. These natural disease resistance genes often provide high levels of resistance to or immunity against pathogens.

Systemic acquired resistance (SAR) is one component of the complex system plants use to defend themselves from pathogens (Hunt and Ryals 1996; Ryals et al., 1996). SAR is a particularly important aspect of plant-pathogen responses because it is a pathogen-inducible, systemic resistance against a broad spectrum of infectious agents, including viruses, bacteria, and fungi. When the SAR signal transduction pathway is blocked, plants become more susceptible to pathogens that normally cause disease, and they also become susceptible to some infectious agents that would not normally cause disease (Gaffney et al., 1993; Delaney et al., 1994, 1995; 1993; Bi et al., 1995; Mauch-Mani and Slusarenko 1996; Delaney 1997). These observations indicate that the SAR signal transduction pathway is critical for maintaining plant health.

Conceptually, the SAR response can be divided into two phases. In the initiation phase, a pathogen infection is recognized, and a signal is released that travels through the phloem to distant tissues. This systemic signal is perceived by target cells, which react by expression of both SAR genes and disease resistance. The maintenance phase of SAR refers to the period of time, from weeks up to the entire life of the plant, during which the plant is in a quasi steady state, and disease resistance is maintained (Ryals et al., 1996).

Salicylic acid (SA) accumulation appears to be required for SAR signal transduction. Plants that cannot accumulate SA due to treatment with specific inhibitors, epigenetic repression of phenylalanine ammonia-lyase, or transgenic expression of salicylate hydroxylase, which specifically degrades SA, also cannot induce either SAR gene expression or disease resistance (Gaffney et al., 1993; Delaney et al., 1994; Maher et al., 1994; Mauch-Mani and Slusarenko 1996; Pallas et al., 1996). See also, U.S. patent application Ser. No. 08/454,876, incorporated herein by reference in its entirety). Although it has been suggested that SA might serve as the systemic signal, this is currently controversial and, to date, all that is known for certain is that if SA cannot accumulate, then SAR signal transduction is blocked (Pallas et al., 1996; Shulaev et al., 1995; Vernooij et al., 1994).

Recently, Arabidopsis has emerged as a model system to study SAR (Uknes et al., 1992; Uknes et al., 1993; Cameron et al., 1994; Mauch-Mani and Slusarenko 1994; Dempsey and Klessig 1995). It has been demonstrated that SAR can be activated in Arabidopsis by both pathogens and chemicals, such as SA, 2,6-dichloroisonicotinic acid (INA) and benzo(1,2,3)thiadiazole-7-carbothioic acid S-methyl ester (BTH) (Uknes et al., 1992; Vernooij et al., 1995; Lawton et al., 1996). Following treatment with either INA or BTH or pathogen infection, at least three pathogenesis-related (PR) protein genes, namely, PR-1, PR-2, and PR-5 are coordinately induced concomitant with the onset of resistance (Uknes et al., 1992, 1993). In tobacco, the best characterized species, treatment with a pathogen or an immunization compound induces the expression of at least nine sets of genes (Ward et al., 1991).

A number of Arabidopsis mutants have been isolated that have modified SAR signal transduction. The first of these mutants are the so-called lsd (lesions simulating disease) mutants and acd2 (accelerated cell death) (Dietrich et al., 1994; Greenberg et al., 1994). These mutants all have some degree of spontaneous necrotic lesion formation on their leaves, elevated levels of SA, mRNA accumulation for the SAR genes, and significantly enhanced disease resistance. At least seven different lsd mutants have been isolated and characterized (Dietrich et al., 1994; Weymann et al., 1995). Another interesting class of mutants are cim (constitutive immunity) mutants (Lawton et al., 1993; Steiner et al., 1996). See also, U.S. patent application Ser. No. 08/648,949, filed May 16, 1996, hereby incorporated by reference into the instant disclosure in its entirety. Like lsd mutants and acd2, cim mutants have elevated SA and SAR gene expression and resistance, but in contrast to lsd or acd2, do not display detectable lesions on their leaves. cpr1 (constitutive expresser of PR genes) may be a type of cim mutant; however, because the presence of microscopic lesions on the leaves of cpr1 has not been ruled out, cpr1 might be a type of lsd mutant (Bowling et al., 1994).

Mutants have also been isolated that are blocked in SAR signaling. ndr1 (non-race-specific disease resistance) is a mutant that allows growth of both *Pseudomonas syringae* containing various avirulence genes and also normally avirulent isolates of *Peronospora parasitica* (Century et al., 1995). Apparently this mutant is blocked early in SAR signaling.

Despite much research and the use of sophisticated and intensive crop-protection measures, including genetic transformation of plants, losses due to disease remain in the billions of dollars annually. Disease resistance genes have previously been cloned but transgenic plants transformed with these genes are typically resistant only to a subset of strains of a particular pathogen species. Despite efforts to clone genes involved in SAR, a gene controlling broad spectrum disease resistance has not until now been isolated and characterized.

SUMMARY OF THE INVENTION

The present invention concerns the identification, isolation, and characterization of the NIM1 gene, which encodes a protein involved in the signal transduction cascade responsive to biological and chemical inducers that leads to systemic acquired resistance in plants.

Hence, the present invention is directed to an isolated DNA molecule (NIM1 gene) that encodes a NIM1 protein involved in the signal transduction cascade leading to systemic acquired resistance in plants.

In one preferred embodiment, the DNA molecule that encodes the NIM1 protein hybridizes under the following conditions to clone BAC-04, ATCC Deposit No. 97543: hybridization in 1% BSA; 520 mM $NaPO_4$, pH 7.2; 7% lauryl sulfate, sodium salt; 1 mM EDTA; 250 mM sodium chloride at 55° C. for 18–24 h, and wash in 6 XSSC for 15 min. (X3) 3 XSSC for 15 min. (X1) at 55° C. In an especially preferred embodiment, the NIM1 gene is comprised within clone BAC-04, ATCC Deposit No. 97543.

In another embodiment, the DNA molecule that encodes the NIM1 protein hybridizes under the following conditions to cosmid D7, ATCC Deposit No. 97736: hybridization in 1% BSA; 520 mM $NaPO_4$, pH 7.2; 7% lauryl sulfate, sodium salt; 1 mM EDTA; 250 mM sodium chloride at 55° C. for 18–24 h, and wash in 6 XSSC for 15 min. (X3) 3 XSSC for 15 min. (X1) at 55° C. In an especially preferred embodiment, the NIM1 gene is comprised within cosmid D7, ATCC Deposit No. 97736.

The NIM1 gene of the invention may be isolated from a dicotyledonous plant such as Arabidopsis, tobacco, cucumber, or tomato. Alternately, the NIM1 gene may be isolated from a monocotyledonous plant such as maize, wheat, or barley.

In yet another embodiment, the encoded NIM1 protein comprises the amino acid sequence set forth in SEQ ID NO: 3. In still another embodiment, the NIM1 gene coding sequence hybridizes under the following conditions to the coding sequence set forth in SEQ ID NO: 2: hybridization in 1% BSA; 520 mM $NaPO_4$, pH 7.2; 7% lauryl sulfate, sodium salt; 1 mM EDTA; 250 mM sodium chloride at 55° C. for 18–24 h, and wash in 6 XSSC for 15 min. (X3) 3 XSSC for 15 min. (X1) at 55° C. In an especially preferred embodiment, the NIM1 gene coding sequence comprises the coding sequence set forth in SEQ ID NO:2.

The present invention also encompasses a chimeric gene comprising a promoter active in plants operatively linked to a NIM1 gene coding sequence, a recombinant vector comprising such a chimeric gene, wherein the vector is capable of being stably transformed into a host, as well as a host stably transformed with such a vector. Preferably, the host is a plant such as one of the following agronomically important crops: rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

In an especially preferred embodiment, the NIM1 protein is expressed in a transformed plant at higher levels than in a wild type plant.

The present invention is also directed to a method of conferring a CIM phenotype to a plant by transforming the plant with a recombinant vector comprising a chimeric gene that itself comprises a promoter active in plants operatively linked to a NIM1 gene coding sequence, wherein the encoded NIM1 protein is expressed in the transformed plant at higher levels than in a wild type plant.

Further, the present invention is directed to a method of activating systemic acquired resistance in a plant by transforming the plant with a recombinant vector comprising a chimeric gene that itself comprises a promoter active in plants operatively linked to a NIM1 gene coding sequence, wherein the encoded NIM1 protein is expressed in the transformed plant at higher levels than in a wild type plant.

In addition, the present invention is directed to a method of conferring broad spectrum disease resistance to a plant by transforming the plant with a recombinant vector comprising a chimeric gene that itself comprises a promoter active in plants operatively linked to a NIM1 gene coding sequence, wherein the encoded NIM1 protein is expressed in the transformed plant at higher levels than in a wild type plant.

In yet another aspect, the present invention is directed to a method of screening for a NIM1 gene involved in the signal transduction cascade leading to systemic acquired resistance in a plant, comprising probing a genomic or cDNA library from said plant with a NIM1 coding sequence that hybridizes under the following set of conditions to the coding sequence set forth in SEQ ID NO:2: hybridization in 1% BSA; 520 mM $NaPO_4$, pH 7.2; 7%; lauryl sulfate, sodium salt; 1 mM EDTA; 250 mM sodium chloride at 55° C. for 18–24 h, and wash in 6 XSSC for 15 min. (X3) 3 XSSC for 15 min. (X1) at 55° C.

(A) Map position of NIM1 on chromosome 1. The total number of gametes scored is 2276.

(B) Yeast artificial chromosome (striped), bacterial artificial chromosome (BAC), and P1 clones used to clone NIM1.

(C) Cosmid clones that cover the NIM1 locus. The three cosmids that complement nim1-1 are shown as thicker lines.

(D) The four putative gene regions on the smallest fragment of complementing genomic DNA. The four open reading frames that comprise the NIM1 gene are indicated by the open bars. The arrows indicate the direction of transcription. Numbering is relative to the first base of Arabidopsis genomic DNA present in cosmid D7.

FIG. 6 shows the nucleic acid sequence of the NIM1 gene and the amino acid sequence of the NIM1 gene product, including changes in the various alleles. This nucleic acid sequence, which is on the opposite strand as the 9.9 kb sequence presented in SEQ ID NO:1, is also presented in SEQ ID NO:2, and the amino acid sequence of the NIM1 gene product is also presented in SEQ ID NO:3.

Figure 7:
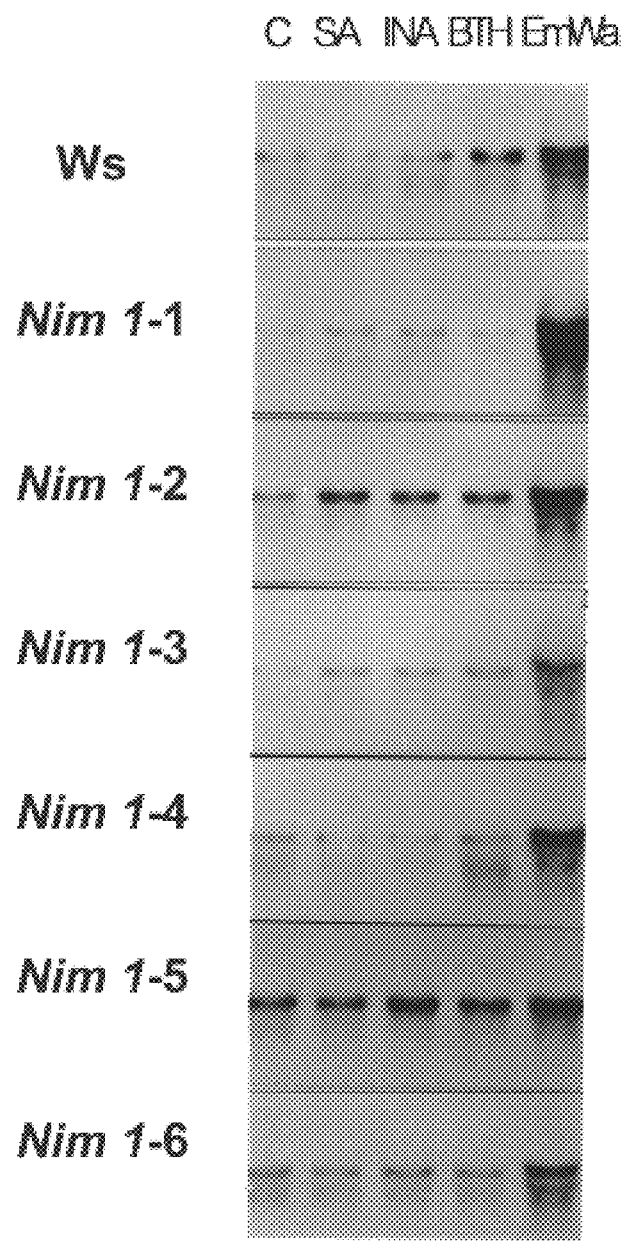

FIG. 7 shows the accumulation of NIM1 induced by INA, BTH, SA and pathogen treatment in wild type plants and mutant alleles of nim1. The RNA gel blots in FIG. 3 were probed for expression of RNA by using a probe derived from 2081 to 3266 in the sequence shown in FIG. 6.

FIG. 8 is an amino acid sequence comparison of Expressed Sequence Tag regions of the NIM1 protein and cDNA protein products of 4 rice gene sequences.

BRIEF DESCRIPTION OF THE SEQUENCES IN THE SEQUENCE LISTING

Figure 5A:
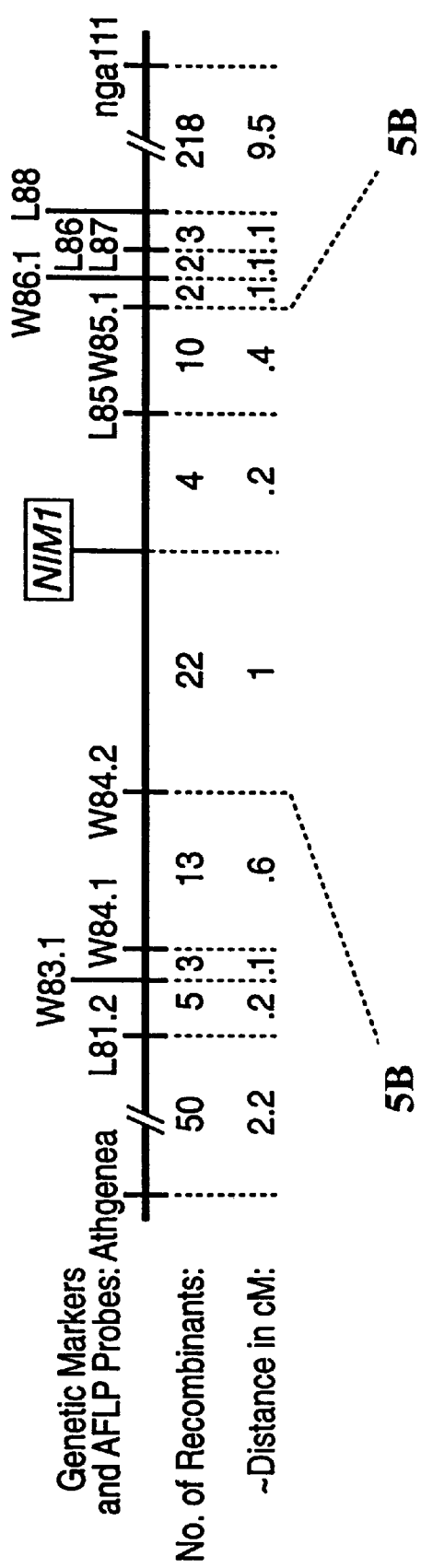
FIGS. 5A–5D present a global map at increasing levels of resolution of the chromosomal region centered on NIM1 with recombinants indicated, including, BACs, YACs and Cosmids in NIM1 region.
Figure 5B:
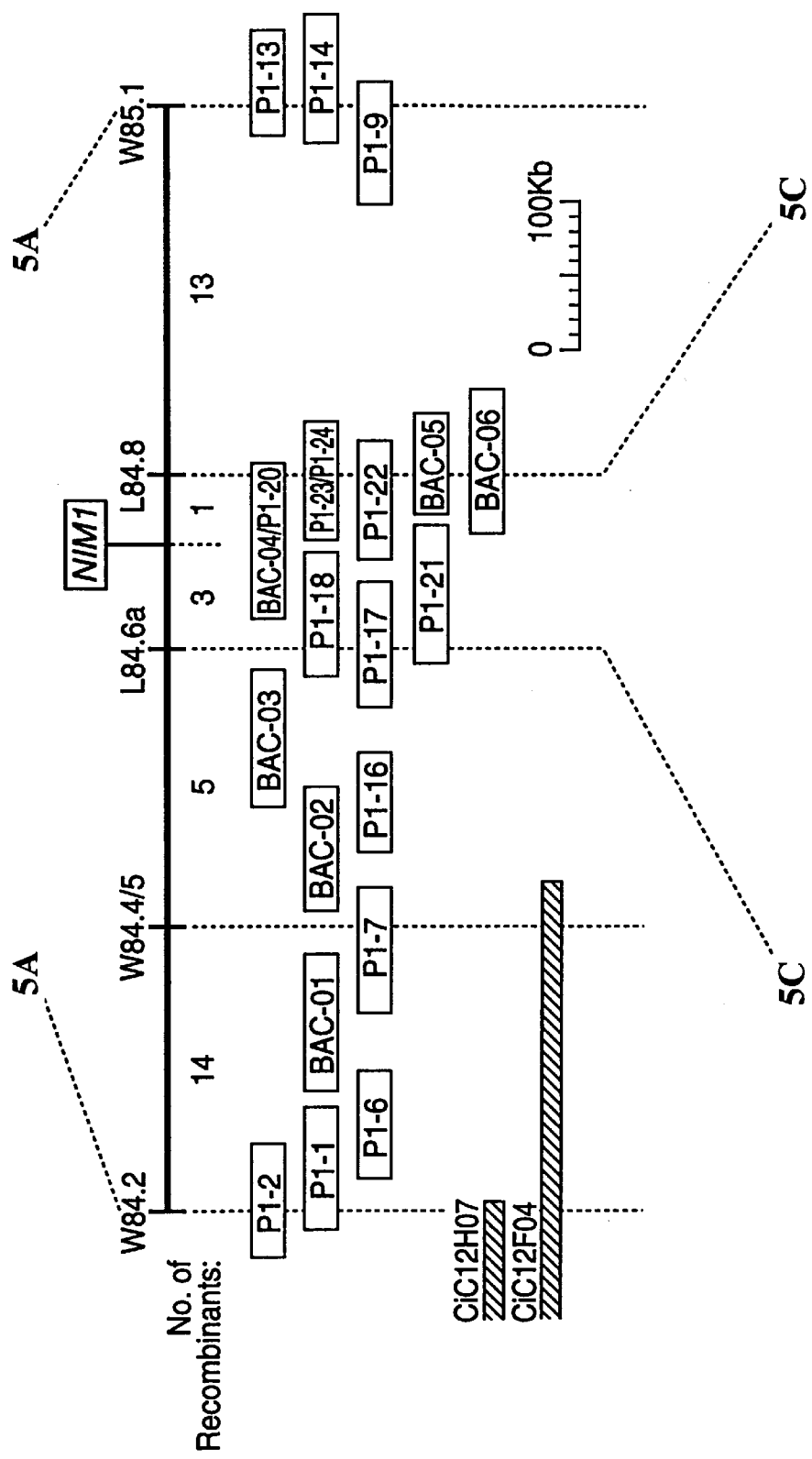
Figure 5C:
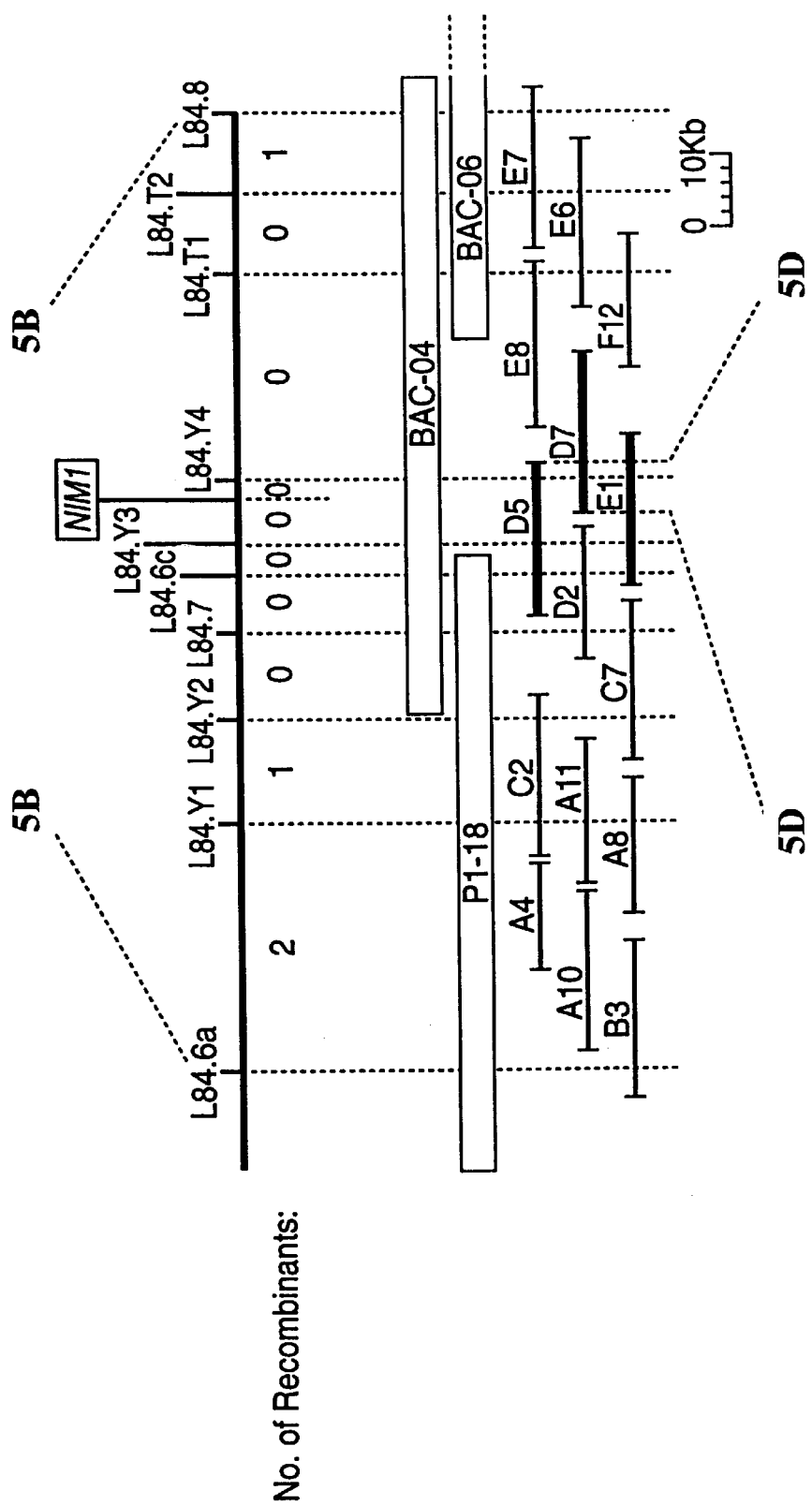
Figure 5D:
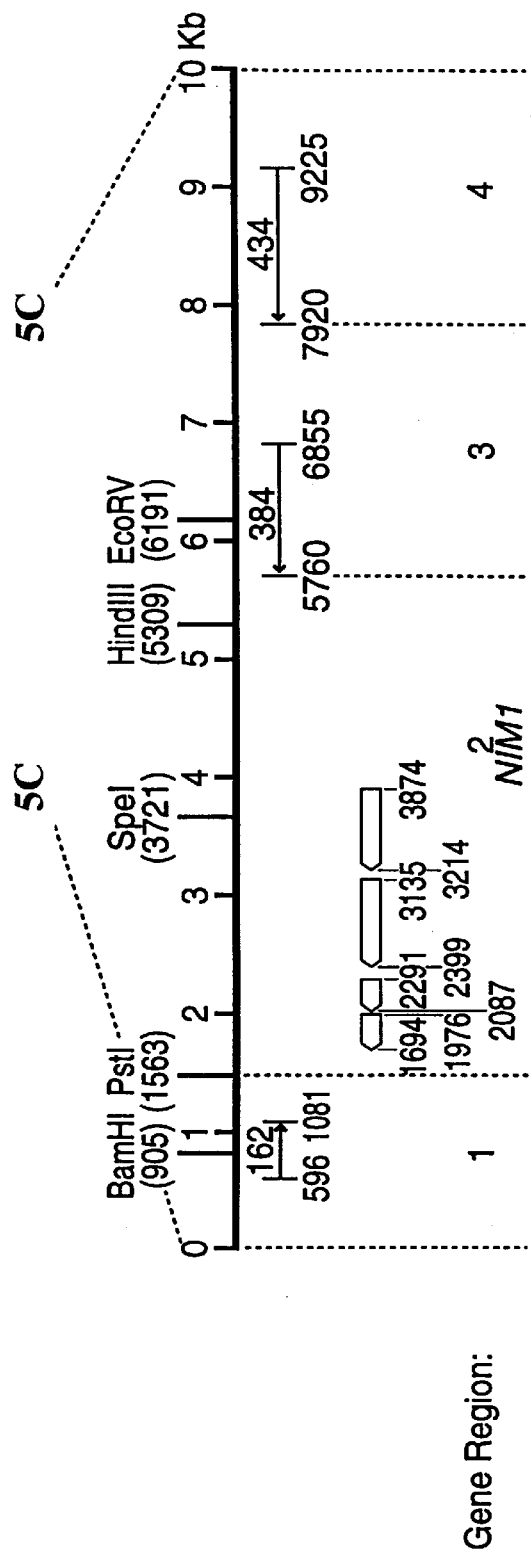

SEQ ID NO:1—9919-bp genomic sequence of NIM1 gene region 2 in FIG. 5D.

SEQ ID NO:2—5655-bp genomic sequence in FIG. 6 (opposite strand from SEQ ID NO: 1).

SEQ ID NO:3—AA sequence of wild-type NIM1 protein encoded by cds of SEQ ID NO:2.

SEQ ID NO:4—Rice-1 AA sequence 33-155 from FIG. 8.

SEQ ID NO:5—Rice-1 AA sequence 215-328 from FIG. 8.

SEQ ID NO:6—Rice-2 AA sequence 33-155 from FIG. 8.

SEQ ID NO:7—Rice-2 AA sequence 208-288 from FIG. 8.

SEQ ID NO:8—Rice-3 AA sequence 33-155 from FIG. 8.

SEQ ID NO:9—Rice-3 AA sequence 208-288 from FIG. 8.

SEQ ID NO:10—Rice-4 AA sequence 33-155 from FIG. 8.

SEQ ID NO:11—Rice-4 AA sequence 215-271 from FIG. 8.

SEQ ID NO:12—Oligonucleotide.

SEQ ID NO:13—Oligonucleotide.

SEQ ID NO:14—Oligonucleotide.

SEQ ID NO:15—Oligonucleotide.

SEQ ID NO:16—Oligonucleotide.

SEQ ID NO:17—Oligonucleotide.

DETAILED DESCRIPTION OF THE INVENTION

Definitions

| | |
|---|---|
| acd: | accelerated cell death mutant plant |
| AFLP: | Amplified Fragment Length Polymorphism |
| avrRpt2: | avirulence gene Rpt2, isolated from *Pseudomonas syringae* |
| BAC: | Bacterial Artificial Chromosome |
| BTH: | benzo(1,2,3)thiadiazole-7-carbothioic acid S-methyl ester |
| CIM: | Constitutive IMmunity phenotype (SAR is constitutively activated) |
| cim: | constitutive immunity mutant plant |
| cM: | centimorgans |
| cpr1: | constitutive expresser of PR genes mutant plant |
| Col-O: | Arabidopsis ecotype Columbia |
| ECs: | Enzyme combinations |
| Emwa: | *Peronospora parasitica* isolate compatible in the Ws-O ecotype of Arabidopsis |
| EMS: | ethyl methane sulfonate |
| INA: | 2,6-dichloroisonicotinic acid |
| Ler: | Arabidopsis ecotype *Landsberg erecta* |
| lsd: | lesions simulating disease mutant plant |
| nahG: | salicylate hydroxylase *Pseudomonas putida* that converts salicylic acid to catechol |
| NahG: | Arabidopsis line transformed with nahG gene |
| ndr: | non-race-specific disease resistance mutant plant |
| nim: | non-inducible immunity mutant plant |
| NIM1: | the wild type gene, involved in the SAR signal transduction cascade |
| NIM1: | Protein encoded by the wild type NIM1 gene |
| nim1: | mutant allele of NIM1, conferring disease susceptibility to the plant; also refers to mutant *Arabidopsis thaliana* plants having the nim1 mutant allele of NIM1 |
| Noco: | *Peronospora parasitica* isolate compatible in the Col-O ecotype of Arabidopsis |
| ORF: | open reading frame |
| PCs: | Primer combinations |
| PR: | Pathogenesis Related |
| SA: | salicylic acid |
| SAR: | Systemic Acquired Resistance |
| SSLP: | Simple Sequence Length Polymorphism |
| UDS: | Universal Disease Susceptible phenotype |
| Wela: | *Peronospora parasitica* isolate compatible in the Weiningen ecotype of Arabidopsis |
| Ws-O: | Arabidopsis ecotype Issilewskija |
| WT: | wild type |
| YAC: | Yeast Artificial Chromosome |

The nim Mutant Phenotype

The present invention relates to mutant plants, as well as genes isolated therefrom, which are defective in their normal response to pathogen infection in that they do not express genes associated with SAR. These mutants are referred to as nim mutants (for non-inducible immunity) and are "universal disease susceptible" (UDS) by virtue of their being susceptible to many strains and pathotypes of pathogens of the host plant and also to pathogens that do not normally infect the host plant, but that normally infect other hosts. Such mutants can be selected by treating seeds or other biological material with mutagenic agents and then selecting progeny plants for the UDS phenotype by treating progeny plants with known chemical inducers (e.g. INA) of SAR and then infecting the plants with a known pathogen. Non-inducible mutants develop severe disease symptoms under these circumstances, whereas wild type plants are induced by the chemical compound to systemic acquired resistance. nim mutants can be equally selected from mutant populations generated by chemical and irradiation mutagenesis, as well as from populations generated by T-DNA insertion and transposon-induced mutagenesis. Techniques of generating mutant plant lines are well known in the art.

nim mutants provide useful indicators of the evaluation of disease pressure in field pathogenesis tests where the natural resistance phenotype of so-called wild type (i.e. non-mutant) plants may vary and therefore not provide a reliable standard of susceptibility. Furthermore, nim plants have additional utility for the testing of candidate disease resistance transgenes. Using a nim stock line as a recipient for transgenes, the contribution of the transgene to disease resistance is directly assessable over a base level of susceptibility. Furthermore, the nim plants are useful as a tool in the understanding of plant-pathogen interactions. nim host plants do not mount a systemic response to pathogen attack, and the unabated development of the pathogen is an ideal system in which to study its biological interaction with the host.

As nim host plants may also be susceptible to pathogens outside of the host-range they normally fall, these plants also have significant utility in the molecular, genetic, and biological study of host-pathogen interactions. Furthermore, the UDS phenotype of nim plants also renders them of utility for fungicide screening. nim mutants selected in a particular host have considerable utility for the screening of fungicides using that host and pathogens of the host. The advantage lies in the UDS phenotype of the mutant, which circumvents the problems encountered by hosts being differentially susceptible to different pathogens and pathotypes, or even resistant to some pathogens or pathotypes.

nim mutants have further utility for the screening of fungicides against a range of pathogens and pathotypes using a heterologous host, i.e. a host that may not normally be within the host species range of a particular pathogen. Thus, the susceptibility of nim mutants of Arabidopsis to pathogens of other species (e.g. crop plant species) facilitates efficacious fungicide screening procedures for compounds against important pathogens of crop plants.

The *Arabidopsis thaliana* nim1 Mutant

An *Arabidopsis thaliana* mutant called nim1 (noninducible immunity) that supports *P. parasitica* (i.e., causal agent of downy mildew disease) growth following INA treatment is described in Delaney et al., 1995. Although nim1 can accumulate SA following pathogen infection, neither SAR gene expression nor disease resistance can be induced, suggesting that the mutation blocks the pathway downstream of SA. nim1 is also impaired in its ability to respond to INA or BTH, suggesting that the block exists downstream of the action of these chemicals (Delaney et al., 1995; Lawton et al., 1996). This first Arabidopsis nim1 mutant (herein designated nim1-1) was isolated from 80,000 plants of a T-DNA tagged Arabidopsis ecotype Issilewskija (Ws-0) population to by spraying two week old plants with 0.33 mM INA followed by inoculation with *P. parasitica* (Delaney et al., 1995). Plants that supported fungal growth after INA treatment were selected as putative mutants. Five additional mutants (herein designated nim1-2, nim1-3, nim1-4, nim1-5, and nim1-6) were isolated from 280,000 $M_2$ plants from an ethyl methanesulfonate (EMS)-mutagenized Ws-0 population.

To determine whether the mutants were dominant or recessive, Ws-0 plants were used as pollen donors to cross to each of these mutants. The $F_1$ plants were then scored for their ability to support fungal growth following INA treatment. As shown in Table 3 of the Examples, all nim1-1, nim1-2, nim1-3, nim1-4, and nim1-6 $F_1$ plants were phenotypically wild type, indicating a recessive mutation in each line. nim1-5 showed the nim phenotype in all 35 $F_1$ plants, indicating that this particular mutant is dominant. For verification, the reciprocal cross was carried out using nim1-5 as the pollen donor to fertilize Ws-0 plants. In this case, all 18 $F_1$ plants were phenotypically nim, confirming the dominance of the nim1-5 mutation.

To determine whether the nim1-2 through nim1-6 mutations were allelic to the previously characterized nim1-1 mutation, pollen from nim1-1 was used to fertilize nim1-2 through nim1-6. Because nim1-1 carried resistance to kanamycin, F, progeny were identified by antibiotic resistance. In all cases, the kanamycin-resistant F, plants were nim, indicating they were all allelic to the nim1-1 mutant. Because the nim1-5 mutant is dominant and apparently homozygous for the mutation, it was necessary to analyze nim1-1 complementation in the $F_2$ generation. If nim1-1 and nim1-5 were allelic, then the expectation would be that all $F_2$ plants have a nim phenotype. If not, then 13 of 16 $F_2$ plants would have been expected to have a nim phenotype. Of 94 plants, 88 clearly supported fungal growth following INA treatment. Six plants showed an associated phenotype of black specks on the leaves reminiscent of a lesion mimic phenotype and supported little fungal growth following INA treatment. Because nim1-5 carries a point mutation in the NIM1 gene (infra), it is considered to be a nim1 allele.

To determine the relative strength of the different nim1 alleles, each mutant was analyzed for the growth of *P. parasitica* under normal growth conditions and following pretreatment with either SA, INA, or BTH. As shown in Table 1, during normal growth, nim1-1, nim1-2, nim1-3, nim1-4, and nim1-6 all supported approximately the same rate of fungal growth, which was somewhat faster than the Ws-0 control. The exception was the nim1-5 plants, in which fungal growth was delayed by several days relative to both the other nim1 mutants and the Ws-0 control, but eventually all of the nim1-5 plants succumbed to the fungus. Following SA treatment, the mutants could be grouped into three classes: nim1-4 and nim1-6 showed a relatively rapid fungal growth; nim1-1, nim1-2, nim1-3 plants exhibited a somewhat slower rate of fungal growth; and fungal growth in nim1-5 plants was even slower than in the untreated Ws-0 controls. Following either INA or BTH treatment, the mutants also seemed to fall into three classes where nim1-4 was the most severely compromised in its ability to restrict fungal growth following chemical treatment; nim1-1, nim1-2, nim1-3, and nim1-6 were all moderately compromised; and nim1-5 was only slightly compromised. In these experiments, Ws-O did not support fungal growth following INA or BTH treatment. Thus, with respect to inhibition of fungal growth following chemical treatment, the mutants fall into three classes with nim1-4 being the most severely compromised, nim1-1, nim1-2, nim1-3 and nim1-6 showing an intermediate inhibition of fungus and nim1-5 with only slightly impaired fungal resistance.

Figure 3:
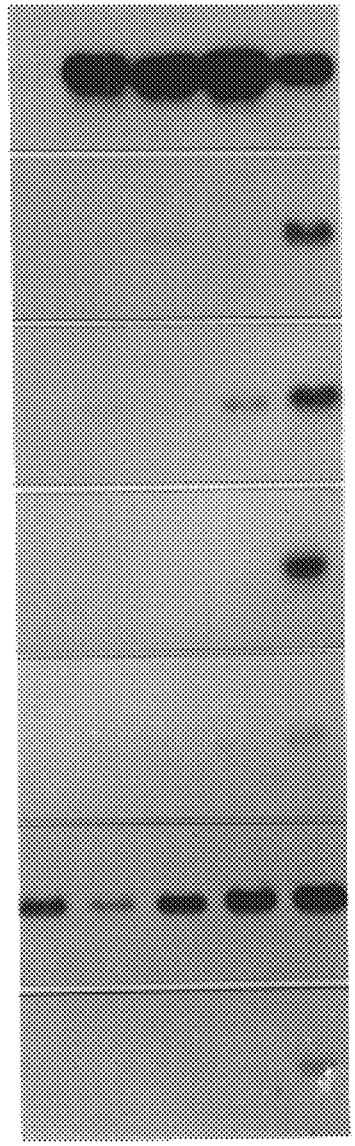
FIG. 3 shows the accumulation of PR-1 mRNA in nim1 mutants and wild-type plants after pathogen infection or chemical treatment. Plants containing nim1 alleles nim1-1, -2, -3, -4, -5, and -6 and Ws-O (Ws) were treated with water (C), SA, INA, or BTH 3 days before RNA isolation. The Emwa sample consists of RNA isolated from plants 14 days post-inoculation with the Emwa isolate of *P. parasitica*. Blots were hybridized using an Arabidopsis PR-1 cDNA as a probe (Uknes et al., 1992).

The accumulation of PR-1 mRNA was also used as a criterion to characterize the different nim1 alleles. RNA was extracted from plants 3 days after either water or chemical treatment, or 14 days after inoculation with a compatible fungus (*P. parasitica* isolate Emwa). The RNA gel blot in FIG. 3 shows that PR-1 mRNA accumulated to high levels following treatment of wild-type plants with SA, INA, or BTH or infection by *P. parasitica*. In the nim1-1, nim1-2, and nim1-3 plants, PR-1 mRNA accumulation was dramatically reduced relative to the wild type following chemical treatment. PR-1 mRNA was also reduced following *P. parasitica* infection, but there was still some accumulation in these mutants. In the nim1-4 and nim1-6 plants, PR-1 mRNA accumulation was more dramatically reduced than in the other alleles following chemical treatment (evident in longer exposures) and significantly less PR-1 mRNA accumulated following *P. parasitica* infection, supporting the idea that these could be particularly strong nim1 alleles. Interestingly, PR-1 mRNA accumulation was elevated in the nim1-5 mutant, but only mildly induced following chemical treatment or *P. parasitica* infection. Based on both PR-1 mRNA accumulation and fungal infection, the mutants fall into three classes: severely compromised alleles (nim1-4 and nim1-6); moderately compromised alleles (nim1-1, nim1-2, and nim1-3); and a weakly compromised allele (nim1-5).

Fine Structure Mapping of the nim1 Mutation

To determine a rough map position for NIM1, 74 $F_2$ nim phenotype plants from a cross between nim1-1 (Ws-0) and *Landsberg erecta* (Ler) were identified for their susceptibility to *P. parasitica* and lack of accumulation of PR-1 mRNA following INA treatment. After testing a number of simple sequence length polymorphism (SSLP) markers (Bell and Ecker 1994), nim1 was found to lie about 8.2 centimorgans (cM) from nga128 and 8.2 cM from nga111 on the lower arm of chromosome 1. In subsequent analysis, nim1-1 was found to lie between nga111 and about 4 cM from the SSLP marker ATHGENEA.

For fine structure mapping, 1138 nim plants from an $F_2$ population derived from a cross between nim1-1 and Ler DP23 were identified based on both their inability to accumulate PR-1 mRNA and their ability to support fungal growth following INA treatment. DNA was extracted from these plants and scored for zygosity at both ATHGENEA and nga111. As shown in FIGS. 5A–5D, 93 recombinant chromosomes were identified between ATHGENEA and nim1, giving a genetic distance of approximately 4.1 cM (93 of 2276), and 239 recombinant chromosomes were identified between nga111 and nim1, indicating a genetic distance of about 10.5 cM (239 of 2276). Informative recombinants in the ATHGENEA to nga111 interval were further analyzed using amplified fragment length polymorphism (AFLP) analysis (Vos et al., 1995).

Initially, 10 AFLP markers between ATHGENEA and nga111 were identified and these were used to construct a low resolution map of the region (FIG. 5A). The AFLP markers W84.2 (1 cM from nim1) and W85.1 (0.6 cM from nim1) were used to isolate yeast artificial chromosome (YAC) clones from the CIC (for Centre d'Etude du Polymorphisme Humain, INRA and CNRS) library (Creusot et al., 1995). Two YAC clones, CIC12H07 and CIC12F04, were identified with W84.2 and two YAC clones CIC7E03 and CIC10G07 (data not shown) were identified with the W85.1 marker. However, it was determined that there was a gap between the two sets of flanking YAC clones. From this point, bacterial artificial chromosome (BAC) and P1 clones that overlapped CIC12H07 and CIC12F04 were isolated and mapped, and three sequential walking steps were then carried out extending the BAC/P1 contig toward NIM1 (Liu et al., 1995; Chio et al., 1995). At various times during the walk, new AFLPs were developed that were specific for BAC or P1 clones, and these were used to determine whether the NIM1 gene had been crossed. It to was determined that the NIM1 gene had been crossed when BAC and P1 clones were isolated that gave rise to both AFLP markers L84.6a and L84.8. The AFLP marker L84.6a found on P1 clones P1-18, P1-17, and P1-21 identified three recombinants and L84.8 found on P1 clones P1-20, P1-22, P1-23, and P1-24 and BAC clones, BAC-04, BAC-05, and BAC-06 identified one recombinant. Because these clones overlap to form a large contig (>100 kb), and include AFLP markers that flank nim1, the gene was located on the contig. The BAC and P1 clones that comprised the contig were used to generate eight additional AFLP markers, which showed that nim1 was located between L84.Y1 and L84.8, representing a gap of about 0.09 cM.

A cosmid library was constructed in the Agrobacterium-compatible T-DNA cosmid vector pCLD04541 using DNA from BAC-06, BAC-04, and P1-18. A cosmid contig was developed using AFLP markers derived from these clones. Physical mapping showed that the physical distance between L84.Y1 and L84.8 was greater than 90 kb, giving a genetic to physical distance of roughly 1 megabase per cM. To facilitate the later identification of the NIM1 gene, the DNA sequence of BAC-04 was determined.

Isolation of the NIM1 Gene

To identify which cosmids contained the NIM1 gene, the 12 cosmids listed in Table 4 of the Examples were transformed into nim1-1, and transformants were evaluated for their ability to complement the mutant phenotype. Cosmids D5, E1, and D7 were all found to complement nim1-1, as determined by the ability of the transformants to accumulate PR-1 mRNA following INA treatment. The ends of these cosmids were sequenced and found to be located on the DNA sequence of BAC-04. There were 9,918 base pairs in the DNA region shared by D7 and D5 that contained the NIM1 gene. As shown in FIG. 5D, four putative gene regions were identified in -this 10-kb sequence. Region 1 could potentially encode a protein of 19,105 D, region 3 could encode a protein of 44,554 D, and region 4 could encode a protein of 52,797 D. Region 2 had four open reading frames of various sizes located close together, suggesting a gene with three introns. Analysis using the NetPlantGene program (Hebsgaard et al., 1996) indicated a high probability that the open reading frames could be spliced together to form a large open reading frame encoding a protein of 66,039 D.

To ascertain which gene region contained the NIM1 gene, gel blots containing RNA isolated from leaf tissue of Ws-0 and the different nim1 mutants following either water or chemical treatment were probed with DNA derived from each of the four gene regions. In these experiments, care was taken to label probes to high specific activity and autoradiographs were exposed for more than 1 week. In our past experience, these conditions would identify RNA at concentrations of about one copy per cell. The only gene region that produced detectable RNA was gene region 2. As shown in FIG. 7, the mRNA identified by the gene region 2 probe was induced by BTH treatment of wild-type plants, but not in any of the mutants. Furthermore, RNA accumulation was elevated in all of the plants following *P. parasitica* infection, indicating that this particular gene is induced following pathogen infection.

To further establish the gene region encoding NIM1, the DNA sequence from each of the four gene regions was determined for each of the nim1 alleles and compared with the corresponding gene region from Ws-0. No mutations were detected between Ws-0 and the mutant alleles in either gene regions 3 or 4 and only a single change was found in gene region 1 in the nim1-6 mutant. However, a single base pair mutation was found in each of the alleles relative to Ws-0 for region 2. The DNA sequence of gene region 2 is shown in FIG. 6. As shown in Table 5 and FIG. 6, in nim1-1, a single adenosine is inserted at position 3579 that causes a frameshift resulting in a change in seven amino acids and a deletion of 349 amino acids. In nim1-2, there is a cytidineto-thymidine transition at position 3763 that changes a histidine to a tyrosine. In nim1-3, a single adenosine is deleted at position 3301 causing a frameshift that altered 10 amino acids and deleted 412 from the predicted protein. Interestingly, both nim1-4 and nim1-5 have a guanosine-to-adenosine transition at position 4160 changing an arginine to a lysine, and in nim1-6, there is a cytosine-to-thymidine transition resulting in a stop codon causing the deletion of 255 amino acids from the predicted protein. Although the mutation in nim1-4 and nim1-5 alters the consensus donor splice site for the mRNA, RT-PCR analysis indicates that this mutation does not lead to an alteration of mRNA splicing (data not shown).

NIM1 Homologues

The gene region 2 DNA sequence was used in a Blast search (Altschul et al., 1990) and identified an exact match with the Arabidopsis expressed sequence tag (EST) T22612 and significant matches to the rice ESTs S2556, S2861, S3060 and S3481. A DNA probe covering base pairs 2081 to 3266 was used to screen an Arabidopsis cDNA library, and 14 clones were isolated that correspond to gene region 2. From the cDNA sequence, we could confirm the placement of the exon/intron borders shown in FIG. 6. Rapid amplification of CDNA ends by polymerase chain reaction (RACE) was carried out using RNA from INA-treated Ws-0 plants and the likely transcriptional start site was determined to be the A at position 2588 in FIG. 6.

Using the NIM1 CDNA as a probe, homologs of Arabidopsis NIM1 can be identified and isolated through screening genomic or cDNA libraries from different plants such as, but not limited to following crop plants: rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane. Standard techniques for accomplishing this include hybridization screening of plated DNA libraries (either plaques or colonies; see, e.g. Sambrook et al., *Molecular Cloning*, eds., Cold Spring Harbor Laboratory Press. (1989)) and amplification by PCR using oligonucleotide primers (see, e.g. Innis et al., *PCR Protocols, a Guide to Methods and Applications* eds., Academic Press (1990)). Homologues identified are genetically engineered into the expression vectors listed below and transformed into the above listed crops. Transformants are evaluated for enhanced disease resistance using relevant pathogens of the crop plant being tested.

For example, NIM1 homologs in the genomes of cucumber, tomato, tobacco, maize, wheat and barley have been detected by DNA blot analysis. Genomic DNA was isolated from cucumber, tomato, tobacco, maize, wheat and barley, restriction digested with the enzymes BamHI, HindIII, XbaI, or SalI, electrophoretically separated on 0.8% agarose gels and transferred to nylon membrane by capillary blotting. Following UV-crosslinking to affix the DNA, the membrane was hybridized under low stringency conditions [(1% BSA; 520 mM NaPO$_4$, pH 7.2; 7% lauryl sulfate, sodium salt; 1 mM EDTA; 250 mM sodium chloride) at 55° C. for 18–24 h] with $^{32}$P-radiolabelled *Arabidopsis thaliana* NIM1 cDNA. Following hybridization the blots were washed under low stringency conditions [6 XSSC for 15 min. (X3) 3 XSSC for 15 min. (X1) at 55° C.; 1 XSSC is 0.15M NaCl, 15 mM Na-citrate (pH 7.0)] and exposed to X-ray film to visualize bands that correspond to NIM1.

In addition, expressed sequence tags (EST) identified with similarity to the NIM1 gene such as the rice EST's described above can also be used to isolate homologues. The rice EST's may be especially useful for isolation of NIM1 homologues from other monocots.

Homologues may also be obtained by PCR. In this method, comparisons are made between known homologues (e.g., rice and Arabidopsis). Regions of high amino acid and DNA similarity or identity are then used to make PCR primers. Once a suitable region is identified, primers for that region are made with a diversity of substitutions in the 3$^{rd}$ codon position. The PCR reaction is performed from cDNA or genomic DNA under a variety of standard conditions. When a band is apparent, it is cloned and/or sequences to determine if it is a NIM1 homologue.

High-Level Expression of NIM1 Confers Disease Resistance In Plants

The present invention also concerns the production of transgenic plants that express higher-than-wild-type levels of the NIM1 gene, or functional variants and mutants thereof, and thereby have broad spectrum disease resistance. In a preferred embodiment of the invention, the expression of the NIM1 gene is at a level which is at least two-fold above the expression level of the NIM1 gene in wild-type plants and is preferably tenfold above the wild-type expression level. High-level expression of the NIM1 gene mimics the effects of inducer compounds in that it gives rise to plants with a constitutive immunity (CIM) phenotype.

Several methods are described for producing plants that overexpress the NIM1 gene and thereby have a CIM phenotype. A first method is selecting transformed plants that have high-level expression of NIM1 and therefore a CIM phenotype due to insertion site effect. Table 6 shows the results of testing of various transformants for resistance to fungal infection. As can be seen from this table, a number of transformants showed less than normal fungal growth and several showed no visible fungal growth at all. RNA was prepared from collected samples and analyzed as described in Delaney et al, 1995. Blots were hybridized to the Arabidopsis gene probe PR-1 (Uknes et al, 1992). Three lines showed early induction of PR-1 gene expression in that PR-1 mRNA was evident by 24 or 48 hours following fungal treatment. These three lines also demonstrated resistance to fungal infection.

In addition, methods are described for constructing plant transformation vectors comprising a constitutive plant-active promoter, such as the CaMV 35S promoter, operatively linked to a coding region that encodes an active NIM1 protein. High levels of the active NMB1 protein produce the same disease-resistance effect as chemical induction with inducing chemicals such as BTH, INA, and SA.

The overexpression of the NIM1 gene in plants results in immunity to a wide array of plant pathogens, which include, but are not limited to viruses or viroids, e.g. tobacco or cucumber mosaic virus, ringspot virus or necrosis virus, pelargonium leaf curl virus, red clover mottle virus, tomato bushy stunt virus, and like viruses; fungi, e.g. *Phythophthora parasitica* and *Peronospora tabacina*; bacteria, e.g. *Pseudomonas syringae* and *Pseudomonas tabaci*; insects such as aphids, e.g. *Myzus persicae*; and lepidoptera, e.g., Heliothus spp.; and nematodes, e.g., *Meloidogyne incognita*. The vectors and methods of the invention are useful against a number of disease organisms of maize including but not limited to downy mildews such as *Scleropthora macrospora, Sclerophthora rayissiae, Sclerospora*

*graminicola, Peronosclerospora sorghi, Peronosclerospora philippinensis, Peronosclerospora sacchari* and *Peronosclerospora maydis*; rusts such as *Puccinia sorphi, Puccinia polysora* and *Physopella zeae*; other fungi such as *Cercospora zeae-maydis, Colletotrichum graminicola, Fusarium monoliforne, Gibberella zeae, Exserohilum turcicum, Kabatiellu zeae, Erysiphe graminis, Septoria* and *Bipolaris maydis*; and bacteria such as *Erwinia stewartii.*

The methods of the present invention can be utilized to confer disease resistance to a wide variety of plants, including gymnosperms, monocots, and dicots. Although disease resistance can be conferred upon any plants falling within these broad classes, it is particularly useful in agronomically important crop plants, such as rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane. Transformed cells can be regenerated into whole plants such that the gene imparts disease resistance to the intact transgenic plants. The expression system can be modified so that the disease resistance gene is continuously or constitutively expressed.

Recombinant DNA Technology

The NIM1 DNA molecule or gene fragment conferring disease resistance to plants by allowing induction of SAR gene expression can be incorporated in plant or bacterial cells using conventional recombinant DNA technology. Generally, this involves inserting the DNA molecule comprised within SEQ ID NO: 1 or a functional variant thereof into an expression system to which the DNA molecule is heterologous (i.e., not normally present). The heterologous DNA molecule is inserted into the expression system or vector in proper orientation and correct reading frame. The vector contains the necessary elements for the transcription and translation of the inserted protein-coding sequences. A large number of vector systems known in the art can be used, such as plasmids, bacteriophage viruses and other modified viruses. Suitable vectors include, but are not limited to, viral vectors such as lambda vector systems 1gt11, 1gt10 and Charon 4; plasmid vectors such as pBI121, pBR322, pACYC177, pACYC184, pAR series, pKK223-3, pUC8, pUC9, pUC18, pUC19, pLG339, pRK290, pKC37, pKC101, pCDNAII; and other similar systems. The NIM1 coding sequence described herein can be cloned into the vector using standard cloning procedures in the art, as described by Maniatis et al., *Molecular Cloning: A Laboratory Manual*, lo Cold Spring Laboratory, Cold Spring Harbor, N.Y. (1982).

In order to obtain efficient expression of the gene or gene fragment of the present invention, a promoter which will result in a sufficient expression level or constitutive expression must be present in the expression vector. RNA polymerase normally binds to the promoter and initiates transcription of a gene. Promoters vary in their strength, i.e., ability to promote transcription. Depending upon the host cell system utilized, any one of a number of suitable promoters can be used. The components of the expression cassette may be modified to increase expression. For example, truncated sequences, nucleotide substitutions or other modifications may be employed. Plant cells transformed with such modified expression systems, then, exhibit overexpression or constitutive expression of genes necessary for activation of SAR.

A. Construction of Plant Transformation Vectors

Numerous transformation vectors are available for plant transformation, and the genes of this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), and the EPSPS gene, which confers resistance to glyphosate (U.S. Pat. Nos. 4,940,935 and 5,188,642).

1. Vectors Suitable for Agrobacterium Transformation

Many vectors are available for transformation using *Agrobacterium tumefaciens*. These typically carry at least one T-DNA border sequence and include vectors such as pBIN19 (Bevan, Nucl. Acids Res. (1984)) and pXYZ. Below, the construction of two typical vectors is described.

a. pCIB200 and pCIB2001:

The binary vectors pCIB200 and pCIB2001 are used for the construction of recombinant vectors for use with Agrobacterium and are constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982): Bevan et al., Nature 304: 184–187 (1983): McBride et al., Plant Molecular Biology 14: 266–276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153–161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

b. pCIB10 and Hygromycin Selection Derivatives thereof:

The binary vector pCIB10 contains a gene encoding kanamycin resistance for selection in plants and T-DNA right and left border sequences and incorporates sequences from the wide host-range plasmid pRK252 allowing it to replicate in both *E. coli* and Agrobacterium. Its construction is described by Rothstein et al. (Gene 53: 153–161 (1987)). Various derivatives of pCIB10 are constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

2. Vectors Suitable for non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on Agrobacterium include transformation via particle bombardment, protoplast uptake (e.g. PEG and electroporation) and microinjection. The choice of vector depends largely on the preferred selection for the species being transformed.

a. pCIB3064:

pCIB3064 is a pUC-derived vector suitable for direct gene transfer techniques in combination with selection by the herbicide basta (or phoSphInothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces viridochromogenes* is excised and inserted into the HpaI site of pCIB3060 (Thompson et al. EMBO J 6: 2519–2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindlII, and BamHI. This vector is suitable for the cloning of plant expression cassettes containing their own regulatory signals.

b. pSOG19 and pSOG35:

pSOG35 is a transformation vector which utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindlII, SphI, PstI and EcoRI sites available for the cloning of foreign substances.

B. Requirements for Construction of Plant Expression Cassettes

Gene sequences intended for expression in transgenic plants are first assembled in expression cassettes behind a suitable high expression level promoter and upstream of a suitable transcription terminator. These expression cassettes can then be easily transferred to the plant transformation vectors described above.

1. Promoter Selection

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the NIM1 gene product. Alternatively, the selected promoter may drive expression of the gene under a light-induced or other temporally regulated promoter.

a. Constitutive Expression, the CaMV 35S Promoter:

Construction of the plasmid pCGN1761 is described in the published patent application EP 0 392 225 (example 23) which is hereby incorporated by reference. pCGN1761 contains the "double" 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or gene sequences (including microbial ORF sequences) within its polylinker for the purpose of their expression under the control of the 35S promoter in transgenic plants. The entire 35S promoter-gene sequence-mi terminator cassette of such a construction can to be excised by HindIII, SphI, SalI, and XbaI sites 5' to the promoter and XbaI, BamHI and BglI sites 3' to the terminator for transfer to transformation vectors such as those described above. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter.

b. Modification of pCGN1761ENX by Optimization of the Translational Initiation Site:

For any of the constructions described herein, modifications around the cloning sites can be made by the introduction of sequences which may enhance translation. This is particularly useful when overexpression is desired.

PCGN1761ENX is cleaved with SphI, treated with T4 DNA polymerase and religated, thus destroying the SphI site located 5' to the double 35S promoter. This generates vector pCGN1761ENX/Sph-. pCGN1761ENX/Sph- is cleaved with EcoRI, and ligated to an annealed molecular adaptor of the sequence 5'-AATTCTAAAGCATGCCGATCGG-3'/5'-AATTCCGATCGGCATGCTTTA-3' (SEQ ID NO's: 12 and 13). This generates the vector pCGNSENX, which incorporates the quasi-optimized plant translational initiation sequence TAAA-C adjacent to the ATG which is itself part of an SphI site which is suitable for cloning, heterologous genes at their initiating methionine. Downstream of the SphI site, the EcoRI, NotI, and XhoI sites are retained.

An alternative vector is constructed which utilizes an NcoI site at the initiating ATG. This vector, designated pCGN1761NENX is made by inserting an annealed molecular adaptor of the sequence 5'-AATTCTAAACCATGGCGATCGG-3'/5'-

AATTCCGATCGCCATGGTTTA-3' (SEQ ID NO's: 14 and 15) at the pCGN1761ENX EcoRI site. Thus the vector includes the quasi-optimized sequence TAAACC adjacent to the initiating ATG which is within the NcoI site. Downstream sites are EcoRI, NotI, and XhoI. Prior to this manipulation, however, the two NcoI sites in the pCGN1761ENX vector (at upstream positions of the 5' 35S promoter unit) are destroyed using similar techniques to those described above for SphI or alternatively using "inside-outside" PCR. Innes et al. PCR Protocols: A guide to methods and applications. Academic Press, New York (1990). This manipulation can be assayed for any possible detrimental effect on expression by insertion of any plant cDNA or reporter gene sequence into the cloning site followed by routine expression analysis in plants.

c. Expression under a Chemically/Pathogen Regulatable Promoter:

The double 35S promoter in pCGN176 1ENX may be replaced with any other promoter of choice which will result in suitably high expression levels. By way of example, a chemically regulated PR-1 promoter, which is described in U.S. Pat. No. 5,614,3 95, which is hereby incorporated by reference in its entirety, may replace the double 35S promoter. The promoter of choice is preferably excised from its source by restriction enzymes, but can alternatively be PCR-amplified using primers which carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (see EP 0 332 104, example 21 for construction which is hereby incorporated by reference) and transferred to plasmid pCGN1761ENX (Uknes et al. 1992). pCIB 1004 is cleaved with NcoI and the resultant 3' overhang of the linearized fragment is rendered blunt by treatment with T4 DNA polymerase. The fragment is then cleaved with HindIII and the resultant PR-1a-promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB 1004 promoter fragment is cloned. This generates a pCGN1761ENX derivative with the PR-1a promoter and the tml terminator and an intervening polylinker with unique EcoRI and NotI sites. Selected NIM1 genes can be inserted into this vector, and the fusion products (i.e. promoter-gene-terminator) can subsequently be transferred to any selected transformation vector, including those described in this application.

Various chemical regulators may be employed to induce expression of the NIM1 coding sequence in the plants transformed according to the present invention. In the context of the instant disclosure, "chemical regulators" include chemicals known to be inducers for the PR-1 promoter in plants, or close derivatives thereof. A preferred group of regulators for the PR-1 promoter is based on the benzo-1, 2,3-thiadiazole (BTH) structure and includes, but is not limited to, the following to types of compounds: benzo-1, 2,3-thiadiazolecarboxylic acid, benzo-1,2,3-thiadiazolethiocarboxylic acid, cyanobenzo-1,2,3-thiadiazole, benzo-1,2,3-thiadiazolecarboxylic acid amide, benzo-1,2,3-thiadiazolecarboxylic acid hydrazide, benzo-1, 2,3-thiadiazole-7-carboxylic acid, benzo-1,2,3-thiadiazole-7-thiocarboxylic acid, 7-cyanobenzo-1,2,3-thiadiazole, benzo-1,2,3-thiadiazolecarboxylate in which the alkyl group contains one to six carbon atoms, methyl benzo-1,2,3-thiadiazole-7-carboxylate, n-propyl benzo-1,2,3-thiadiazole-7-carboxylate, benzyl benzo-1,2,3-thiadiazole-7-carboxylate, benzo-1,2,3-thiadiazole-7-carboxylic acid sec-butylhydrazide, and suitable derivatives thereof. Other chemical inducers may include, for example, benzoic acid, salicylic acid (SA), polyacrylic acid and substituted derivatives thereof, suitable substituents include lower alkyl, lower alkoxy, lower alkylthio, and halogen. Still another group of regulators for the chemically inducible DNA sequences of this invention is based on the pyridine carboxylic acid structure, such as the isonicotinic acid structure and preferably the haloisonicotinic acid structure. Preferred are dichloroisonicotinic acids and derivatives thereof, for example the lower alkyl esters. Suitable members of this class of regulator compounds are, for example, 2,6-dichloroisonicotinic acid (INA), and the lower alkyl esters thereof, especially the methyl ester.

d. Constitutive Expression, the Actin Promoter:

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163–171 (1990)). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150–160 (1991)). These incorporate the ActI-intron 1, AdhI 5¢ flanking sequence and AdhI-intron 1 (from the maize alcohol dehydrogenase gene) and sequence from the CaMV 35S promoter. Vectors showing highest expression were fusions of 35S and ActI intron or the ActI 50 flanking sequence and the ActI intron. Optimization of sequences around the initiating ATG (of the GUS reporter gene) also enhanced expression. The promoter expression cassettes described by McElroy et al. (Mol. Gen. Genet. 231: 150–160 (1991)) can be easily modified for the expression of cellulase genes and are particularly suitable for use in monocotyledonous hosts. For example, promoter-containing fragments is removed from the McElroy constructions and used to replace the double 35S promoter in pCGN 1761 ENX, which is then available for the insertion of specific gene sequences. The fusion genes thus constructed can then be transferred to appropriate transformation vectors. In a separate report the rice ActI promoter with its first intron has also been found to direct high expression in cultured barley cells (Chibbar et al. Plant Cell Rep. 12: 506–509 (1993)).

e. Constitutive Expression, the Ubiquitin Promoter:

Ubiquitin is another gene product known to accumulate in many cell types and its promoter has been cloned from several species for use in transgenic plants (e.g. sunflower—Binet et al. Plant Science 79: 87–94 (1991) and maize—Christensen et al. Plant Molec. Biol. 12: 619–632 (1989)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491–495 (1993)) describe a vector (pAHC25) which comprises the maize ubiquitin promoter and first intron and its high activity in cell suspensions of numerous monocotyledons when introduced via microprojectile bombardment. The ubiquitin promoter is suitable for the expression of cellulase genes in transgenic plants, especially monocotyledons. Suitable vectors are derivatives of pAHC25 or any of the transformation vectors described in this application, modified by the introduction of the appropriate ubiquitin promoter and/or intron sequences.

f. Root Specific Expression:

Another pattern of expression for the NIM1 gene of the instant invention is root expression. A suitable root promoter is described by de Framond (FEBS 290: 103–106 (1991)) and also in the published patent application EP 0 452 269 (to Ciba-Geigy) which is herein incorporated by reference. This promoter is transferred to a suitable vector such as pCGN1761ENX for the insertion of a cellulase gene and subsequent transfer of the entire promoter-gene-terminator cassette to a transformation vector of interest.

g. Wound-Inducible Promoters:

Wound-inducible promoters may also be suitable for expression of NIM1 genes of the invention. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. describe the 5¢ upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques. Similar, Firek et al. and Warner et al. have described a wound-induced gene from the monocotyledon *Asparagus officinalis* which is expressed at local wound and pathogen invasion sites. Using cloning techniques well known in the art, these promoters can be transferred to suitable vectors, fused to the NIM1 genes of this invention, and used to express these genes at the sites of plant wounding.

h. Pith-Preferred Expression:

Patent Application WO 93/07278 (to Ciba-Geigy) which is herein incorporated by reference describes the isolation of the maize trpA gene which is preferentially expressed in pith cells. The gene sequence and promoter extending up to –1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

i. Leaf-Specific Expression:

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

j. Expression with Chloroplast Targeting:

Chen & Jagendorf (J. Biol. Chem. 268: 2363–2367 (1993) have described the successful use of a chloroplast transit peptide for import of a heterologous transgene. This peptide used is the transit peptide from the rbcS gene from *Nicotiana plumbaginifolia* (Poulsen et al. Mol. Gen. Genet. 205: 193–200 (1986)). Using the restriction enzymes DraI and SphI. pr Tsp509I and SphI the DNA sequence encoding this transit peptide can be excised from the plasmid prbcS-8B and manipulated for use with any of the constructions described above. The DraI-SphI fragment extends from –58 relative to the initiating rbcS ATG to, and including, the first amino acid (also a methionine) of the mature peptide immediately after the import cleavage site, whereas the Tsp509I-SphI fragment extends from –8 relative to the initiating rbcS ATG to, and including, the first amino acid of the mature peptide.

Thus, these fragments can be appropriately inserted into the polylinker of any chosen expression cassette generating a transcriptional fusion to the untranslated leader of the chosen promoter (e.g. 35S, PR-1a, actin, ubiquitin etc.), while enabling the insertion of a NIM1 gene in correct fusion downstream of the transit peptide. Constructions of this kind are routine in the art. For example, whereas the DraI end is already blunt, the 5' Tsp509I site may be rendered blunt by T4 polymerase treatment, or may alternatively be ligated to a linker or adaptor sequence to facilitate its fusion to the chosen promoter. The 3' SphI site may be maintained as such, or may alternatively be ligated to adaptor of linker sequences to facilitate its insertion into the chosen vector in such a way as to make available appropriate restriction sites for the subsequent insertion of a selected NIM1 gene. Ideally the ATG of the SphI site is maintained and comprises the first ATG of the selected NIM1 gene. Chen & Jagendorf provide consensus sequences for ideal cleavage for chloroplast import, and in each case a methionine is preferred at the first position of the mature protein. At subsequent positions there is more variation and the amino acid may not be so critical. In any case, fusion constructions can be assessed for efficiency of import in vitro using the methods described by Bartlett et al. (In: Edelmann et al. (Eds.) Methods in Chloroplast Molecular Biology, Elsevier pp 1081–1091 (1982)) and Wasmann et al. (Mol. Gen. Genet. 205: 446–453 (1986)). Typically the best approach may be to generate fusions using the selected NIM1 gene with no modifications at the amino terminus, and only to incorporate modifications when it is apparent that such fusions are not chloroplast imported at high efficiency, in which case modifications may be made in accordance with the established literature (Chen & Jagendorf; Wasman et al.; Ko & Ko, J. Biol. Chem 267: 13910–13916 (1992)).

A preferred vector is constructed by transferring the DraI-SphI transit peptide encoding fragment from prbcS-8B to the cloning vector pCGN1761ENX/Sph-. This plasmid is cleaved with EcoRI and the termini rendered blunt by treatment with T4 DNA polymerase. Plasmid prbcS-8B is cleaved with SphI and ligated to an annealed molecular adaptor of the sequence 5'-CCAGCTGGAATTCCG-3'/5'-CGGAATTCCAGCTGGCATG-3' (SEQ ID NO's: 16 and 17). The resultant product is 5'-terminally phosphorylated by treatment with T4 kinase. Subsequent cleavage with DraI releases the transit peptide encoding fragment which is ligated into the blunt-end ex-EcoRI sites of the modified vector described above. Clones oriented with the 5' end of the insert adjacent to the 3' end of the 35S promoter are identified by sequencing. These clones carry a DNA fusion of the 35S leader sequence to the rbcS-8A promoter-transit peptide sequence extending from –58 relative to the rbcS ATG to the ATG of the mature protein, and including in that region a unique SphI site, and a newly created EcoRI site, as well as the existing NotI and XhoI sites of pCGN1761ENX. This new vector is designated pCGN1761/CT. DNA sequences are transferred to pCGN1761/CT in frame by amplification using PCR techniques and incorporation of an SphI, NSphI, or NlaIII site at the amplified ATG, which following restriction enzyme cleavage with the appropriate enzyme is ligated into SphI-cleaved pCGN1761/CT. To facilitate construction, it may be required to change the second amino acid of the product of the cloned gene; however, in almost all cases the use of PCR together with standard site directed mutagenesis will enable the construction of any desired sequence around the cleavage site and first methionine of the mature protein.

A further preferred vector is constructed by replacing the double 35S promoter of pCGN1761ENX with the BamHI-SphI fragment of prbcS-8A which contains the full-length, light-regulated rbcS-8A promoter from −1038 (relative to the transcriptional start site) up to the first methionine of the mature protein. The modified pCGN1761 with the destroyed SphI is cleaved with PstI and EcoRI and treated with T4 DNA polymerase to render termini blunt. prbcS-8A is cleaved with SphI and ligated to the annealed molecular adaptor of the sequence described above. The resultant product is 5′-terminally phosphorylated by treatment with T4 kinase. Subsequent cleavage with BamHI releases the promoter-transit peptide containing fragment which is treated with T4 DNA polymerase to render the BamHI terminus blunt. The promoter-transit peptide fragment thus generated is cloned into the prepared pCGN176 1ENX vector, generating a construction comprising the rbcS-8A promoter and transit peptide with an SphI site located at the cleavage site for insertion of heterologous genes. Further, downstream of the SphI site there are EcoRI (re-created), NotI, and XhoI cloning sites. This construction is designated pCGN1761rbcS/CT.

Similar manipulations can be undertaken to utilize other GS2 chloroplast transit peptide encoding sequences from other sources (monocotyledonous and dicotyledonous) and from other genes. In addition, similar procedures can be followed to achieve targeting to other subcellular compartments such as mitochondria.

2. Transcriptional Terminators

A variety of transcriptional terminators are available for use in expression cassettes. These are responsible for the termination of transcription beyond the transgene and its correct polyadenylation. Appropriate transcriptional terminators are those which are known to function in plants and include the CaMV 35S terminator, the tml terminator, the nopaline synthase terminator and the pea rbcS E9 terminator. These can be used in both monocotyledons and dicotyledons.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al, Genes Develop. 1: 1183–1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gailie et al. Nucl. Acids Res. 15: 8693–8711 (1987); Skuzeski et al. Plant Molec. Biol. 15: 65–79 (1990)).

4. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104–15109 (1988)). These signal sequences can be fused to heterologous gene products to effect the import of heterologous products into the chloroplast (van den Broeck, et al. Nature 313: 358–363 (1985)). DNA encoding for appropriate signal sequences can be isolated from the 5′ end of the cDNAs encoding the RUBISCO protein, the CAB protein, the EPSP synthase enzyme, the GS2 protein and many other proteins which are known to be chloroplast localized.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512–6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) Methods in Chloroplast Molecular Biology, Elsevier pp 1081–1091 (1982) and Wasmann et al. Mol. Gen. Genet. 205: 446–453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter which has an expression pattern different to that of the promoter from which the targeting signal derives.

C. Transformation

Once the NIM1 coding sequence has been cloned into an expression system, it is transformed into a plant cell. Plant tissues suitable for transformation include leaf tissues, root tissues, meristems, and protoplasts. The present system can be utilized in any plant which can be transformed and regenerated. Such methods for transformation and regeneration are well known in the art. Methodologies for the construction of plant expression cassettes as well as the introduction of foreign DNA into plants is generally described in the art. Generally, for the introduction of foreign DNA into plants, Ti plasmid vectors have been utilized for the delivery of foreign DNA. Also utilized for such delivery have been direct DNA uptake, liposomes, electroporation, micro-injection, and microprojectiles. Such methods had been published in the art. See, for example, Bilang et al. (1991) *Gene* 100: 247–250; Scheid et al., (1991) *Mol. Gen. Genet.* 228: 104–112; Guerche et al., (1987) *Plant Science* 52: 111–116; Neuhause et al., (1987) *Theor. Appl. Genet.* 75: 30–36; Klein et al., (1987) *Nature* 327: 70–73; Howell et al., (1980) *Science* 208:1265; Horsch et al., (1985) *Science* 227: 1229–1231; DeBlock et al., (1989) *Plant Physiology* 91: 694–701; *Methods for Plant Molecular Biology* (Weissbach and Weissbach, eds.) Academic Press, Inc. (1988); and *Methods in Plant Molecular Biology* (Schuler and Zielinski, eds.) Academic Press, Inc. (1989). See also U.S. patent application Ser. Nos. 08/438, 666. filed May 10, 1995, and 07/951,715, filed Sep. 25, 1992, both of which are incorporated herein by reference in their entirety. It is understood that the method of transformation will depend upon the plant cell to be transformed. Transformation of tobacco, tomato, potato, and *Arabidopsis thaliana* using a binary Ti vector system. *Plant Physiol.* 81:301–305, 1986; Fry, J., Barnason, A., and Horsch, R. B. Transformation of Brassica napus with Agrobacterium tumefaciens based vectors. *Pl. Cell Rep.* 6:321–325, 1987; Block, M. d. Genotype independent leaf disc transformation of potato (Solanum tuberosum) using Agrobacterium tumefaciens. *Theor. appl. genet.* 76:767–774, 1988; Deblock, M., Brouwer, D. D., and Tenning, P. Transformation of Brassica napus and Brassica oleracea using Agrobacterium tumefaciens and the Expression of the bar and neo genes in the transgenic plants. *Plant Physiol.* 91:694–701, 1989; Baribault, T. J., Skene, K. G. M., Cain, P. A., and Scott, N. S. Transgenic grapevines: regeneration of shoots expressing beta-glucuronidase. *Pl. Cell Rep.* 41:1045–1049, 1990; Hinchee, M. A. W., Newell, C. A., ConnorWard, D. V., Armstrong, T. A., Deaton, W. R., Sato, S. S., and Rozman, R. J. Transformation and regeneration of non-solanaceous crop plants. *Stadler. Genet. Symp.* 203212.203–212, 1990; Barfield, D. G. and Pua, E. C. Gene transfer in plants of Brassica juncea using Agrobacterium tumefaciens-mediated transformation. *Pl. Cell Rep.* 10:308–314, 1991; Cousins, Y. L., Lyon, B. R., and Llewellyn, D. J. Transformation of an Australian cotton cultivar: prospects for cotton improvement through genetic engineering. *Aust. J. Plant Physiol.* 18:481 494. 1991; Chee, P. P. and Slightom, J. L. Transformation of Cucumber Tissues by Microprojectile Bombardment Identification of Plants Containing Functional and Nonfunctional Transferred Genes. *GENE* 118:255–260, 1992; Christou, P., Ford, T. L., and Kofron, M. The development of a variety-independent gene-transfer method for rice. *Trends. Biotechnol.* 10:239–246, 1992; D'Halluin, K., Bossut, M., Bonne, E., Mazur, B., Leemans, J., and Botterman, J. Transformation of sugarbeet (Beta vulgaris L.) and evaluation of herbicide resistance in transgenic plants. *Bio/Technol.* 10:309–314.1992; Dhir, S. K., Dhir, S., Savka, M. A., Belanger, F., Kriz, A. L., Farrand, S. K., and Widholm, J. M. Regeneration of Transgenic Soybean (Glycine Max) Plants from Electroporated Protoplasts. *Plant Physiol* 99:81–88, 1992; Ha, S. B., Wu, F. S., and Thorne, T. K. Transgenic turf-type tall fescue (Festuca arundinacea Schreb.) plants regenerated from protoplasts. *Pl. Cell Rep.* 11:601–604, 1992; Blechl, A. E. Genetic Transformation The New Tool for Wheat Improvement 78th Annual Meeting Keynote Address. *Cereal Food World* 38:846–847, 1993; Casas, A. M., Kononowicz, A. K., Zehr, U. B., Tomes, D. T., Axtell, J. D., Butler, L. G., Bressan, R. A., and Hasegawa, P. M. Transgenic Sorghum Plants via Microprojectile Bombardment. *Proc Natacad Sci USA* 90:11212–11216, 1993; Christou, P. Philosophy and Practice of Variety Independent Gene Transfer into Recalcitrant Crops. *In Vitro Cell Dev Biol-Plant* 29P: 119–124, 1993; Darniani, F., Nenz, E., Paolocci, F., and Arcioni, S. Introduction of Hygromycin Resistance in Lotus spp Through Agrobacterium Rhizogenes Transformation. *Transgenic Res* 2:330–335, 1993; Davies, D. R., Hamilton, J., and Mullineaux, P. Transformation of Peas. *Pl. Cell Rep.* 12:180–183, 1993; Dong, J. Z. and Mchughen, A. Transgenic Flax Plants from Agrobacterium Mediated Transformation Incidence of Chimeric Regenerants and Inheritance of Transgenic Plants. *Plant Sci* 91:139–148, 1993; Fitch, M. M. M., Manshardt, R. M., Gonsalves, D., and Slightom, J. L. Transgenic Papaya Plants from Agrobacterium Mediated Transformation of Somatic Embryos. *Pl. Cell Rep.* 12:245–249, 1993; Franklin, C. I. and Trieu, T. N. Transformation of the Forage Grass Caucasian Bluestem via Biolistic Bombardment Mediated DNA Transfer. *Plant Physiol* 102:167, 1993; Golovkin, M. V., Abraham, M., Morocz, S., Bottka, S., Feher, A., and Dudits, D. Production of Transgenic Maize Plants by Direct DNA Uptake into Embryogenic Protoplasts. *Plant Sci* 90:41–52, 1993; Guo, G. Q., Xu, Z. H., Wei, Z. M., and Chen, H. M. Transgenic Plants Obtained from Wheat Protoplasts Transformed by Peg Mediated Direct Gene Transfer. *Chin Sci Bull* 38:2072–2078. 1993; Asano, Y. and Ugaki, M. Transgenic plants of Agrostis alba obtained by electroporationmediated direct gene transfer into protoplasts. *Pl. Cell Rep.* 13, 1994; Ayres, N. M. and Park, W. D. Genetic Transformation of Rice. *Crit Rev Plant Sci* 13:219–239, 1994; Barcelo, P., Hagel, C., Becker, D., Martin, A., and Lorz, H. Transgenic Cereal (Tritordeum) Plants Obtained at High Efficiency by Microprojectile Bombardment of Inflorescence Tissue. *PLANT J* 5:583–592, 1994; Becker, D., Brettschneider, R., and Lorz, H. Fertile Transgenic Wheat from Microprojectile Bombardment of Scutellar Tissue. *Plant J* 5:299–307, 1994; Biswas, G. C. G., Iglesias, V. A., Datta, S. K., and Potrykus, I. Transgenic Indica Rice (Oryza Sativa L) Plants Obtained by Direct Gene Transfer to Protoplasts. *J Biotechnol* 32: 1–10, 1994; Borkowska, M., Kleczkowski, K., Klos, B., Jakubiec, J., and Wielgat, B. Transformation of Diploid Potato with an Agrobacterium Tumefaciens Binary Vector System.1.Methodological Approach. *Acta Physiol Plant* 16:225–230, 1994; Brar, G. S., Cohen, B. A., Vick, C. L., and Johnson, G. W. Recovery of Transgenic Peanut (Arachis Hypogaea L) Plants from Elite Cultivars Utilizing Accell(R) Technology. *Plant J* 5:745–753, 1994; Christou, P. Genetic Engineering of Crop Legumes and Cereals Current Status and Recent Advances. *Agro Food Ind Hi Tech* 5: 17–27, 1994; Chupeau, M. C., Pautot, V., and Chupeau, Y. Recovery of Transgenic Trees After Electroporation of Poplar Protoplasts. *Transgenic Res* 3: 13–19, 1994; Eapen, S. and George, L. Agrobacterium Tumefaciens Mediated Gene Transfer in Peanut (Arachis Hypogaea L). *Pl. Cell Rep.* 13:582–586, 1994; Hartman, C. L., Lee, L., Day, P. R., and Tumer, N. E. Herbicide Resistant Turfgrass (Agrostis Palustris Huds) by Biolistic Transformation. *Bid-Technology* 12:919923, 1994; Howe, G. T., Goldfarb, B., and Strauss, S. H. Agrobacterium Mediated Transformation of Hybrid Poplar Suspension Cultures and Regeneration of Transformed Plants. *Plant Cell Tissue & Orgart Culture* 36:59–71, 1994; Konwar, B. K. Agrobacterium Tumefaciens Mediated Genetic Transformation of Sugar Beet (Beta Vulgaris L). *J Plantbiochem Biotechnol* 3:37–41, 1994; Ritala, A., Aspegren, K., Kurten, U., Salmenkalliomarttila, M., Mannonen, L., Hannus, R., Kauppinen, V., Teeri, T. H., and Enari, T. M. Fertile Transgenic Barley by Particle Bombardment of Inmature Embryos. *Plant Mol Biol* 24:317–325, 1994; Scorza, R., Cordts, J. M., Ramming, D. W., and Emershad, R. L. Transformation of Grape (Vitis Vinifera L) Somatic Embryos and Regeneration of Transgenic Plants. *J Cell Biochem:* 102, 1994; Shimamoto, K. Gene Expression in Transgenic Monocots. *Curr Opinbiotechnol* 5:158–162, 1994; Spangenberg, G., Wang, Z. Y., Nagel, J., and Potrykus, I. Protoplast Culture and Generation of Transgenic Plants in Red Fescue (Festuca Rubra L). *Plant Sci* 97:83–94, 1994; Spangenberg, G., Wang, Z. Y., Nagel, J., and Potrykus, I. Gene Transfer and Regeneration of Transgenic Plants in Forage Grasses. *J Cell Biochem:* 102, 1994; Wan, Y. C. and Lemaux, P. G. Generation of Large Numbers of Independently Transformed Fertile Barley Plants. *Plant Physiol* 104:3748, 1994; Weeks, J. T., Anderson, O. D., and Blechl, A. E. Stable Transformation of Wheat (Triticum Aestivum L) by Microprojectile Bombardment. *J Cell Biochem* :104, 1994; Ye, X. J., Brown, S. K., Scorza, R., Cordts, J., and Sanford, J. C. Genetic Transformation of Peach Tissues by Particle Bombardment. *Jamer Sochortsci* 119:367–373, 1994; Spangenberg, G., Wang, Z. Y., Nagel, J., and Potrykus, I. Protoplast Culture And Generation Of Transgenic Plants In Red Fescue (Festuca Rubra <, L). *Plant Science* 1994 97:83–94, 1995.

Bacteria from the genus Agrobacterium can be utilized to transform plant cells. Suitable species of such bacterium include *Agrobacterium tumefaciens* and *Agrobacterium rhizogens*. *Agrobacterium tumefaciens* (e.g., strains LBA4404 or EHA105) is particularly useful due to its well-known ability to transform plants.

1. Transformation of Dicotyledons

Transformation techniques for dicotyledons are well known in the art and include Agrobacterium-based techniques and techniques which do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. The many crop species which are alfalfa and poplar (EP 0 317 511 (cotton [1313]), EP 0 249 432 (tomato, to Calgene), WO 87/07299 (Brassica, to Calgene), U.S. Pat. No. 4,795,855 (poplar)). Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to Agrobacterium is accomplished by a triparental mating procedure using *E. coli* carrying the recombinant binary vector, a helper *E. coli* strain which carries a plasmid such as pRK2013 and which is able to mobilize the recombinant binary vector to the target Agrobacterium strain. Alternatively, the recombinant binary vector can be transferred to Agrobacterium by DNA transformation (Höfgen & Willmitzer, Nucl. Acids Res. 16: 9877 (1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050; 5,036,006; and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435 ([1280/1281] to Ciba-Geigy), EP 0 392 225 (to Ciba-Geigy) and WO 93/07278 (to Ciba-Geigy) describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment.

Furthermore, application WO 93/07278 (to Ciba-Geigy) and Koziel et al. (Biotechnology 11:194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation has been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantarum 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent. Patent application 08/147,161 describes methods for wheat transformation and is hereby incorporated by reference.

Breeding

The isolated gene fragment of the present invention can be utilized to confer disease resistance to a wide variety of plant cells, including those of gymnosperms, monocots, and dicots. Although the gene can be inserted into any plant cell falling within these broad classes, it is particularly useful in crop plant cells, such as rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

The high-level expression of the NIM1 gene and mutants thereof necessary for constitutive expression of SAR genes, in combination with other characteristics important for production and quality, can be incorporated into plant lines through breeding. Breeding approaches and techniques are known in the art. See, for example, Welsh J. R., *Fundamentals of Plant Genetics and Breeding*, John Wiley & Sons, NY (1981); *Crop Breeding*, Wood D. R. (Ed.) American Society of Agronomy Madison, Wisconsin (1983); Mayo O., *The Theory of Plant Breeding*, Second Edition, Clarendon Press, Oxford (1987); Singh, D. P., *Breeding for Resistance to Diseases and Insect Pests*, Springer-Verlag, NY (1986); and Wricke and Weber, *Quantitative Genetics and Selection Plant Breeding*, Walter de Gruyter and Co., Berlin (1986).

Disease Resistance evaluation is performed by methods known in the art. For examples see, Uknes et al, (1993) Molecular Plant Microbe Interactions 6: 680–685; Gorlach et al., (1996) Plant Cell 8:629–643; Alexander et al., Proc. Natl. Acad. Sci. USA 90: 7327–7331.

EXAMPLES

The invention is illustrated in further detail by the following detailed procedures, preparations, and examples. The examples are for illustration only, and are not to be construed as limiting the scope of the present invention.

Standard recombinant DNA and molecular cloning techniques used here are well known in the art and are described by Sambrook, et al., *Molecular Cloning*, eds., Cold Spring Harbor Laboratory Press, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

A. Characterization of nim1 Mutants

Example 1

Plant Lines and Fungal Strains

*Arabidopsis thaliana* ecotype Isilewskija (Ws-O; stock number CS 2360) and fourth-generation ($T_4$) seeds from T-DNA-transformed lines were obtained from the Ohio State University Arabidopsis Biological Resource Center (Columbus, OH). Second generation ($M_2$) seeds from ethyl methane sulfonate (EMS) mutagenized Ws-O plants were obtained from Lehle Seeds (Round Rock, Tex.).

*Pseudomonas syringae* pv. Tomato (Pst) strain DC3000 containing the cloned avrRpt2 gene [DC3000(avrRpt2)] was obtained from B. Staskawicz, University of California, Berkeley. *P. parasitica* pathovars and their sources were as follows: Emwa from E. Holub and I. R. Crute, Horticultural Research Station, East Malling, Kent; Wela from A. Slusarenko and B. Mauch-Mani, Institut fur Pflanzenbiologie, Zürich, Switzerland; and Noco from J. Parker, Sainsbury Laboratory, Norwich, England. Fungal cultures were maintained by weekly culturing on Arabidopsis ecotype Ws-O, Weiningen, and Col-O, for *P. parasitica* pathovars Emwa, Wela, and Noco, respectively.

Example 2

Mutant Screens $M_2$ or $T_4$ seeds were grown on soil for 2 weeks under 14 hr of light per day, misted with 0.33 mM INA (0.25 mg/ml made from 25% INA in wettable powder; Ciba, Basel, Switzerland), and inoculated 4 days later by spraying a *P. parasitica* conidial suspension containing $5-10 \times 10^4$ conidiospores per ml of water. This fungus is normally virulent on the Arabidopsis Ws-O ecotype, unless resistance is first induced in these plants with isonicotinic acid (INA) or a similar compound. Plants were kept under humid conditions at 18° C. for 1 week and then scored for fungal sporulation. Plants that supported fungal growth after INA treatment were selected as putative mutants.

Following incubation in a high humidity environment, plants with visible disease symptoms were identified, typically 7 days after the infection. These plants did not show resistance to the fungus, despite the application of the resistance-inducing chemical and were thus potential nim (noninducible-immunity) mutant plants. From 360,000 plants, 75 potential nim mutants were identified.

These potential mutant plants were isolated from the flat, placed under low humidity conditions and allowed to set seed. Plants derived from this seed were screened in an identical manner for susceptibility to the fungus Emwa, again after pretreatment with INA. The progeny plants that showed infection symptoms were defined as nim mutants. Six nim lines were thus identified. One line (nim1-1) was isolated from the T-DNA population and five (nim1-2, nim1-3, nim1-4, nim1-5, and nim1-6) from the EMS population.

Example 3

Disease Resistance of nim1 Plants

Salicylic acid (SA) and benzo(1,2,3)thiadiazole-7-carbothioic acid S-methyl ester (BTH) are chemicals that, like INA, induce broad spectrum disease resistance (SAR) in wild type plants. Mutant plants were treated with SA, INA, and BTH and then assayed for resistance to *Peronospora parasitica*. *P. parasitica* isolate 'Emwa' is a P.p. isolate that is compatible in the Ws ecotype. Compatible isolates are those that are capable of causing disease on a particular host. The *P. parasitica* isolate 'Noco' is incompatible on Ws but compatible on the Columbia ecotype. Incompatible pathogens are recognized by the potential host, eliciting a host response that prevents disease development.

Wild-type seeds and seeds for each of the nim1 alleles (nim1-1, -2, -3, -4, -5, -6) were sown onto MetroMix 300 growing media, covered with a transparent plastic dome, and placed at 4° C. in the dark for 3 days. After 3 days of 4° C. treatment, the plants were moved to a phytotron for 2 weeks. By approximately 2 weeks post-planting, germinated seedlings had produced 4 true leaves. Plants were then treated with $H_2O$, 5 mM SA, 300 µM BTH, or 300 µM INA. Chemicals were applied as a fine mist to completely cover the seedlings using a chromister. Water control plants were returned to the growing phytotron while the chemically treated plants were held in a separate but identical phytotron. At 3 days post-chemical application, water and chemically treated plants were inoculated with the compatible 'Emwa' isolate. 'Noco' inoculation was conducted on water treated plants only. Following inoculation, plants were covered with a clear plastic dome to maintain high humidity required for successful *P. parasitica* infection and placed in a growing chamber with 19° C. day/17° C. night temperatures and 8 h light/16 h dark cycles.

To determine the relative strength of the different nim1 alleles, each mutant was microscopically analyzed at various timepoints after inoculation for the growth of *P. parasitica* under normal growth conditions and following pretreatment with either SA, INA, or BTH. Under magnification, sporulation of the fungus could be observed at very early stages of disease development. The percentage of plants/pot showing sporulation at 5 d, 6 d, 7 d, 11 d and 14 d after inoculation was determined and the density of sporulation was also recorded.

Table 1 shows, for each of the nim1 mutant plant lines, the percent of plants that showed some surface conidia on at least one leaf after infection with the Emwa race of *P. parasitica*. *P. parasitica* was inoculated onto the plants three days after water or chemical treatment. The table indicates the number of days after infection that the disease resistance was rated.

TABLE 1

| mutant | Day 0 | Day 5 | Day 6 | Day 7 | Day 11 |
|---|---|---|---|---|---|
| Percent Infection - Emwa/Control | | | | | |
| Ws WT | 0 | 10 | 25 | 100 | 90 |
| nim1-1 | 0 | 75 | 95 | 100 | 100 |
| nim1-2 | 0 | 30 | 85 | 100 | 100 |
| nim1-3 | 0 | 30 | 90 | 100 | 100 |
| nim1-4 | 0 | 80 | 100 | 100 | 100 |
| nim1-5 | 0 | 0 | 5 | 100 | 100 |
| nim1-6 | 0 | 5 | 70 | 80 | 100 |
| Percent Infection - Emwa/SA | | | | | |
| Ws WT | 0 | 5 | 30 | 70 | 100 |
| nim1-1 | 0 | 5 | 95 | 100 | 100 |
| nim1-2 | 0 | 5 | 95 | 100 | 100 |
| nim1-3 | 0 | 10 | 90 | 100 | 100 |
| nim1-4 | 0 | 75 | 100 | 100 | 100 |
| nim1-5 | 0 | 0 | 20 | 75 | 100 |
| nim1-6 | 0 | 80 | 100 | 100 | 100 |
| Percent Infection - Emwa/INA | | | | | |
| Ws WT | 0 | 0 | 0 | 0 | 0 |
| nim1-1 | 0 | 5 | 80 | 100 | 100 |
| nim1-2 | 0 | 15 | 95 | 100 | 100 |
| nim1-3 | 0 | 10 | 60 | 100 | 100 |
| nim1-4 | 0 | 80 | 100 | 100 | 100 |
| nim1-5 | 0 | 0 | 0 | 5 | 5 |
| nim1-6 | 0 | 1 | 50 | 90 | 100 |
| Percent Infection - Emwa/BTH | | | | | |
| Ws WT | 0 | 0 | 0 | 0 | 0 |
| nim1-1 | 0 | 1 | 5 | 30 | 100 |
| nim1-2 | 0 | 0 | 25 | 90 | 100 |
| nim1-3 | 0 | 15 | 70 | 100 | 100 |
| nim1-4 | 0 | 80 | 100 | 100 | 100 |
| nim1-5 | 0 | 0 | 1 | 1 | 10 |
| nim1-6 | 0 | 1 | 90 | 100 | 100 |

As shown in Table 1, during normal growth, nim1-1, nim1-2, nim1-3, nim1-4, and nim1-6 all supported approximately the same rate of fungal growth, which was somewhat faster than the Ws-0 control. The exception was the nim1-5 plants where fungal growth was delayed by several days relative to both the other nim1 mutants and the Ws-0 control, but eventually all of the nim1-5 plants succumbed to the fungus.

Following SA treatment, the mutants could be grouped into three classes: nim1-4 and nim1-6 showed a relatively rapid fungal growth; nim1-1, nim1-2, nim1-3 plants exhibited a somewhat slower rate of fungal growth; and fungal growth in nim1-5 plants was even slower than in the untreated Ws-0 controls. Following either INA or BTH treatment, the mutants also fell into three classes where nim1-4 was the most severely compromised in its ability to restrict fungal growth following chemical treatment; nim1-1, nim1-2, nim1-3, and nim1-6 were all moderately compromised; and nim1-5 was only slightly compromised. In these experiments, Ws-0 did not support fungal growth following INA or BTH treatment. Thus, with respect to inhibition of fungal growth following chemical treatment, the mutants fell into three classes with nim1-4 being the most severely compromised, nim1-1, nim1-2, nim1-3 and nim1-6 showing an intermediate inhibition of fungus and nim1-5 with only slightly impaired fungal resistance.

Table 2 shows the disease resistance assessment via infection rating of the various nim1 alleles as well as of NahG plants at 7 and 11 days after innoculation with *Peronospora parasitica*. WsWT indicates the Ws wild type parent line in which the nim1 alleles were found. The various nim1 alleles are indicated in the table and the NahG plant is indicated also.

A description of the NahG plant has been previously published. (Delaney et al., Science 266, pp. 1247–1250 (1994)). NahG Arabidopsis is also described in U.S. patent application Ser. No. 08/454,876, incorporated by reference herein. nahG is a gene from *Pseudomonas putida* encoding a salicylate hydroxylase that converts salicylic acid to catechol, thereby eliminating the accumulation of salicylic acid, a necessary signal transduction component for SAR in plants. Thus, NahG Arabidopsis plants do not display normal SAR, and they show much greater susceptibility in general to pathogens. However, the NahG plants still respond to the chemical inducers INA and BTH. NahG plants therefore serve as a kind of universal susceptibility control.

TABLE 2

| mutant | Day 7 | Day 11 |
|---|---|---|
| Infection Severity - Emwa/Water | | |
| Ws WT | 3 | 3 |
| nim1-1 | 4 | 4.5 |
| nim1-2 | 3 | 4 |
| nim1-3 | 4 | 4 |
| nim1-4 | 5 | 5 |
| nim1-5 | 1 | 3.5 |
| nim1-6 | 3 | 4.5 |
| NahG | 4 | 5 |
| Infection Severity - Emwa/SA | | |
| Ws WT | 3 | 4 |
| nim1-1 | 3 | 4.5 |
| nim1-2 | 3 | 4 |
| nim1-3 | 3 | 4 |
| nim1-4 | 4 | 5 |
| nim1-5 | 3 | 3 |
| nim1-6 | 4 | 4.5 |
| NahG | 4 | 5 |
| Infection Severity - Emwa/INA | | |
| Ws WT | 0 | 0 |
| nim1-1 | 2.5 | 4 |
| nim1-2 | 4 | 4 |
| nim1-3 | 3 | 3.5 |
| nim1-4 | 4 | 5 |
| nim1-5 | 1 | 2 |
| nim1-6 | 3 | 4.5 |
| NahG | 3 | 3 |
| Infection Seventy - Emwa/BTH | | |
| Ws WT | 0 | 0 |
| nim1-1 | 2.5 | 4 |
| nim1-2 | 3.5 | 4 |
| nim1-3 | 3 | 3.5 |
| nim1-4 | 4 | 5 |
| nim1-5 | 1.5 | 2 |
| nim1-6 | 3 | 4 |
| NahG | 0 | 0 |

From Table 2 it can be seen that the nim1-4 and nim1-6 alleles had the most severe *Peronospora parasitica* infections; this was most easily observable at the earlier time points. In addition, the nim1-5 allele showed the greatest response to both INA and BTH and therefore was deemed the weakest nim1 allele. The NahG plants showed very good response to both INA and BTH and looked very similar to the nim1-5 allele. However, at late time points, Day 11 in the Table, the disease resistance induced in the NahG plants began to fade, and there was a profound difference between INA and BTH in that the INA-induced resistance faded much faster and more severely than the resistance induced in the NahG plants by BTH. Also seen in these experiments was that INA and BTH induced very good resistance in Ws to Emwa, and the nim1-1, nim1-2 and other nim1 alleles showed virtually no response to SA or INA with regard to disease resistance.

The nim1 plants' lack of responsiveness to the SAR-inducing chemicals SA, INA, and BTH implies that the mutation is downstream of the entry point(s) for these chemicals in the signal transduction cascade leading to systemic acquired resistance.

Example 4

Northern Analysis of SAR Gene Expression

Since SA, INA and BTH did not induce SAR, or SAR gene expression in any of the nim1 plants, it was of interest to investigate whether pathogen infection could induce SAR gene expression in these plants, as it does in wild type plants. Thus, the accumulation of SAR gene mRNA was also used as a criterion to characterize the different nim1 alleles.

Wild-type seeds and seeds for each of the nim1 alleles (nim1-1, -2, -3, -4, -5, -6) were sown onto MetroMix 300 growing media, covered with a transparent plastic dome, and placed at 4° C. in the dark for 3 days. After 3 days of 4° C. treatment, the plants were moved to a phytotron for 2 weeks. By approximately two weeks post-planting, germinated seedlings had produced 4 true leaves. Plants were then treated with $H_2O$, 5 mM SA, 300 μM BTH, or 300 μM INA. Chemicals were applied as a fine mist to completely cover the seedlings using a chromister. Water control plants were returned to the growing phytotron while the chemically treated plants were held in a separate but identical phytotron. At 3 days post-chemical application, water and chemically treated plants were inoculated with the compatible Emwa isolate. Noco inoculation was conducted on water treated plants only. Following inoculation, plants were covered with a clear plastic dome to maintain high humidity required for successful *P. parasitica* infection and placed in a growing chamber with 19° C. day/17° C. night temperatures and 8h light/16h dark cycles. RNA was extracted from plants 3 days after either water or chemical treatment, or 14 days after inoculation with the compatible *P. parasitica* Emwa isolate. The RNA was size-fractionated by agarose gel electrophoresis and transferred to GeneScreenPlus membranes (DuPont).

Figure 1:
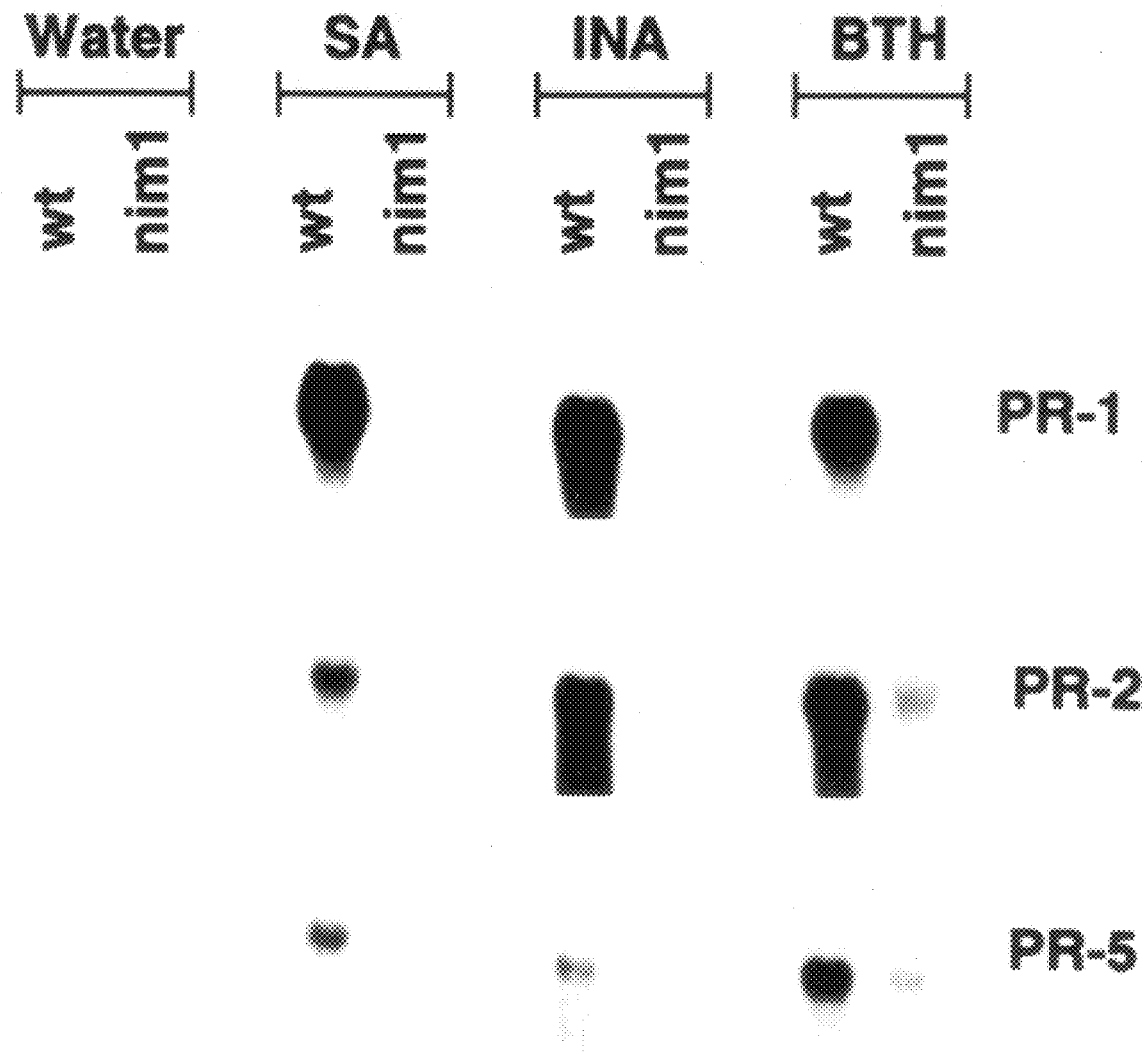
FIG. 1 shows the effect of chemical inducers on the induction of SAR gene expression in wild-type and nim1 plants. Chemical induction of SAR genes is diminished in nim1 plants. Water, SA, INA, or BTH is applied to wild type (WT) and nim1 plants. After 3 days, RNA is prepared from these plants and examined for expression of PR-1, PR-2, and PR-5.
Figure 2:
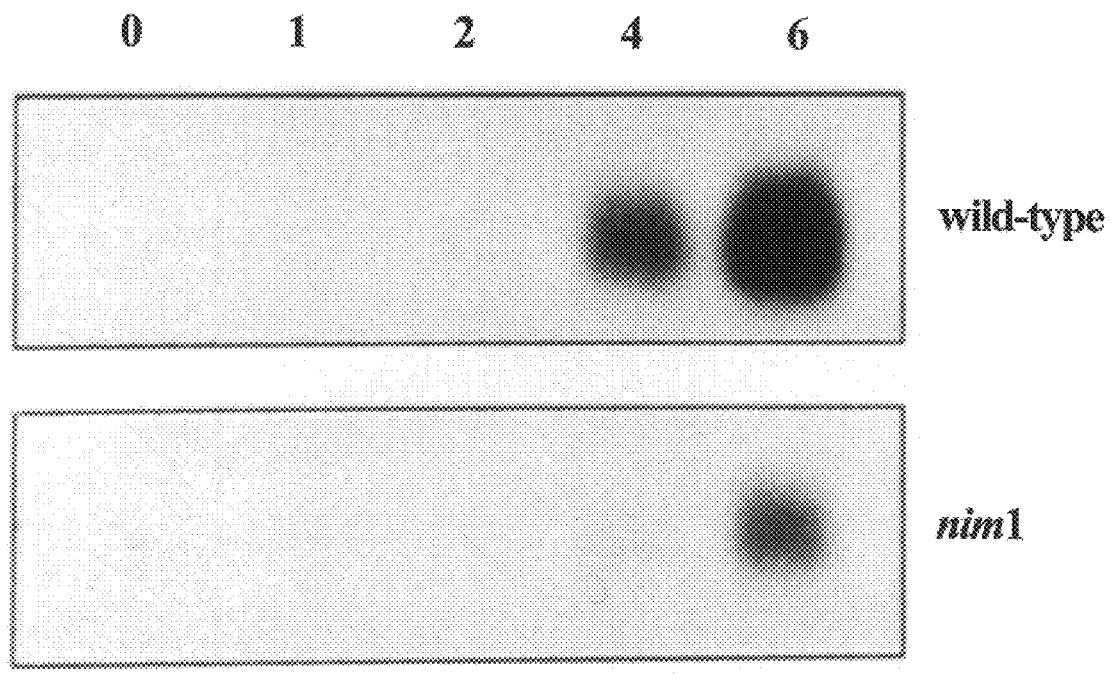
FIG. 2 depicts PR-1 gene expression in pathogen-infected Ws-O and nim1 plants. Pathogen induction of PR-1 is diminished in nim1 plants. Wild type (WT) and nim1 plants were spray-inoculated with the Emwa race of *P. parasitica*. Samples were collected at days 0, 1, 2, 4, and 6 and RNA is analyzed by blot hybridization with an *A. thaliana* PR-1 cDNA probe to measure PR-1 mRNA accumulation.

FIGS. 1–3 present various RNA gel blots that indicate that SA, INA and BTH induce neither SAR nor SAR gene expression in nim1 plants. In FIG. 1, replicate blots were hybridized to Arabidopsis gene probes PR-1, PR-2 and PR-5 as described in Uknes et al. (1992). In contrast to the case in wild type plants, the chemicals did not induce RNA accumulation from any of these 3 SAR genes in nim1-1 plants.

As shown in FIG. 2, pathogen infection (Emwa) of wild type Ws-O plants induced PR-1 gene expression within 4 days after infection. In nim1-1 plants, however, PR-1 gene expression was not induced until 6 days after infection and the level was reduced relative to the wild type at that time. Thus, following pathogen infection, PR-1 gene expression in nim1-1 plants was delayed and reduced relative to the wild type.

The RNA gel blot in FIG. 3 shows that PR-1 mRNA accumulates to high levels following treatment of wild-type plants with SA, INA, or BTH or infection by *P. parasitica*. In the nim1-1, nim1-2, and nim1-3 plants, PR-1 mRNA accumulation was dramatically reduced relative to the wild type following chemical treatment. PR-1 mRNA was also reduced following *P. parasitica* infection, but there was still some accumulation in these mutants. In the nim1-4 and nim1-6 plants, PR-1 mRNA accumulation was more dramatically reduced than in the other alleles following chemical treatment (evident in longer exposures) and significantly less PR-1 mRNA accumulated following *P. parasitica* infection, supporting the idea that these are particularly strong nim1 alleles. PR-1 mRNA accumulation was elevated in the nim1-5 mutant, but only mildly induced following chemical treatment or *P. parasitica* infection. Based on both PR-1 mRNA accumulation and fungal infection, the mutants have been determined to fall into three classes: severely compromised alleles (nim1-4 and nim1-6); moderately compromised alleles (nim1-1, nim1-2, and nim1-3); and a weakly compromised allele (nim1-5).

Example 5

Determination of SA Accumulation in nim1 Plants

Figure 4:
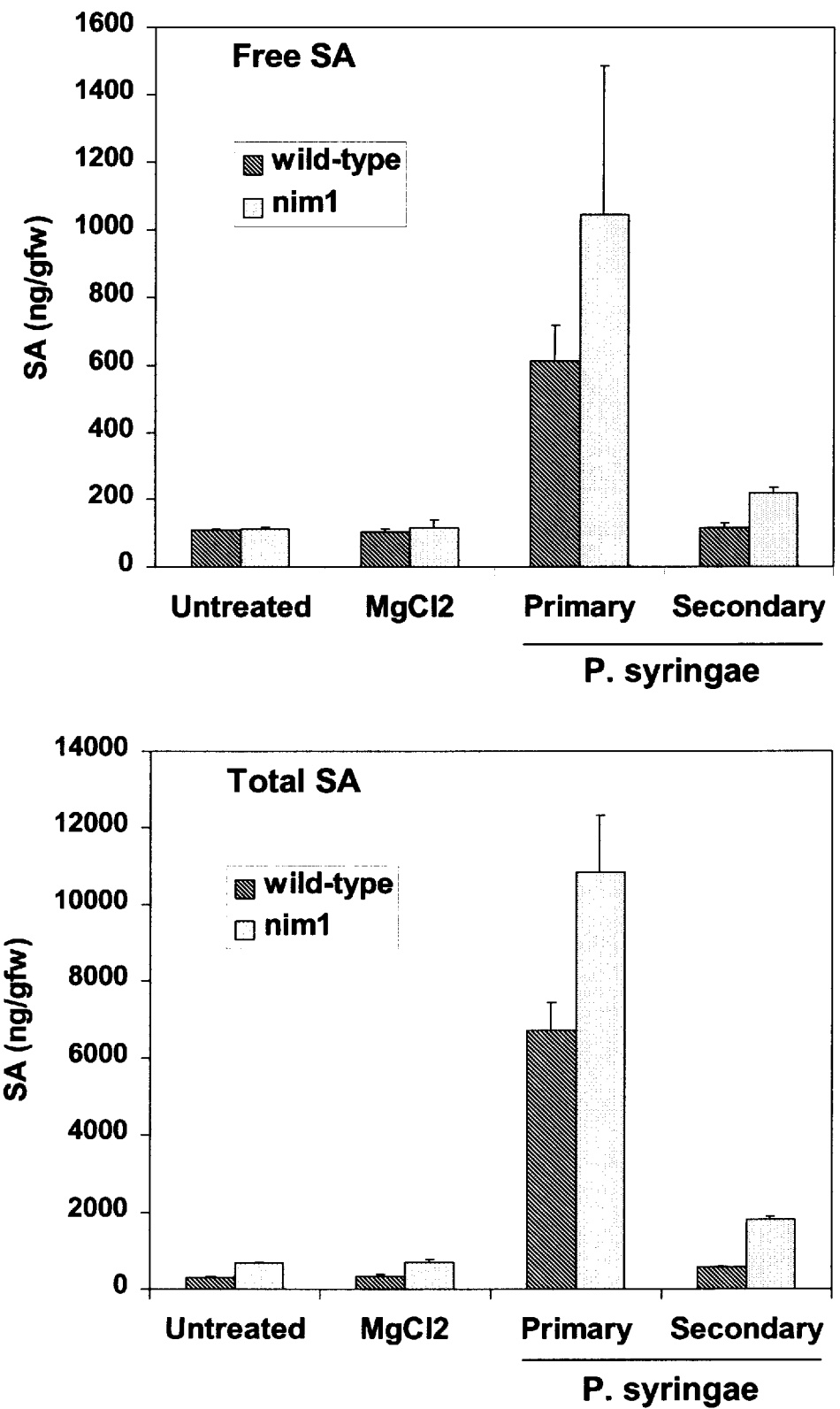
FIG. 4 shows the levels of SA accumulation in Ws-O and nim1 plants infected with *P. syringae*. nim1 plants accumulate SNA following pathogen exposure. Leaves of wild type and nim1 plants are infiltrated with Pst DC3000(avrRpt2) or carrier medium (10 mM $MgCl_2$) alone. After 2 days, samples were collected from untreated, $MgCl_2$-treated, and DC3000(avrRpt2)-treated plants. Bacteria-treated samples were separated into primary (infiltrated) and secondary (noninfiltrated) leaves. Free SA and total SA following hydrolysis with β-glucosidase were quantified by HPLC. Error bars indicate SD of three replicate samples.

Infection of wild type plants with pathogens that cause a necrotic reaction leads to accumulation of SA in the infected tissues. Endogenous SA is required for signal transduction in the SAR pathway, as breakdown of the endogenous SA leads to a decrease in disease resistance. This defines SA accumulation as a marker in the SAR pathway (Gaffney et al, 1993, Science 261, 754–756). The phenotype of nim1 plants indicates a disruption in a component of the SAR pathway downstream of SA and upstream of SAR gene induction.

nim1 plants were tested for their ability to accumulate SA following pathogen infection. *Pseudomonas syringae* tomato strain DC 3000, carrying the avrRpt2 gene, was injected into leaves of 4-week-old nim1 plants. The leaves were harvested 2 days later for SA analysis as described by Delaney et al, 1995, PNAS 92, 6602–6606. This analysis showed that the nim1 plants accumulated a high levels of SA in infected leaves, as shown in FIG. 4. Uninfected leaves also accumulated SA, but not to the same levels as the infected leaves, similar to what has been observed in wild-type Arabidopsis. This indicates that the nim mutation maps downstream of the SA marker in the signal transduction pathway. Furthermore, INA and BTH (inactive in nim1 plants) have been demonstrated to stimulate a component in the SAR pathway downstream of SA (Vernooij et al. (1995); Friedrich, et al. (1996); and Lawton, et al. (1996)). In addition, as described above, exogenously applied SA did not protect nim1 plants from Emwa infection.

Example 6

Genetic Analysis

To determine dominance of the various mutants that display the nim1 phenotype, pollen from wild type plants was transferred to the stigmata of nim1-1, -2, -3, -4, -5, -6. If the mutation is dominant, then the nim1 phenotype will be observed in the resulting F1 plants. If the mutation is recessive, then the resulting F1 plants will exhibit a wild type phenotype.

The data presented in Table 3 show that when nim1-1, -2, -3, -4 and -6 were crossed with the wild type, the resulting F1 plants exhibited the wild type phenotype. Thus, these mutations are recessive. In contrast, the nim1-5 X wild type F1 progeny all exhibited the nim1 phenotype, indicating that this is a dominant mutation. Following INA treatment, no *P. parasitica* sporulation was observed on wild type plants, while the F1 plants supported growth and some sporulation of *P. parasitica*. However, the nim1 phenotype in these F1 plants was less severe than observed when nim1-5 was homozygous.

To determine allelism, pollen from the kanamycin-resistant nim1-1 mutant plants was transferred to the stigmata of nim1-2, -3, -4, -5, -6. Seeds resulting from the cross were plated onto Murashige-Skoog B5 plates containing kanamycin at 25 µg/ml to verify the hybrid origin of the seed. Kanamycin resistant (F1) plants were transferred to soil and assayed for the nim1 phenotype. Because the F1 progeny of the cross of the nim1-5 mutant with the Ws wild type displays a nim1 phenotype, analysis of nim1-5 X nim1-1 F2 was also carried out.

As shown in Table 3, all of the resulting F1 plants exhibited the nim1 phenotype. Thus, the mutation in the nim1-2, -3, -4, -5, -6 was not complemented by the nim1-1; these plants all fall within the same complementation group and are therefore allelic. F2 progeny from the nim1-5 X nim1-1 cross also displayed the nim1 phenotype, confirming that nim1-5 is a nim1 allele.

TABLE 3

Genetic Segregation of nim Mutants

| | | | | Phenotype | |
|---|---|---|---|---|---|
| Mutant | Generation | Female | Male | Wild type[a] | nim1[b] |
| nim1-1 | F1 | wild type[c] | nim1-1 | 24 | 0 |
| | F2 | | | 98 | 32 |
| nim1-2 | F1 | nim1-2 | Wild type | 3 | 0 |
| nim1-3 | F1 | nim1-3 | Wild type | 3 | 0 |
| nim1-4 | F1 | nim1-4 | Wild type | 3 | 0 |
| nim1-5 | F1 | nim1-5 | Wild type | 0 | 35 |
| | F1 | Wild type | nim1-5 | 0 | 18 |
| nim1-6 | F1 | nim1-6 | Wild type | 3 | 0 |
| nim1-2 | F1 | nim1-2 | nim1-1 | 0 | 15 |
| nim1-3 | F1 | nim1-3 | nim1-1 | 0 | 10 |
| nim1-4 | F1 | nim1-4 | nim1-1 | 0 | 15 |

TABLE 3-continued

Genetic Segregation of nim Mutants

| Mutant | Generation | Female | Male | Phenotype Wild type[a] | nim1[b] |
|---|---|---|---|---|---|
| nim1-5 | F1 | nim1-5 | nim1-1 | 0 | 14 |
|  | F2 |  |  | 9 | 85 |
| nim1-6 | F1 | nim1-6 | nim1-1 | 0 | 12 |

[a]Number of plants with elevated PR-1 mRNA accumulation and absence of *P. parasitica* after INA treatment.
[b]Number of plants with no PR-1 mRNA accumulation and presence of *P. parasitica* after INA treatment.
[c]Wild type denotes the wild type Ws-0 strain.

B. Mapping of the nim1 Mutation

Mapping of the nim1 mutation is described in exhaustive detail in Applicants' U.S. patent application Ser. No. 08/773,559, filed Dec. 27, 1996, which is incorporated by reference herein in its entirety.

Example 7

Identification of Markers in and Genetic Mapping of the NIM1 Locus

To determine a rough map position for NIM1, 74 $F_2$ nim plants from a cross between nim1-1 (Ws-0) and *Landsberg erecta* (Ler) were identified for their susceptibility to *P. parasitica* and lack of accumulation of PR-1 mRNA following INA treatment. Using simple sequence length polymorphism (SSLP) markers (Bell and Ecker 1994), nim1-1 was determined to lie about 8.2 centimorgans (cM) from nga128 and 8.2 cM from nga111 on the lower arm of chromosome 1. In addition, nim1-1 was determined to lie between nga111 and about 4 cM from the SSLP marker ATHGENEA. (FIG. 5A)

For fine structure mapping, 1138 nim plants from an $F_2$ population derived from a cross between nim1-1 and Ler DP23 were identified based on both their inability to accumulate PR-1 mRNA and their ability to support fungal growth following INA treatment. DNA was extracted from these plants and scored for zygosity at both ATHGENEA and nga111. As shown in FIG. 5A, 93 recombinant chromosomes were identified between ATHGENEA and nim1-1, giving a genetic distance of approximately 4.1 cM (93 of 2276), and 239 recombinant chromosomes were identified between nga111 and nim1-1, indicating a genetic distance of about 10.5 cM (239 of 2276). Informative recombinants in the ATHGENEA to nga111 interval were further analyzed using amplified fragment length polymorphism (AFLP) analysis (Vos et al., 1995).

AFLP markers between ATHGENEA and nga111 were identified and were used to construct a low resolution map of the region (FIGS. 5A and 5B). AFLP markers W84.2 (1 cM from nim1-1) and W85.1 (0.6 cM from nim1-1) were used to isolate yeast artificial chromosome (YAC) clones from the CIC (for Centre d'Etude du Polymorphisme Humain, INRA and CNRS) library (Creusot et al., 1995). Two YAC clones, CIC12H07 and CIC12F04, were identified with W84.2 and two YAC clones CIC7E03 and CIC10G07 were identified with the W85.1 marker. (FIG. 5B) To bridge the gap between the two sets of flanking YAC clones, bacterial artificial chromosome (BAC) and P1 clones that overlapped CIC12H07 and CIC12F04 were isolated and mapped, and sequential walking steps were carried out extending the BAC/PI contig toward NIM1 (FIG. 5C; Liu et al., 1995; Chio et al., 1995). New AFLP's were developed during the walk that were specific for BAC or P1 clones, and these were used to determine whether the NIM1 gene had been crossed. NIM1 had been crossed when BAC and P1 clones were isolated that gave rise to both AFLP markers L84.6a and L84.8. The AFLP marker L84.6a found on P1 clones P1-18, P1-17, and P1-21 identified three recombinants and L84.8 found on P1 clones P1-20, P1-22, P1-23, and P1-24 and BAC clones, BAC-04, BAC-05, and BAC-06 identified one recombinant. Because these clones overlapped to form a large contig (>100 kb), and included AFLP markers that flanked nim1, the gene was determined to be located on the contig. The BAC and P1 clones that comprised the contig were used to generate additional AFLP markers, which showed that nim1 was located between L84.Y1 and L84.8, representing a gap of about 0.09 cM.

C. Isolation of the NIM1 Gene

Example 8

Construction of a Cosmid Contig

A cosmid library of the NIM1 region was constructed in the Agrobacterium-compatible T-DNA cosmid vector pCLD04541 using CsCl-purified DNA from BAC-06, BAC-04, and P1-18. The DNAs of the three clones were mixed in equimolar quantities and were partially digested with the restriction enzyme Sau3A. The 20–25 kb fragments were isolated using a sucrose gradient, pooled and filled in with DATP and dGTP. Plasmid pCLD04541 was used as T-DNA cosmid vector. This plasmid contains a broad host range pRK290-based replicon, a tetracycline resistance gene for bacterial selection and the nptII gene for plant selection. The vector was cleaved with XhoI and filled in with dCTP and dTTP. The prepared fragments were then ligated into the vector. The ligation mix was packaged and transduced into *E. coli* strain XL1-blue MR (Stratagene). Resulting transformants were screened by hybridization with the BAC04, BAC06 and P1-18 clones and positive clones isolated. Cosmid DNA was isolated from these clones and template DNA was prepared using the ECs EcoRI/MseI and HindIII/MseI. The resulting AFLP fingerprint patterns were analyzed to determine the order of the cosmid clones. A set of 15 semi-overlapping cosmids was selected spanning the nim region (FIG. 5D). The cosmid DNAs were also restricted with EcoRI, PstI, BssHII and SgrAI. This allowed for the estimation of the cosmid insert sizes and the verification of the overlaps between the various cosmids as determined by AFLP fingerprinting.

Physical mapping showed that the physical distance between L84.Y1 and L84.8 was >90 kb, giving a genetic to physical distance of 1 megabase per cM. To facilitate the identification of the NIM1 gene, the DNA sequence of BAC04 was determined.

Example 9

Identification of a Clone containing the NIM1 Gene

Cosmids generated from clones spanning the NIM1 region were moved into *Agrobacterium tumefaciens* AGL-1 through conjugative transfer in a tri-parental mating with helper strain HB101 (pRK2013). These cosmids were then used to transform a kanamycin-sensitive nim1-1 Arabidopsis line using vacuum infiltration (Bechtold et al., 1993; Mindrinos et al., 1994). Seed from the infiltrated plants was harvested and allowed to germinate on GM agar plates containing 50 mg/ml kanamycin as a selection agent. Only plantlets that were transformed with cosmid DNA could detoxify the selection agent and survive. Seedlings that survived the selection were transferred to soil approximately two weeks after plating and tested for the nim1 phenotype as described below. Transformed plants that no longer had the nim1 phenotype identified cosmid(s) containing a functional NIM1 gene.

Example 10

Complementation of the nim1 Phenotype

Plants transferred to soil were grown in a phytotron for approximately one week after transfer. 300 µm INA was applied as a fine mist to completely cover the plants using a chromister. After two days, leaves were harvested for RNA extraction and PR-1 expression analysis. The plants were then sprayed with *Peronospora parasitica* (isolate Emwa) and grown under high humidity conditions in a growing chamber with 19° C. day/17° C. night temperatures and 8 h light/16 h dark cycles. Eight to ten days following fungal infection, plants were evaluated and scored positive or negative for fungal growth. Ws and nim1 plants were treated in the same way to serve as controls for each experiment.

Total RNA was extracted from the collected tissue using a LiCl/phenol extraction buffer (Verwoerd, et al. 1989). RNA samples were run on a formaldehyde agarose gel and blotted to GeneScreen Plus (DuPont) membranes. Blots were hybridized with a $^{32}$P-labeled PR-1 cDNA probe. The resulting blots were exposed to film to determine which transformants were able to induce PR-1 expression after INA treatment. The results are summarized in Table 4, which shows complementation of the nim1 phenotype by cosmid clones D5, E1, and D7.

TABLE 4

| Clone Name | # of transformants | # of plants with INA induces PR-1/total # of plants tested (%) |
|---|---|---|
| A8 | 3 | 0/3 (0%) |
| A11 | 8 | 4/18 (22%) |
| C2 | 10 | 1/10 (10%) |
| C7 | 33 | 1/32 (3%) |
| D2 | 81 | 4/49 (8%) |
| D5 | 6 | 5/6 (83%) |
| E1 | 10 | 10/10 (100%) |
| D7 | 129 | 36/36 (100%) |
| E8 | 9 | 0/9 (0%) |
| F12 | 6 | 0/6 (0%) |
| E6 | 1 | 0/1 (0%) |
| E7 | 34 | 0/4 (0%) |
| WS-control (wild-type) | NA | 28/28 (100%) |
| nim1-1 phenotype control | NA | 0/34 (0%) |

NA - not applicable

Example 11

Sequencing of the NIM1 Gene Region

BAC04 DNA (25 ug, obtained from KeyGene) was the source of DNA used for sequence analysis, as this BAC was the clone completely encompassing the region that complemented the nim1 mutants. BAC04 DNA was randomly sheared in a nebulizer to generate fragments with an average length of about 2 kb. Ends of the sheared fragments were repaired, and the fragments were purified. Prepared DNA was ligated with EcoRV-digested pBRKanF4 (a derivative of pBRKan$_{F1}$ (Bhat 1993)). Resulting kanamycin-resistant colonies were selected for plasmid isolation using the Wizard Plus 9600 Miniprep System (Promega). Plasmids were sequenced using dye terminator chemistry (Applied BioSystems, Foster City, Calif.) with primers designed to sequence both strands of the plasmids (M13-21 forward and T7 reverse, Applied BioSystems). Data was collected on AB1377 DNA sequencers. Sequences were edited and assembled into contigs using Sequencher 3.0 (GeneCodes Corp., Ann Arbor, Mich.), the Staden genome assembly programs, phred, phrap and crossmatch (Phil Green, Washington University, St. Louis, Mo.) and consed (David Gordon, Washington University, St. Louis, Mo.). DNA from the cosmids found to complement the nim1-1 mutation was sequenced using primers designed by Oligo 5.0 Primer Analysis Software (National Biosciences, Inc., Plymouth, Minn.). Sequencing of DNA from Ws-0 and the nim1 alleles and cDNAs was performed essentially as described above.

A region of approximately 9.9 kb defined by the overlap of cosmids E1 and D7 was identified by complementation analysis to contain the nim1 region. Primers that flanked the insertion site of the vector and that were specific to the cosmid backbone were designed using Oligo 5.0 Primer Analysis Software (National Biosciences, Inc.). DNA was isolated from cosmids D7 and E1 using a modification of the ammonium acetate method (Traynor, P. L., 1990. BioTechniques 9(6): 676.) This DNA was directly sequenced using Dye Terminator chemistry above. The sequence obtained allowed determination of the endpoints of the complementing region. The region defined by the overlap of cosmids E1 and D7 is presented as SEQ ID NO: 1.

A truncated version of the BamHI-EcoRV fragment was also constructed, resulting in a construct that contained none of the "Gene 3" region (FIG. 5D). The following approach was necessary due the presence of HindIII sites in the Bam-Spe region of the DNA. The BamHI-EcoRV construct was completely digested with SpeI, then was split into two separate reactions for double digestion. One aliquot was digested with BamHI, the other HindIII. A BamHI-SpeI fragment of 2816 bp and a HindIII-SpeI fragment of 1588 bp were isolated from agarose gels (QiaQuick Gel extraction kit) and were ligated to BamHI-HindIII-digested pSGCG01. DH5a was transformed with the ligation mix. Resulting colonies were screened for the correct insert by digestion with HindIII following preparation of DNA using Wizard Magic MiniPreps (Promega). A clone containing the correct construct was electroporated into Agrobacterium strain GV3101 for transformation of Arabidopsis plants.

Example 12

Sequence Analysis and Subcloning of the NIM1 Region

The 9.9 kb region containing the NIM1 gene was analyzed for the presence of open reading frames in all six frames using Sequencher 3.0 and the GCG package. Four regions containing large ORF's were identified as possible genes (Gene Regions 1–4 in FIG. 5D). These four regions were PCR amplified from DNA of the wild-type parent and the six different nim1 allelic variants nim1-1, -2, -3, -4, -5, and -6. Primers for these amplifications were selected using Oligo 5.0 (National Biosciences, Inc.) and were synthesized by Integrated DNA Technologies, Inc. PCR products were separated on 1.0% agarose gels and were purified using the QIAquick Gel Extraction Kit. The purified genomic PCR products were directly sequenced using the primers used for the initial amplification and with additional primers designed to sequence across any regions not covered by the initial primers. Average coverage for these gene regions was approximately 3.5 reads/base.

Sequences were edited and were assembled using Sequencher 3.0. Base changes specific to various nim1 alleles were identified only in the region designated Gene Region 2, as shown below in Table 5, which shows sequence variations among all six of the nim1 alleles.

TABLE 5

| | Gene Region | | | |
|---|---|---|---|---|
| Allele/ ecotype | 1 (bases 590– 1090) | 2 (NIM1) (bases 1380–4100) | 3 (bases 5870– 6840) | 4 (bases 8140– 9210) |
| nim1-1 | no changes | t inserted at 2981: change of 7AA and premature termination of protein. | no changes | no changes |
| nim1-2 | no changes | g to a at 2799: His to Tyr | no changes | no changes |
| nim1-3 | no changes | deletion of t at 3261: change of 10AA and premature termination of protein. | no changes | no changes |
| nim1-4 | no changes | c to t at 2402: Arg to lys | no changes | no changes |
| nim1-5 | no changes | c to t at 2402: Arg to lys | no changes | no changes |
| nim1-6 | g to a at 734: asp to lys | g to a at 2670: Gln to Stop | no changes | no changes |
| WS (compared to Columbia) | no changes | a to g at 1607: Ile to Leu<br>a to c at 2344: intron<br>t to g at 2480: Gln to Pro<br>g to c at 2894: Ser to Trp<br>ggc deleted at 3449: lose Ala<br>c to t at 3490: Ala to Thr<br>c to t at 3498: Ser to Asn<br>a to t at 3873: non-coding<br>g to a at 3992: non-coding<br>g to a at 4026: non-coding<br>g to a at 4061: non-coding | t to a at 5746<br>a to t at 5751<br>t to a at 5754<br>c to t at 6728<br>a to t at 6815<br>t to c at 6816 | t to g at 8705<br>g to t at 8729<br>g to t at 8739<br>g to t at 8784<br>c to a at 8789<br>c to t at 8812<br>a to g at 8829<br>t to g at 8856<br>a to c at 9004<br>a to t at 9011<br>a to g at 8461 |
| RNA detected | No | Yes | No | No |

Positions listed in the table relate to SEQ ID NO: 1. All alleles nim1-1 to nim1-6 are WS strain. Columbia-0 represents the wild type It is apparent that the NIM1 gene lies within Gene Region 2, because there are amino acid changes or alterations of sequence within the open reading frame of Gene Region 2 in all six nim1 alleles. At the same time, at least one of the nim1 alleles shows no changes in the open reading frames within Gene Regions 1, 3 and 4. Therefore, the only gene region within the 9.9 kb region that could contain the NIM1 gene is Gene Region 2.

The Ws section of Table 5 indicates the changes in the Ws ecotype of Arabidopsis relative to the Columbia ecotype of Arabidopsis. The sequences presented herein relate to the Columbia ecotype of Arabidopsis, which contains the wild type gene in the experiments described herein. The changes are listed as amino acid changes within Gene Region 2 (the NIM1 region) and are listed as changes in base pairs in the other regions.

The cosmid region containing the nim1 gene was delineated by a BamH1-EcoRV restriction fragment of ~5.3 kb. Cosmid DNA from D7 and plasmid DNA from pBlueScriptII(pBSII) were digested with BamHI and with EcoRV (NEB). The 5.3 kb fragment from D7 was isolated from agarose gels and was purified using the QIAquick gel extraction kit (# 28796, Qiagen). The fragment was ligated overnight to the Bam-EcoRV-digested pBSII and the ligation mixture was transformed into E. coli strain DH5a. Colonies containing the insert were selected, DNA was isolated, and confirmation was made by digestion with HindIII. The Bam-EcoRV fragment was then engineered into a binary vector (pSGCG01) for transformation into Arabidopsis.

Example 13

Northern Analysis of the Four Gene Regions

Identical Northern blots were made from RNA samples isolated from water-, SA-, BTH- and INA-treated Ws and nim1 lines as previously described in Delaney, et al. (1995). These blots were hybridized with PCR products generated from the four gene regions identified in the 9.9 kb NIM1 gene region (SEQ ID NO: 1). Only the gene region containing the NIM1 gene (Gene Region 2) had detectable hybridization with the RNA samples, indicating that only the NIM1 region no contains a detectable transcribed gene (FIG. 5D and Table 5).

Example 14

Complementation with Gene Region 2

Gene Region 2 (FIG. 5D) was also demonstrated to contain the functional NIM1 gene by doing additional complementation experiments. A BamHI/HindIII genomic DNA fragment containing Gene Region 2 was isolated from cosmid D7 and was cloned into the binary vector pSGCG01 containing the gene for kanamycin resistance. The resulting plasmid was transformed into the Agrobacterium strain GV3101 and positive colonies were selected on kanamycin. PCR was used to verify that the selected colony contains the plasmid. Kanamycin-sensitive nim1-1 plants were infiltrated with this bacteria as previously described. The resulting seed was harvested and planted on GM agar containing 50 $\mu$g/ml kanamycin. Plants surviving selection were transferred to soil and tested for complementation. Transformed plants and control Ws and nim1 plants were sprayed with 300 $\mu$m INA. Two days later, leaves were harvested for RNA extraction and PR-1 expression analysis. The plants were then sprayed with *Peronospora parasitica* (isolate Emwa) and grown as previously described. Ten days following fungal infection, plants were evaluated and scored positive or negative for fungal growth. All of the 15 transformed plants, as well as the Ws controls, were negative for fungal growth following INA treatment, while the nim1 controls were positive for fungal growth. RNA was extracted and analyzed as described above for these transformants and controls. Ws controls and all 15 transformants showed PR-1 gene induction following INA treatment, while the nim1 controls did not show PR-1 induction by INA.

Example 15

Isolation of a NIM1 cDNA

An Arabidopsis cDNA library made in the IYES expression vector (Elledge et al, 1991, PNAS 88, 1731–1735) was plated and plaque lifts were performed. Filters were hybridized with a $^{32}$P-labeled PCR product generated from Gene Region 2 (FIG. 5D). 14 positives were identified from a screen of approximately 150,000 plaques. Each plaque was purified and plasmid DNA was recovered. cDNA inserts were digested out of the vector using EcoRI, agarose-gel-purified and sequenced. Sequence obtained from the longest cDNA is indicated in SEQ ID NO:2 and FIG. 6. To confirm that the 5' end of the cDNA had been obtained, a Gibco BRL 5' RACE kit was used following manufacturer's instructions. The resulting RACE products were sequenced and found to include the additional bases indicated in FIG. 6. The transcribed region present in both cDNA clones and detected in RACE is shown as capital letters in FIG. 6. Changes in the alleles are shown above the DNA strand. Capitals indicate the presence of the sequence in a cDNA clone or detected after RACE PCR.

The same RNA samples produced in the induction studies (FIG. 3) were also probed with the NIM1 gene using a full-length cDNA clone as a probe. In FIG. 7 it can be seen that INA induced the NIM1 gene in the wild type Ws allele. However, the nim1-1 mutation allele showed a lower basal level expression of the NIM1 gene, and it was not inducible by INA. This was similar to what was observed in the nim1-3 allele and the nim1-6 allele. The nim1-2 allele showed approximately normal levels in the untreated sample and showed similar induction to that of the wild type sample, as did the nim1-4 allele. The nim1-5 allele seemed to show higher basal level expression of the NIM1 gene and much stronger expression when induced by chemical inducers.

D. NIM1 Homologues

Example 16

BLAST Search with the NIM1 Sequence

A multiple sequence alignment was constructed using Clustal V (Higgins, Desmond G. and Paul M. Sharp (1989), Fast and sensitive multiple sequence alignments on a microcomputer, CABIOS 5:151–153) as part of the DNA* (1228 South Park Street, Madison Wis., 53715) Lasergene Biocomputing Software package for the Macintosh (1994). Certain regions of the NIM1 protein are homologous in amino acid sequence to 4 different rice cDNA protein products. The homologies were identified using the NIM1 sequences in a GenBank BLAST search. Comparisons of the regions of homology in NIM1 and the rice cDNA products are shown in FIG. 8 (See also, SEQ ID NO:3 and SEQ ID NO's: 4–11). The NIM1 protein fragments show from 36 to 48% identical amino acid sequences with the 4 rice products.

Example 17

Isolation of Homologous Genes from Other Plants

Using the NIM1 cDNA as a probe, homologs of Arabidopsis NIM1 are identified through screening genomic or cDNA libraries from different crops such as, but not limited to those listed below in Example 22. Standard techniques for accomplishing this include hybridization screening of plated DNA libraries (either plaques or colonies; see, e.g. Sambrook et al., *Molecular Cloning*, eds., Cold Spring Harbor Laboratory Press. (1989)) and amplification by PCR using oligonucleotide primers (see, e.g. Innis et al., *PCR Protocols, a Guide to Methods and Applications* eds., Academic Press (1990)). Homologs identified are genetically engineered into the expression vectors herein and transformed into the above listed crops. Transformants are evaluated for enhanced disease resistance using relevant pathogens of the crop plant being tested.

NIM1 homologs in the genomes of cucumber, tomato, tobacco, maize, wheat and barley have been detected by DNA blot analysis. Genomic DNA was isolated from cucumber, tomato, tobacco, maize, wheat and barley, restriction digested with the enzymes BamHI, HindIII, Xbal, or SalI, electrophoretically separated on 0.8% agarose gels and transferred to nylon membrane by capillary blotting. Following UV-crosslinking to affix the DNA, the membrane was hybridized under low stringency conditions [(1% BSA; 520 mM NaPO$_4$, pH 7.2; 7% lauryl sulfate, sodium salt; 1 mM EDTA; 250 mM sodium chloride) at 55° C. for 18–24 h] with $^{32}$P-radiolabelled *Arabidopsis thaliana* NIM1 cDNA. Following hybridization the blots were washed under low stringency conditions [6 XSSC for 15 min. (X3) 3 XSSC for 15 min. (XI) at 55° C.; 1 XSSC is 0.15 M NaCl, 15 mM Na-citrate (pH 7.0)] and exposed to X-ray film to visualize bands that correspond to NIM1.

In addition, expressed sequence tags (EST) identified with similarity to the NIM1 gene such as the rice EST's described in Example 16 can also be used to isolate homologues. The rice EST's may be especially useful for isolation of NIM1 homologues from other monocots.

Homologues may be obtained by PCR. In this method, comparisons are made between known homologues (e.g., rice and Arabidopsis). Regions of high amino acid and DNA similarity or identity are then used to make PCR primers. Regions rich in M and W are best followed by regions rich in F, Y, C, H, Q, K and E because these amino acids are encoded by a limited number of codons. Once a suitable region is identified, primers for that region are made with a diversity of substitutions in the $3^{rd}$ codon position. This diversity of substitution in the third position may be constrained depending on the species that is being targeted. For example, because maize is GC rich, primers are designed that utilize a G or a C in the $3^{rd}$ position, if possible.

The PCR reaction is performed from cDNA or genomic DNA under a variety of standard conditions. When a band is apparent, it is cloned and/or sequenced to determine if it is a NIM1 homologue.

E. High-Level Expression of NIM1 Confers Disease Resistance In Plants

High-level expression of the NIM1 gene in transgenic plants to confer a CIM phenotype is also described in Applicants' U.S. patent application Ser. No. 08/773,554, filed Dec. 27, 1996, which is incorporated by reference herein in its entirety.

Example 18

High-Level Expression of NIM1 Due To Insertion Site Effect

To determine if any of the transformants described above in Example 10/Table 4 had high-level expression of NIM1 due to insertion site effect, primary transformants containing the D7, D5 or E1 cosmids (containing the NIM1 gene) were selfed and the T2 seed collected. Seeds from one E1 line, four D5 lines and 95 D7 lines were sown on soil and grown as described above. When the T2 plants had obtained at least four true leaves, a single leaf was harvested separately for each plant. RNA was extracted from this tissue and analyzed for PR-1 and NIM1 expression. Plants were then inoculated with *P. parasitica* (Emwa) and analyzed for fungal growth at 3–14 days, preferably 7–12 days, following infection. Plants showing higher than normal NIM1 and PR-1 expression and displaying fungal resistance demonstrated that high-level expression of NIM1 confers a CIM phenotype.

Table 6 shows the results of testing of various transformants for resistance to fungal infection. As can be seen from the table, a number of transformants showed less than normal fungal growth and several showed no visible fungal growth at all. RNA was prepared from collected samples and analyzed as previously described (Delaney et al, 1995). Blots were hybridized to the Arabidopsis gene probe PR-1 (Uknes et al, 1992). Lines D7-74, D5-6 and E1-1 showed early induction of PR-1 gene expression, whereby PR-1 mRNA was evident by 24 or 48 hours following fungal treatment. These three lines also demonstrated resistance to fungal infection.

TABLE 6

| Line | P. parasitica growth |
| --- | --- |
| D7-2 | negative |
| 3 | + |
| 9 | + |
| 11 | + |
| 12 | + |
| 13 | + |
| 14 | + |
| 17 | + |
| 18 | + |
| 19 | + |
| 20 | + |
| 21 | + |
| 22 | + |
| 23 | + |
| 24 | + |
| 25 | + |
| 28 | + |
| 29 | + |
| 31 | + |
| 32 | + |
| 33 | + |
| 34 | + |
| 35 | + |
| 36 | + |
| 38 | + |
| 39 | + |
| 42 | + |
| 43 | + |
| 46 | + |
| 47 | + |
| 48 | + |
| 49 | + |
| 50 | + |
| 51 | + |
| 52 | + |
| 53 | + |
| 54 | +/− |
| 56 | + |
| 57 | + |
| 58 | + |
| 59 | + |
| 60 | + |
| 61 | + |
| 62 | + |
| 63 | + |

TABLE 6-continued

| Line | P. parasitica growth |
| --- | --- |
| 64 | + |
| 66 | + |
| 67 | + |
| 68 | + |
| 69 | + |
| 70 | + |
| 71 | + |
| 72 | + |
| 73 | + |
| 74 | negative |
| 75 | + |
| 77 | + |
| 78 | + |
| 79 | + |
| 80 | +/− |
| 81 | + |
| 82 | + |
| 83 | + |
| 84 | + |
| 85 | + |
| 86 | + |
| 87 | +/− |
| 89 | negative |
| 90 | + |
| 91 | + |
| 92 | + |
| 93 | + |
| 94 | + |
| 95 | + |
| 96 | + |
| 97 | + |
| 98 | +/− |
| 100 | +/− |
| 101 | +/− |
| 102 | +/− |
| 103 | + |
| 104 | + |
| 106 | + |
| 107 | + |
| 108 | + |
| 114 | + |
| 115 | + |
| 118 | + |
| 119 | + |
| 122 | + |
| 123 | + |
| 124 | + |
| 125 | + |
| 126 | + |
| 128 | + |
| 129 | + |
| 130 | + |
| D5-1 | + |
| 2 | + |
| 4 | + |
| 6 | +/− |
| E1-1 | negative |

Plants were treated with *P. parasitica* isolate Emwa and scored 10 days later.
+, normal fungal growth
+/−, less than normal fungal growth
negative, no visible fungal growth Example 19

35S Driven Expression of NIM1

Plants constitutively expressing the NIM1 gene are also generated from transformation of Ws or Col wild type plants with the BamHI-HindIII Arabidopsis genomic fragment (FIG. 6) cloned into pSGCG01 transformed into the Agrobacterium strain GV3101 (pMP90, Koncz and Schell, 1986, Mol. Gen. Genet. 204:383–396). In another construct, the full-length NIM1 cDNA is cloned into the EcoRI site of pCGN1761 ENX (Comai et al, 1990, Plant Mol. Biol. 15, 373–381). From the resulting plasmid, an XbaI fragment containing an enhanced CaMV 35S promoter, the NIM1 cDNA in the correct orientation for transcription and a tml 3' terminator is obtained. This fragment is cloned into the binary vector pCIB200 and transformed into GV3101. Ws or Col plants are infiltrated as previously described with each of these transformed strains. The resulting seed is harvested and plated on GM agar containing 50 mg/ml kanamycin. Surviving plantlets are transferred to soil and tested.

Example 20

Generation of Altered NIM1 Forms Using the NIM1 Gene and 35S Promoter

A BamHI/HindIII Arabidopsis genomic fragment (FIG. 6: bases 1249–5655) containing the NIM1 promoter, gene and downstream sequence cloned into pSGCG01 is restriction endonuclease digested with PstI and the ends made blunt with T4 polymerase. The fragment is further restriction endonuclease digested with SpeI yielding a 2162 bp fragment. The NIM1 cDNA cloned into the EcoRI site of pCGN1761ENX (see above) is restriction endonuclease digested with NotI and the ends made blunt with T4 polymerase. The fragment is further restriction endonuclease digested with SpeI. The 2162 bp genomic NIM1 fragment from above is ligated with the pCGN 1761ENX vector containing 91 bp of the NIM1 cDNA. The transformation cassette including the 35S promoter and tml terminator is released from pCGN1761ENX by partial restriction digestion with XbaI and ligated into the XbaI site of dephosphorylated pCIB200. The resulting plasmid is transformed into GV3101 and Ws or Col plants are infiltrated as previously described. Seeds are plated, and surviving plantlets are selected as described above.

Example 21

Assessment of CIM Phenotype in the High-Level Expression Transformants of NIM1

A leaf from each primary transformant is harvested, RNA is isolated (Verwoerd et al., 1989, Nuc Acid Res, 2362) and tested for constitutive PR-1 expression and NIM1 expression by RNA blot analysis (Uknes et al., 1992). Each transformant is evaluated for an enhanced disease resistance response indicative of constitutive SAR expression analysis (Uknes et al., 1992). Conidial suspensions of 5–10×10$^4$ spores/ml from two compatible P. parasitica isolates, Emwa and Noco (i.e. these fungal strains cause disease on wildtype Ws-O and Col-0 plants, respectively), are prepared and transformants are sprayed with the appropriate isolate depending on the ecotype of the transformant. Inoculated plants are incubated under high humidity for 7 days. Plants are disease rated at day 7 and a single leaf is harvested for RNA blot analysis utilizing a probe which provides a means to measure fungal infection.

Transformants that exhibit a CIM phenotype are taken to the F1 generation and homozygous plants are identified. Transformants are subjected to a battery of disease resistance tests. Fungal infection with Noco and Emwa are performed and leaves stained with lactophenol blue to identify the presence of fungal hyphae as described in Dietrich et al., (1994). Transformants are infected with the bacterial pathogen Pseudomonas syringae DC3000 to evaluate the spectrum of resistance evident as described in Uknes et al., (1993). Uninfected plants are evaluated for both free and glucose-conjugated SA and leaves are stained with lactophenol blue to evaluate for the presence of microscopic lesions. Resistant plants are sexually crossed with SAR mutants such as NahG and ndr1 to establish the epistatic relationship of the resistance phenotype to other mutants and evaluate how these dominant negative mutants of NIM1 may influence the SA-dependent feedback loop.

Example 22

High Level Expression of NIM1 in Crop Plants

Those constructs conferring a CIM phenotype in Col-0 or Ws-0 and others are transformed into crop plants for evaluation. Although the NIM1 gene can be inserted into any plant cell falling within these broad classes, it is particularly useful in crop plant cells, such as rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane. Transformants are evaluated for enhanced disease resistance. In a preferred embodiment of the invention, the expression of the NIM1 gene is at a level which is at least two-fold above the expression level of the NIM1 gene in wild type plants and is preferably ten-fold above the wild type expression level.

F. Other Uses of nim Phenotype Plants Generally

Example 23

The Use of nim Mutants in Disease Testing nim mutants are challenged with numerous pathogens and found to develop larger lesions more quickly than wild-type plants. This phenotype is referred to as UDS (i.e. universal disease susceptibility) and is a result of the mutants failing to express SAR genes to effect the plant defense against pathogens. The UDS phenotype of nim mutants renders them useful as control plants for the evaluation of disease symptoms in experimental lines in field pathogenesis tests where the natural resistance phenotype of so-called wild type lines may vary (i.e. to different pathogens and different pathotypes of the same pathogen). Thus, in a field environment where natural infection by pathogens is being relied upon to assess the resistance of experimental lines, the incorporation into the experiment of nim mutant lines of the appropriate crop plant species would enable an assessment of the true level and spectrum of pathogen pressure, without the variation inherent in the use of non-experimental lines.

Example 24

Assessment of the Utility of Transgenes for the Purposes of Disease Resistance nim mutants are used as host plants for the transformation of transgenes to facilitate their assessment for use in disease resistance. For example, an Arabidopsis nim mutant line, characterized by its UDS phenotype, is used for subsequent transformations with candidate genes for disease resistance thus enabling an assessment of the contribution of an individual gene to resistance against the basal level of the UDS nim mutant plants.

Example 25 nim Mutants as a Tool in Understanding Plant-Pathogen Interactions nim mutants are useful for the understanding of plant pathogen interactions, and in particular for the understanding of the processes utilized by the pathogen for the invasion of plant cells. This is so because nim mutants do not mount a systemic response to pathogen attack, and the unabated development of the pathogen is an ideal scenario in which to study its biological interaction with the host.

Of further significance is the observation that a host nim mutant may be susceptible to pathogens not normally associated with that particular host, but instead associated with a different host. For example, an Arabidopsis nim mutant such as nim1-1, -2, -3, -4, -5, or -6 is challenged with a number of pathogens that normally only infect tobacco, and found to be susceptible. Thus, the nim mutation causing the UDS phenotype leads to a modification of pathogen-range susceptibility and this has significant utility in the molecular, genetic and biochemical analysis of host-pathogen interaction.

Example 26 nim Mutants for Use in Fungicide Screening nim mutants are particularly useful in the screening of new chemical compounds for fungicide activity. nim mutants selected in a particular host have considerable utility for the screening of fungicides using that host and pathogens of the host. The advantage lies in the UDS phenoytpe of the mutant that circumvents the problems encountered by the host being differentially susceptible to different pathogens and pathotypes, or even resistant to some pathogens or pathotypes. By way of example, nim mutants in wheat could be effectively used to screen for fungicides to a wide range of wheat pathogens and pathotypes as the mutants would not mount a resistance response to the introduced pathogen and would not display differential resistance to different pathotypes that might otherwise require the use of multiple wheat lines, each adequately susceptible to a particular test pathogen. Wheat pathogens of particular interest include (but are not limited to) *Erisyphe graminis* (the causative agent of powdery mildew), *Rhizoctonia solani* (the causative agent of sharp eyespot), *Pseudocercosporella herpotrichoides* (the causative agent of eyespot), Puccinia spp. (the causative agents of rusts), and *Septoria nodorum*. Similarly, nim mutants of corn would be highly susceptible to corn pathogens and therefore useful in the screening for fungicides with activity against corn diseases.

nim mutants have further utility for the screening of a wide range of pathogens and pathotypes in a heterologous host i.e. in a host that may not normally be within the host species range of a particular pathogen and that may be particularly easily to manipulate (such as Arabidopsis). By virtue of its UDS phenotype the heterologous host is susceptible to pathogens of other plant species, including economically important crop plant species. Thus, by way of example, the same Arabidopsis nim mutant could be infected with a wheat pathogen such as *Erisyphe graminis* (the causative agent of powdery mildew) or a corn pathogen such as *Helminthosporium maydis* and used to test the efficacy of fungicide candidates. Such an approach has considerable improvements in efficiency over currently used procedures of screening individual crop plant species and different cultivars of species with different pathogens and pathotypes that may be differentially virulent on the different crop plant cultivars. Furthermore, the use of Arabidopsis has advantages because of its small size and the possibility of thereby undertaking more tests with limited resources of space.

DEPOSITS

The following vector molecules have been deposited under the terms of the Budapest Treaty with American Type Culture Collection 12301 Parklawn Drive Rockville, Md. 20852, U.S.A. on the dates indicated below:

Plasmid BAC-04 was deposited with ATCC on May 8, 1996 as ATCC 97543.

Plasmid P1-18 was deposited with ATCC on Jun. 13, 1996 as ATCC 97606.

Cosmid D7 was deposited with ATCC on Sep. 25, 1996 as ATCC 97736.

REFERENCES

The disclosures of each of the following references are hereby expressly incorporated by reference into the instant disclosure:

Altschul, S. F., Gish, W., Miller, W., Myers, E. W. and Lipman, D. J. (1990). Basic local alignment search tool. J. Mol. Biol. 215, 403–410.

Ausubel, F. M., Brent, R., Kingston, R. E., Moore, D. D., Seidman, J. G., Smith, J. A., and Struhl, K., eds (1987). Current Protocols in Molecular Biology. (New York: J. Wiley and Sons).

Bechtold, N., Ellis, J., and Pelletier, G. (1993). In *planta Agrobacterium* mediated gene transfer by infiltration of adult *Arabidopsis thaliana* plants. Comptes Rendus de l'Academie des Sciences Paris, Serie Sciences De La Vie 316, 494–499.

Bell, C., and Ecker, J. (1994). Assignment of 30 microsatellite loci to the linkage map of Arabidopsis. Genomics 19, 137–144.

Bhat, K. (1993). Generation of a plasmid vector for deletion cloning by rapid multiple site-directed mutagenesis. Gene 134, 83–87.

Bi, Y. M., Kenton, P., Mur, L., Darby, R., and Draper, J. (1995). Hydrogen peroxide does not function downstream of salicylic acid in the induction of PR protein expression. Plant J. 8, 235–245.

Bowling, S. A., Guo, A., Cao, H., Gordon, A. S., Klessig, D. F., and Dong, X. I. (1994). A mutation in Arabidopsis that leads to constitutive expression of systemic acquired resistance. Plant Cell 6, 1845–1857.

Cameron, R. K., Dixon, R. A., and Lamb, C. J. (1994). Biologically induced systemic acquired resistance in *Arabidopsis thaliana*. Plant J. 5, 715–725.

Century, K. S., Holub, E. B., and Staskawicz, B. J. (1995). NDR1, a locus of *Arabidopsis thaliana* that is required for disease resistance to both a bacterial and a fungal pathogen. Proc. Natl. Acad. Sci. USA 92, 6597–6601.

Chio, S., Creelman, R., J., M., and Wing, R. (1995). Construction and characterization of a bacterial artificial chromosome library of *Arabidopsis thaliana*. Plant Mol. Biol. 13, 124–128.

Creusot, F., Fouilloux, E., Dron, M., Lafleuriel, J., Picard, G., Billaut, A., Le Paslier, D., Cohen, D., Chaboute, M. -E., Durr, A., Fleck, J., Gigot, C., Camilleri, C., Bellini, C., Caboche, M., and Bouchez, D. (1995). The CIC library: a large insert YAC library for genome mapping in *Arabidopsis thaliana*. Plant J. 8, 763–770.

Delaney, T. P. (1997) Genetic dissection of acquired resistance to disease. Plant Physiology. 113, 5–12.

Delaney, T. P., Uknes, S., Vemooij, B., Friedrich, L., Weymann, K., Negrotto, D., Gaffney, T., Gutrella, M., Kessmann, H., Ward, E., and Ryals, J. (1994). A central role of salicylic acid in plant disease resistance. Science 266, 1247–1250.

Delaney, T. P., Friedrich, L., and Ryals, J. A. (1995). Arabidopsis signal transduction mutant defective in chemically and biologically induced disease resistance. Proceedings of the National Academy of Sciences of the United States of America 92, 6602–6606.

Dempsey, D. A., and Klessig, D. F. (1995). Signals in plant disease resistance. Bulletin de L'Institut Pasteur 93, 167–186.

Dietrich, R. A., Delaney, T. P., Uknes, S. J., Ward, E. R., Ryals, J. A., and Dangl, J. L. (1994). Arabidopsis mutants simulating disease resistance response. Cell 77, 565–577.

Friedrich, L., Lawton, K., Ruess, W., Masner, P., Specker, N., Gut Rella, M., Meier, B., Dincher, S., Staub, T., Uknes, S., Metraux, J. -P., Kessmann, H., and Ryals, J. (1996). A benzothiadiazole derivative induces systemic acquired resistance in tobacco. The Plant Journal 10(1), 61–70.

Elledge, S., Mulligan, J., Ramer, S., Spottswood, M., and Davis, R. (1991). 1 Yes: A multiunctional cDNA expression vector for the isolation of genes by complementation of yeast and *Escherichia coli* mutations. Proc. Natl. Acad. Sci. 88, 1731–1735.

Gaffney, T., Friedrich, L., Vernooij, B., Negrotto, D., Nye, G., Uknes, S., Ward, E., Kessmann, H., and Ryals, J. (1993). Requirement of salicylic acid for the induction of systemic acquired resistance. Science 261, 754–756.

Greenberg, J. T., Guo, A. L., Klessig, D. F., and Ausubel, F. M. (1994). Programmed cell death in plants-a pathogen-triggered response activated coordinately with multiple defense functions. Cell 77, 551–563.

Hebsgaard, S., Korning, P., Tolstrup, J., Engelbrecht, J., Rouze, P., and Brunak, S. (1996). Spice site prediction in *Arabidopsis thaliana* pre-mRNA by combining local and global sequence information. Nucleic Acids Res. 24, 3439–3452.

Higgins, D. G. and Sharp, P. M. (1989). Fast and sensitive multiple sequence alignments on a microcomputer. CABIOS 5,151–153.

Hunt, M., and Ryals, J. (1996). Systemic acquired resistance signal transduction. Crit. Rev. in Plant Sci. 15, 583–606.

Lawton, K., Uknes, S., Friedrich, L., Gaffney, T., Alexander, D., Goodman, R., Metraux, J. -P., Kessmann, H., Ahl-Goy, P., Gut Rella, M., Ward, E., and Ryals, J. (1993). The molecular biology of systemic acquired resistance. In Mechanisms of Defence Responses in Plants B. Fritig and M. Legrand, eds (Dordrecht, The Netherlands: Kluwer Academic Publishers), pp. 422–432.

Lawton, K. A., Friedrich, L., Hunt, M., Weymann, K., Delaney, T., Kessmann, H., Staub, T., and Ryals, J. (1996). Benzothiadiazole induces disease resistance in Arabidopsis by activation of the systemic acquired resistance signal transduction pathway. Plant J. 10, 71–82.

Liu, Y. -G., Mitsukawa, N., Vazquez-tello, A., and Whittier, R. (1995). Generation of a high-quality P1 library of Arabidopsis suitable for chromosome walking. Plant J. 7, 351–358.

Maher, E. A., Bate, N. J., Ni, W. T., Elkind, Y., Dixon, R. A., and Lamb, C. J. (1994). Increased disease susceptibility of transgenic tobacco plants with suppressed levels of preformed phenylpropanoid products. Proc. Natl. Acad. Sci. USA 91, 7802–7806.

Mauch-Mani, B., and Slusarenko, A. J. (1994). Systemic acquired resistance in *Arabidopsis thaliana* induced by a predisposing infection with a pathogenic isolate of *fusarium oxysporum*. Molecular Plant-Microbe Interactions 7, 378–383.

Mauch-Mani, B., and Slusarenko, A. J. (1996). Production of salicylic acid precursors is a major function of phenylalanine ammonia-lyase in the resistance of Arabidopsis to *Peronospora parasitica*. Plant Cell 8, 203–212.

Mindrinos, M., Katagiri, F., Yu, G. L. and Ausubel, F. (1994) The *Arabidopsis thaliana* disease resistance gene rps2 encodes a protein containing a nucleotide-binding site and leucine-rich repeats. Cell 78, 1089–1099.

Pallas, J., Paiva, N., Lamb, C., and Dixon, R. (1996). Tobacco plants epigenetically suppressed in phenylalanine ammonia-lyase expression do not develop systemic acquired resistance in response to infection by tobacco mosaic virus. Plant J. 10, 281–293.

Ryals, J. A., Neuenschwander, U. H., Willits, M. G., Molina, A., Steiner, H. -Y., and Hunt, M. D. (1996). Systemic acquired resistance. Plant Cell 8, 1809–1819.

Sambrook, J., Fritsch, E. F., and Maniatis, T. (1989). Molecular Cloning: A Laboratory Manual. (Cold Spring Harbor, NY:: Cold Spring Harbor Laboratory Press).

Shulaev, V., Léon, J., and Raskin, I. (1995). Is salicylic acid a translocated signal of systemic acquired resistance in tobacco. Plant Cell 7, 1691–1701.

Uknes, S., Mauch-Mani, B., Moyer, M., Potter, S., Williams, S., Dincher, S., Chandler, D., Slusarenko, A., Ward, E., and Ryals, J. (1992). Acquired resistance in Arabidopsis. Plant Cell 4, 645–656.

Uknes, S., Winter, A. M., Delaney, T., Vernooij, B., Morse, A., Friedrich, L., Nye, G., Potter, S., Ward, E., and Ryals, J. (1993). Biological induction of systemic acquired resistance in Arabidopsis. Mol. Plant-Microbe Interact. 6, 692–698.

Vernooij, B., Friedrich, L., Goy, P. A., Staub, T., Kessmann, H., and Ryals, J. (1995). 2,6-dichloroisonicotinic acid-induced resistance to pathogens without the accumulation of salicylic acid. Molecular Plant-Microbe Interactions 8, 228–234.

Vernooij, B., Friedrich, L., Morse, A., Reist, R., Kolditz-Jawhar, R., Ward, E., Uknes, S., Kessmann, H., and Ryals, J. (1994). Salicylic acid is not the translocated signal responsible for inducing systemic acquired resistance but is required in signal reduction. Plant Cell 6, 959–965.

Verwoerd, B., Dekker, M., and Hoekema, A. (1989). A small-scale procedure for the rapid isolation of plant RNAs. Nucleic Acids Res. 17, 2362.

Vos, P., Hogers, R., Bleeker, M., Reijans, M., van de Lee, T., Hornes, M., Frijters, A., Pot, J., Pelema, J., Kuiper, M., and Zabeau, M. (1995). AFLP: a new technique for DNA fingerprinting. Nucleic Acids Res. 23, 4407–4414.

Ward, E. R., Uknes, S. J., Williams, S. C., Dincher, S. S., Wiederhold, D. L., Alexander, D. C., Ahl-Goy, P., Metraux, J. P., and Ryals, J. A. (1991). Coordinate Gene Activity in Response to Agents That Induce Systemic Acquired Resistance. Plant Cell 3, 1085–1094.

Weymann, K., Hunt, M., Uknes, S., Neuenschwander, U., Lawton, K., Steiner, H. -Y., and Ryals, J. (1995). Suppression and restoration of lesion formation in Arabidopsis lsd mutants. Plant Cell 7, 2013–2022.

What is claimed is:

1. An isolated DNA molecule that encodes a protein involved in the signal transduction cascade leading to systemic acquired resistance in plants, wherein said DNA molecule is comprised within clone BAC-04, ATCC Deposit No. 97543.

2. An isolated DNA molecule that encodes a protein involved in the signal transduction cascade leading to systemic acquired resistance in plants, wherein said protein comprises the amino acid sequence set forth in SEQ ID NO:3.

3. An isolated DNA molecule that encodes a protein involved in the signal transduction cascade leading to systemic acquired resistance in plants, wherein said DNA molecule comprises the coding sequence set forth in SEQ ID NO: 2.

4. A chimeric gene comprising a promoter active in plants operatively linked to the DNA molecule of claim 1.

5. A recombinant vector comprising the chimeric gene of claim 4.

6. A host cell stably transformed with the recombinant vector of claim 5.

7. A plant stably transformed with the recombinant vector of claim 5.

8. The plant of claim 7, which is selected from the following: rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

9. The plant of claim 7, wherein said protein is expressed in said plant at higher levels than in a wild type plant.

10. A method of increasing SAR gene expression in a plant, comprising transforming the plant with the recombinant vector of claim 5.

11. A method of enhancing disease resistance in a plant, comprising transforming the plant with the recombinant vector of claim 5.

12. A chimeric gene comprising a promoter active in plants operatively linked to the DNA molecule of claim 2.

13. A recombinant vector comprising the chimeric gene of claim 12.

14. A host cell transformed with the recombinant vector of claim 13.

15. A plant stably transformed with the recombinant vector of claim 13.

16. The plant of claim 15, which is selected from the following: rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

17. A method of increasing SAR gene expression in a plant, comprising transforming the plant with the recombinant vector of claim 13.

18. A method of enhancing disease resistance in a plant, comprising transforming the plant with the recombinant vector of claim 13.

19. A chimeric gene comprising a promoter active in plants operatively linked to the DNA molecule of claim 3.

20. A recombinant vector comprising the chimeric gene of claim 19.

21. A host cell stably transformed with the recombinant vector of claim 20.

22. A plant stably transformed with the recombinant vector of claim 20.

23. The plant of claim 22, which is selected from the following: rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

24. A method of increasing SAR gene expression in a plant, comprising transforming the plant with the recombinant vector of claim 20.

25. A method of enhancing disease resistance in a plant, comprising transforming the plant with the recombinant vector of claim 20.

* * * * *